(12) United States Patent
Arimori

(10) Patent No.: US 10,085,450 B2
(45) Date of Patent: Oct. 2, 2018

(54) TETRAZOLINONE COMPOUND AND USE THEREOF

(71) Applicant: SUMITOMO CHEMICAL COMPANY, LIMITED, Tokyo (JP)

(72) Inventor: Sadayuki Arimori, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/029,365

(22) PCT Filed: Oct. 14, 2014

(86) PCT No.: PCT/JP2014/077764
§ 371 (c)(1),
(2) Date: Apr. 14, 2016

(87) PCT Pub. No.: WO2015/056806
PCT Pub. Date: Apr. 23, 2015

(65) Prior Publication Data
US 2016/0270399 A1     Sep. 22, 2016

(30) Foreign Application Priority Data
Oct. 17, 2013  (JP) .................. 2013-216076

(51) Int. Cl.
| A01N 43/713 | (2006.01) |
| C07D 403/12 | (2006.01) |
| C07D 417/12 | (2006.01) |
| A01N 43/76 | (2006.01) |
| A01N 43/78 | (2006.01) |
| A01N 43/82 | (2006.01) |
| C07D 409/12 | (2006.01) |
| C07D 413/12 | (2006.01) |

(52) U.S. Cl.
CPC ........... *A01N 43/713* (2013.01); *A01N 43/76* (2013.01); *A01N 43/78* (2013.01); *A01N 43/82* (2013.01); *C07D 403/12* (2013.01); *C07D 409/12* (2013.01); *C07D 413/12* (2013.01); *C07D 417/12* (2013.01)

(58) Field of Classification Search
CPC ...... A01N 43/713; A01N 43/76; A01N 43/78; A01N 43/82; C07D 403/12; C07D 409/12; C07D 413/12; C07D 417/12
See application file for complete search history.

(56) References Cited
U.S. PATENT DOCUMENTS
7,056,941 B1  6/2006  Müller et al.

FOREIGN PATENT DOCUMENTS
| WO | WO 96/36229 A1 | 11/1996 |
| WO | WO 98/23156 A1 | 6/1998 |
| WO | WO 99/05139 A1 | 2/1999 |
| WO | WO 99/11129 A1 | 3/1999 |
| WO | WO 2013/162072 A1 | 10/2013 |
| WO | WO 2013/162077 A1 | 10/2013 |
| WO | 2014/051161 A1 | 4/2014 |
| WO | 2014/051165 A1 | 4/2014 |

OTHER PUBLICATIONS

Yanagi et al. (Pestic. Sci. 2002, 27, 199-209).*
English translation of the Written Opinion of the International Searching Authority, dated Nov. 11, 2014, for International Application No. PCT/JP2014/077764.
International Search Report issued in PCT/JP2014/077764 dated Nov. 11, 2014.
Chinese Office Action and Search Report, dated Dec. 29, 2016, for Chinese Application No. 201480056631.3, with an English translation of the Chinese Office Action only.
International Preliminary Report on Patentability and the Written Opinion of the International Searching Authority (Forms PCT/IB/338, PCT/IB/373 and PCT/ISA/237), dated Apr. 28, 2016, for International Application No. PCT/JP2014/077764.
Chinese Second Office Action (including an English translation thereof) issued in the corresponding Chinese Patent Application No. 201480056631.3 dated Jul. 19, 2017.
Extended European Search Report, dated May 26, 2017, for European Application No. 14854412.5.

* cited by examiner

*Primary Examiner* — Robert H Havlin
(74) *Attorney, Agent, or Firm* — Birch, Stewart, Kolasch & Birch, LLP

(57) ABSTRACT

A tetrazolinone compound represented by formula (1):

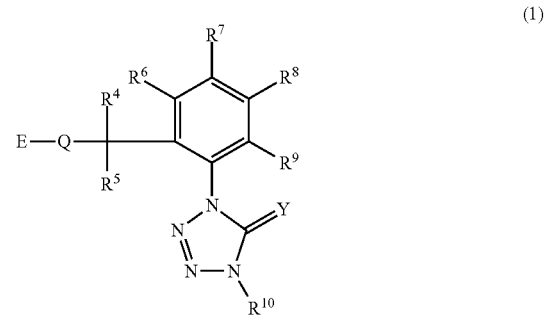

Wherein E represents a 5-membered aromatic heterocyclic group such as a pyrazolyl group, a thiazolyl group, or an imidazolyl group; $R^4$ and $R^5$ represent a hydrogen atom; $R^6$ represents an alkyl group having 1-12 carbon atoms; $R^7$, $R^8$, and $R^9$ represent a hydrogen atom; $R^{10}$ represents an alkyl group having 1-3 carbon atoms, or a haloalkyl group having 1-3 carbon atoms; Y represents an oxygen atom; and Q represents an oxygen atom, has excellent control activity against pests.

6 Claims, No Drawings

TETRAZOLINONE COMPOUND AND USE THEREOF

TECHNICAL FIELD

The present invention relates to a tetrazolinone compound and application for same.

BACKGROUND ART

Heretofore, various chemicals have been developed so as to control pests and provided in practice use, but in some cases, these chemicals may not exert enough activity.

Meanwhile, there have been known, as compounds having a tetrazolinone ring, compounds represented by formula (A):

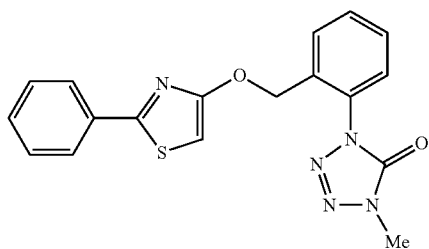

(see WO 96/36229 A).

DISCLOSURE OF THE INVENTION

The present invention provides compounds having excellent control activity against pests.

The present inventors have intensively studied so as to find compounds having excellent control activity against pests, and found that a tetrazolinone compound represented by the following formula (1) has excellent control activity against pests, thus completing the present invention.

The present invention includes the followings [1] to [4].
[1] A tetrazolinone compound represented by formula (1):

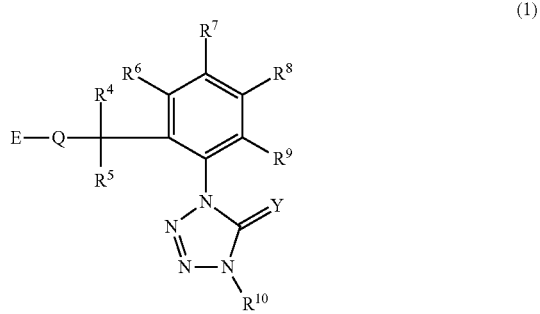

wherein
E represents a 5-membered aromatic heterocyclic group selected from Group $P^2$;
$R^4$ and $R^5$ each independently represents a hydrogen atom or an alkyl group having 1-3 carbon atoms; or
$R^4$ and $R^5$ may be taken together with the carbon atoms to which they are attached to form a cycloalkane ring having 3-6 carbon atoms;

$R^6$ represents an alkyl group having 1-12 carbon atoms, a halogen atom, a haloalkyl group having 1-12 carbon atoms, a cycloalkyl group having 3-12 carbon atoms, a halocycloalkyl group having 3-12 carbon atoms, an alkoxy group having 1-12 carbon atoms, a haloalkoxy group having 1-12 carbon atoms, an alkylthio group having 1-12 carbon atoms, a haloalkylthio group having 1-12 carbon atoms, a nitro group, a cyano group, a hydroxy group, a sulfanyl group, a pentafluorosulfanyl group, an alkenyl group having 2-12 carbon atoms, a haloalkenyl group having 2-12 carbon atoms, an alkynyl group having 2-12 carbon atoms, a haloalkynyl group having 2-12 carbon atoms, a cycloalkyloxy group having 3-12 carbon atoms, a halocycloalkyloxy group having 3-12 carbon atoms, a cycloalkylthio group having 3-12 carbon atoms, an alkenyloxy group having 2-12 carbon atoms, an alkynyloxy group having 2-12 carbon atoms, a haloalkenyloxy group having 2-12 carbon atoms, a haloalkynyloxy group having 2-12 carbon atoms, an alkynylthio group having 2-12 carbon atoms, an alkenylthio group having 2-12 carbon atoms, a haloalkenylthio group having 2-12 carbon atoms, a haloalkynylthio group having 2-12 carbon atoms, an alkylcarbonyl group having 2-12 carbon atoms, a haloalkylcarbonyl group having 2-12 carbon atoms, an alkylcarbonyloxy group having 2-12 carbon atoms, an alkylcarbonylthio group having 2-12 carbon atoms, an alkoxycarbonyl group having 2-12 carbon atoms, a trialkylsilyl group having 3-12 carbon atoms, a trialkylsilylethynyl group having 5-14 carbon atoms, an alkylsulfonyl group having 1-12 carbon atoms, a haloalkylsulfonyl group having 1-12 carbon atoms, an alkylsulfinyl group having 1-12 carbon atoms, a haloalkylsulfinyl group having 1-12 carbon atoms, an aminosulfonyl group which optionally has an alkyl group having 1-12 carbon atoms, an amino group which optionally has an alkyl group having 1-12 carbon atoms, an aminocarbonyl group which optionally has an alkyl group having 1-12 carbon atoms, a carboxy group, or a formyl group;

$R^7$, $R^8$, and $R^9$ each independently represents a hydrogen atom, an alkyl group having 1-12 carbon atoms, a halogen atom, a haloalkyl group having 1-12 carbon atoms, a cycloalkyl group having 3-12 carbon atoms, a halocycloalkyl group having 3-12 carbon atoms, an alkoxy group having 1-12 carbon atoms, a haloalkoxy group having 1-12 carbon atoms, an alkylthio group having 1-12 carbon atoms, a haloalkylthio group having 1-12 carbon atoms, a nitro group, a cyano group, a hydroxy group, a sulfanyl group, a pentafluorosulfanyl group, an alkenyl group having 2-12 carbon atoms, a haloalkenyl group having 2-12 carbon atoms, an alkynyl group having 2-12 carbon atoms, a haloalkynyl group having 2-12 carbon atoms, a cycloalkyloxy group having 3-12 carbon atoms, a halocycloalkyloxy group having 3-12 carbon atoms, a cycloalkylthio group having 3-12 carbon atoms, an alkenyloxy group having 2-12 carbon atoms, an alkynyloxy group having 2-12 carbon atoms, a haloalkenyloxy group having 2-12 carbon atoms, a haloalkynyloxy group having 2-12 carbon atoms, an alkynylthio group having 2-12 carbon atoms, an alkenylthio group having 2-12 carbon atoms, a haloalkenylthio group having 2-12 carbon atoms, a haloalkynylthio group having 2-12 carbon atoms, an alkylcarbonyl group having 2-12 carbon atoms, a haloalkylcarbonyl group having 2-12 carbon atoms, an alkylcarbonyloxy group having 2-12 carbon atoms, an alkylcarbonylthio group having 2-12 carbon atoms, an alkoxycarbonyl group having 2-12 carbon atoms, a trialkylsilyl group having 3-12 carbon atoms, a trialkylsilylethynyl group having 5-14 carbon atoms, an alkylsulfonyl group having 1-12 carbon atoms, a haloalkylsulfonyl group having 1-12 carbon atoms, an alkylsulfinyl group having 1-12 carbon atoms, a haloalkylsulfinyl group having 1-12 carbon atoms, an aminosulfonyl group which optionally has an alkyl group having 1-12 carbon atoms, an amino group which optionally has an alkyl group having 1-12 carbon atoms, an aminocarbonyl group which optionally has an alkyl group having 1-12 carbon atoms, a carboxy group, or a formyl group;

$R^{10}$ represents an alkyl group having 1-3 carbon atoms or a haloalkyl group having 1-3 carbon atoms;

Y represents an oxygen atom or a sulfur atom;

Q represents an oxygen atom, a sulfur atom, or an $NR^{12}$ group;

$R^{12}$ represents a hydrogen atom, an alkyl group having 1-6 carbon atoms, or a haloalkyl group having 1-6 carbon atoms:

Group $P^2$: Group consisting of the following structural formulas:

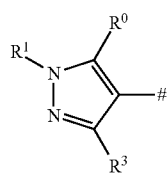
E1

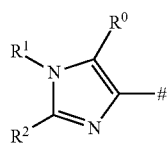
E2

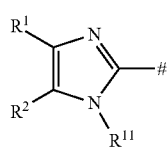
E3

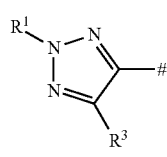
E4

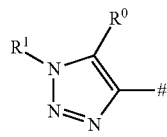
E5

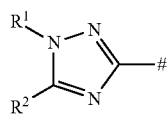
E6

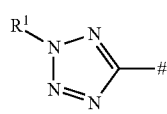
E7

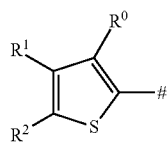
E8

-continued

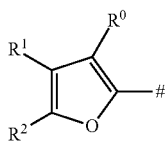
E9

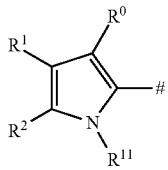
E10

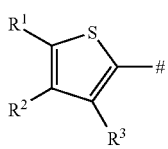
E11

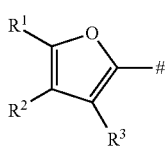
E12

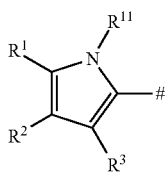
E13

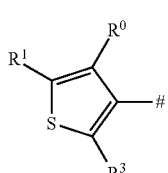
E14

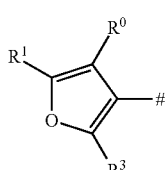
E15

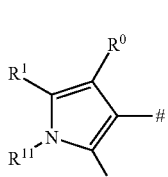
E16

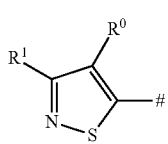
E17

E18 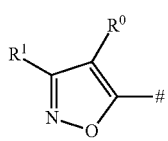
E19 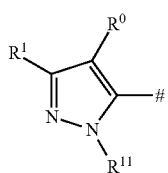
E20 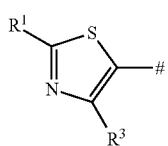
E21 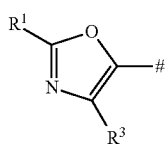
E22 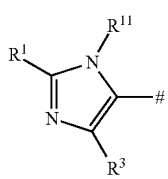
E23 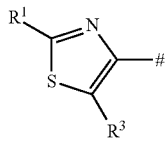
E24 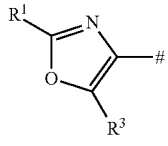
E25 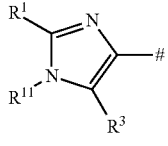
E26 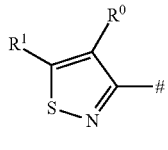
E27 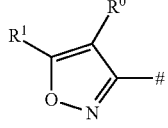
E28 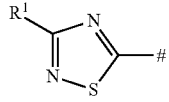
E29 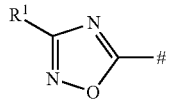
E30 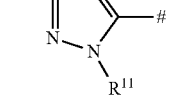
E31 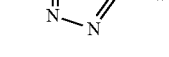
E32 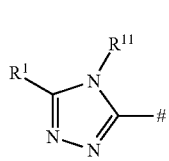
E33 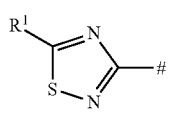
E34 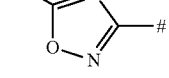
E35 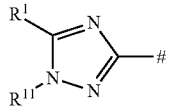
E36 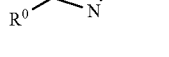
E37 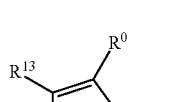
E38 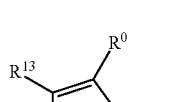
E39

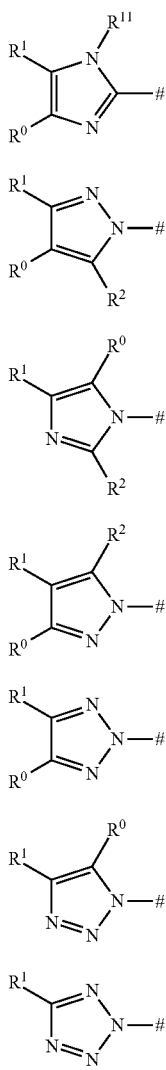

in which the symbol # represents a binding site for Q;

$R^0$, $R^2$, and $R^3$ each independently represents a hydrogen atom, a halogen atom, an alkyl group having 1-6 carbon atoms, a haloalkyl group having 1-6 carbon atoms, an alkenyl group having 2-6 carbon atoms, a haloalkenyl group having 2-6 carbon atoms, an alkynyl group having 2-6 carbon atoms, a haloalkynyl group having 2-6 carbon atoms, an alkoxycarbonyl group having 2-6 carbon atoms, a carboxy group, or a cyano group;

$R^1$ represents an aryl group having 6-16 carbon atoms which optionally has one or more atoms or groups selected from Group $P^1$, an aralkyl group having 7-18 carbon atoms which optionally has one or more atoms or groups selected from Group $P^1$, a cycloalkyl group having 3-12 carbon atoms which optionally has one or more atoms or groups selected from Group $P^1$, an adamantyl group optionally having one or more atoms or groups selected from Group $P^1$, or a hydrogen atom, wherein, when the aryl group having 6-16 carbon atoms, the aralkyl group having 7-18 carbon atoms, the cycloalkyl group having 3-12 carbon atoms, and the adamantyl group have two or more atoms or groups selected from Group $P^1$, the atoms or groups may be the same or different to each other;

$R^{11}$ represents a hydrogen atom, an alkyl group having 1-6 carbon atoms, a haloalkyl group having 1-6 carbon atoms, an alkenyl group having 2-6 carbon atoms, a haloalkenyl group having 2-6 carbon atoms, an alkynyl group having 2-6 carbon atoms, or a haloalkynyl group having 2-6 carbon atoms;

$R^{13}$ represents an aryl group having 6-16 carbon atoms which optionally has one or more atoms or groups selected from Group $P^1$, an aralkyl group having 7-18 carbon atoms which optionally has one or more atoms or groups selected from Group $P^1$, a cycloalkyl group having 3-12 carbon atoms which optionally has one or more atoms or groups selected from Group $P^1$, or an adamantyl group optionally having one or more atoms or groups selected from Group $P^1$, wherein, when two or more atoms or groups selected from Groups $P^1$ are present, the atoms or groups may be the same or different to each other:

Group $P^1$: Group consisting of a halogen atom, an alkyl group having 1-12 carbon atoms, a haloalkyl group having 1-12 carbon atoms, an alkoxy group having 1-12 carbon atoms, a haloalkoxy group having 1-12 carbon atoms, an alkylthio group having 1-12 carbon atoms, a haloalkylthio group having 1-12 carbon atoms, a carboxy group, a formyl group, a nitro group, a cyano group, a hydroxy group, a sulfanyl group, a pentafluorosulfanyl group, an alkenyl group having 2-12 carbon atoms, a haloalkenyl group having 2-12 carbon atoms, an alkynyl group having 2-12 carbon atoms, a haloalkynyl group having 2-12 carbon atoms, a cycloalkyl group having 3-12 carbon atoms, a halocycloalkyl group having 3-12 carbon atoms, a cycloalkyloxy group having 3-12 carbon atoms, a halocycloalkyloxy group having 3-12 carbon atoms, a cycloalkylthio group having 3-12 carbon atoms, an alkenyloxy group having 2-12 carbon atoms, an alkynyloxy group having 2-12 carbon atoms, a haloalkenyloxy group having 2-12 carbon atoms, a haloalkynyloxy group having 2-12 carbon atoms, an alkynylthio group having 2-12 carbon atoms, an alkenylthio group having 2-12 carbon atoms, a haloalkenylthio group having 2-12 carbon atoms, a haloalkynylthio group having 2-12 carbon atoms, an alkylcarbonyl group having 2-12 carbon atoms, a haloalkylcarbonyl group having 2-12 carbon atoms, an alkylcarbonyloxy group having 2-12 carbon atoms, an alkylcarbonylthio group having 2-12 carbon atoms, an alkoxycarbonyl group having 2-12 carbon atoms, an aryl group having 6-16 carbon atoms, a haloaryl group having 6-16 carbon atoms, an aryloxy group having 6-16 carbon atoms, a haloaryloxy group having 6-16 carbon atoms, an arylthio group having 6-16 carbon atoms, a haloarylthio group having 6-16 carbon atoms, an aralkyl group having 7-18 carbon atoms, a haloaralkyl group having 7-18 carbon atoms, an arylalkoxy group having 7-18 carbon atoms, a haloarylalkoxy group having 7-18 carbon atoms, a trialkylsilyl group having 3-12 carbon atoms, a trialkylsilylethynyl group having 5-14 carbon atoms, an alkylsulfonyl group having 1-12 carbon atoms, a haloalkylsulfonyl group having 1-12 carbon atoms, an arylsulfonyl group having 6-16 carbon atoms, a haloarylsulfonyl group having 6-16 carbon atoms, an alkylsulfinyl group having 1-12 carbon atoms, a haloalkylsulfinyl group having 1-12 carbon atoms, an arylsulfinyl group having 6-16 carbon atoms, a haloarylsulfinyl group having 6-16 carbon atoms, a polyoxalkyloxy group having 2-11 carbon atoms, a oxacycloalkyloxy group having 2-5 carbon atoms, an aminocarbonyl group which optionally has an alkyl group having 1-12 carbon atoms and/or an aryl group having 6-12 carbon atoms, an aminosulfonyl group which optionally has an alkyl group having 1-12 carbon atoms and/or an aryl group having 6-12 carbon atoms, and an amino group which optionally has an alkyl group having 1-12 carbon atoms].

[2] The tetrazolinone compound according to [1], wherein E is E1, E2, E3, E4, E5, E6, E7, E8, E9, E10, E11, E12, E13, E14, E15, E16, E17, E18, E19, E20, E21, E22, E23, E24, E25, E26, E27, E28, E29, E30, E31, E32, E33, E34, E35, or E36.

[3] The tetrazolinone compound according to [1] or [2], wherein E is E19;
$R^{11}$ is a hydrogen atom, an alkyl group having 1-3 carbon atoms, or a haloalkyl group having 1-3 carbon atoms;
$R^0$ is a hydrogen atom, a halogen atom, an alkyl group having 1-3 carbon atoms, or a haloalkyl group having 1-3 carbon atoms;
$R^1$ is an aryl group having 6-16 carbon atoms which optionally has one or more atoms or groups selected from Group $P^3$, or a hydrogen atom;
$R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, a haloalkoxy group having 1-3 carbon atoms, an alkylthio group having 1-3 carbon atoms, a cyano group, an alkenyl group having 2-3 carbon atoms, or an alkynyl group having 2-3 carbon atoms;
$R^7$, $R^8$, and $R^9$ each independently represents a hydrogen atom or a fluorine atom;
$R^{10}$ is a methyl group; and
Y and Q are oxygen atoms:
Group $P^3$: Group consisting of a halogen atom, an alkyl group having 1-3 carbon atoms, a haloalkyl group having 1-3 carbon atoms, an alkoxy group having 1-3 carbon atoms, a haloalkoxy group having 1-3 carbon atoms, an alkylthio group having 1-3 carbon atoms, a haloalkylthio group having 1-3 carbon atoms, a cycloalkyl group having 3-6 carbon atoms, an alkenyl group having 2-3 carbon atoms, an alkynyl group having 2-3 carbon atoms, and a cyano group.

[4] The tetrazolinone compound according to [1] or [2], wherein E is E8 or E11;
$R^0$, $R^2$, $R^3$, $R^7$, $R^8$, and $R^9$ are hydrogen atoms;
$R^1$ is an aryl group having 6 carbon atoms which optionally has one or more atoms or groups selected from Group $P^3$, or a hydrogen atom;
$R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, a haloalkoxy group having 1-3 carbon atoms, an alkylthio group having 1-3 carbon atoms, a cyano group, an alkenyl group having 2-3 carbon atoms, or an alkynyl group having 2-3 carbon atoms;
$R^{10}$ is a methyl group; and
Y and Q are oxygen atoms.

[5] A pest control agent comprising the tetrazolinone compound according to any one of [1] to [4].

[6] A method for controlling pests, which comprises applying an effective amount of the tetrazolinone compound according to any one of [1] to [4] to plants or soil.

[7] Use of the tetrazolinone compound according to any one of [1] to [4] for controlling pests.

According to the present invention, pests can be controlled.

MODE FOR CARRYING OUT THE INVENTION

A compound of the present invention is a tetrazolinone compound represented by formula (1):

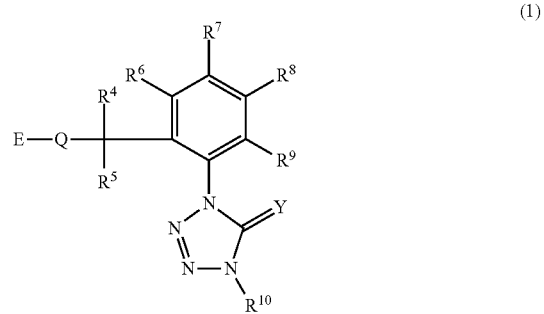

wherein symbols are the same as defined above (hereinafter sometimes referred to as the present compound).

In the present invention, the present control agent means a pest control agent including the present compound.

Substituents as used herein will be mentioned below.

Examples of the halogen atom include a fluorine atom, a chlorine atom, a bromine atom, and an iodine atom.

Examples of the alkyl group having 1-3 carbon atoms include a methyl group, an ethyl group, a propyl group, and an isopropyl group.

Examples of the alkyl group having 1-6 carbon atoms include a methyl group, an ethyl group, a propyl group, an isopropyl group, a butyl group, an isobutyl group, a sec-butyl group, a tert-butyl group, a pentyl group, and a hexyl group.

Examples of the alkyl group having 1-12 carbon atoms include a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, an undecyl group, and a dodecyl group.

The haloalkyl group having 1-3 carbon atoms represents a group in which at least one hydrogen atom of an alkyl group having 1-3 carbon atoms is substituted with a halogen atom, and examples thereof include a fluoromethyl group, a chloromethyl group, a dichloromethyl group, a difluoromethyl group, a trifluoromethyl group, a trichloromethyl group, a chlorofluoromethyl group, a dichlorofluoromethyl group, a 2,2,2-trifluoroethyl group, a pentafluoroethyl group, a 2,2-difluoroethyl group, a 2-fluoropropyl group, a 3-fluoropropyl group, a 2,2-difluoropropyl group, and a 3,3,3-trifluoropropyl group.

The haloalkyl group having 1-6 carbon atoms represents a group in which at least one hydrogen atom of an alkyl group having 1-6 carbon atoms is substituted with a halogen atom, and examples thereof include a fluoromethyl group, a chloromethyl group, a dichloromethyl group, a difluoromethyl group, a trifluoromethyl group, a trichloromethyl group, a 2,2,2-trifluoroethyl group, a 2,2,2-trichloroethyl group, a pentafluoroethyl group, a 2,2-difluoroethyl group, a 2-fluoropropyl group, a 3-fluoropropyl group, a 2,2-difluoropropyl group, a 3,3,3-trifluoropropyl group, a 3-(fluoromethyl)-2-fluoroethyl group, a 4-fluorobutyl group, and a 2,2-difluorohexyl group.

The haloalkyl group having 1-12 carbon atoms represents a group in which at least one hydrogen atom of an alkyl group having 1-12 carbon atoms is substituted with a halogen atom, and examples thereof include a fluoromethyl group, a chloromethyl group, a dichloromethyl group, a difluoromethyl group, a trifluoromethyl group, a trichloromethyl group, a 2,2,2-trifluoroethyl group, a pentafluoroethyl group, a 2,2-difluoroethyl group, a 2-fluoropropyl group, a 3-fluoropropyl group, a 2,2-difluoropropyl group, a 3,3,3-trifluoropropyl group, a 2-(fluoromethyl)-3-fluoropropyl group, a 4-fluorobutyl group, a 5-fluoropentyl group, a 2,2-difluorohexyl group, a perfluoroheptyl group, a perfluorooctyl group, a perfluorononyl group, a perfluorodecyl group, a perfluoroundecyl group, and a perfluorododecyl group.

Examples of the alkenyl group having 2-3 carbon atoms include a vinyl group, a 1-propenyl group, an isopropenyl group, and a 2-propenyl group.

Examples of the alkenyl group having 2-6 carbon atoms include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, a 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group, and a 5-hexenyl group.

Examples of the alkenyl group having 2-12 carbon atoms include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, a 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group, a 5-hexenyl group, a 1-heptenyl group, a 6-heptenyl group, a 1-octenyl group, a 7-octenyl group, a 1-nonenyl group, a 8-nonenyl group, a 1-decenyl group, a 9-decenyl group, a 1-undecenyl group, a 10-undecenyl group, a 1-dodecenyl group, and a 11-dodecenyl group.

The haloalkenyl group having 2-6 carbon atoms represents a group in which at least one hydrogen atom of an alkenyl group having 2-6 carbon atoms is substituted with a halogen atom, and examples thereof include a 2-fluorovinyl group, a 2-chlorovinyl group, a 2-bromovinyl group, a 2-iodovinyl group, a 2,2-difluorovinyl group, a 2,2-dichlorovinyl group, a 3,3-difluoro-2-propenyl group, a 3,3-dichloro-2-propenyl group, a 3-chloro-2-propenyl group, a 1-chloromethylvinyl group, a 1-trifluoromethylvinyl group, a 1-trifluoromethyl-2,2-difluorovinyl group, a 3,3-difluoro-2-propenyl group, a 4,4,4-trifluoro-2-butenyl group, a 3,4,4-trifluoro-3-butenyl group, a 3,3-difluoro-2-methyl-2-propenyl group, a 3,3,3-trifluoro-2-methyl-1-propenyl group, a 3,3,3-trifluoro-1-methyl-1-propenyl group, and a 4,5,5,5-tetrafluoro-4-trifluoromethyl-2-pentenyl group.

The haloalkenyl group having 2-12 carbon atoms represents a group in which at least one hydrogen atom of a straight or branched alkenyl group having 2-12 carbon atoms is substituted with a halogen atom, and examples thereof include a 2-chlorovinyl group, a 2-bromovinyl group, a 2-iodovinyl group, a 1-(chloromethyl)vinyl group, a 1-(trifluoromethyl)vinyl group, a 1-(trifluoromethyl)-2,2-difluorovinyl group, a 3,3-difluoro-2-propenyl group, a 4,4,4-trifluoro-2-butenyl group, a 3,4,4-trifluoro-3-butenyl group, a 3,3-difluoro-2-methyl-2-propenyl group, a 3,3,3-trifluoro-2-methyl-1-propenyl group, a 3,3,3-trifluoro-1-methyl-1-propenyl group, a 3,4,4-trifluoro-1,3-butadienyl group, a 4,4-difluoro-3-methyl-3-butenyl group, a 3,3,4,4,5,5,5-heptafluoro-1-pentenyl group, a 5,5-difluoro-4-pentenyl group, a 4,5,5-trifluoro-4-pentenyl group, a perfluoro-1-butenyl group, a perfluoro-3-butenyl group, a perfluoro-1-pentenyl group, a perfluoro-4-pentenyl group, a perfluoro-1-hexenyl group, a perfluoro-5-hexenyl group, a perfluoro-1-heptenyl group, a perfluoro-6-heptenyl group, a perfluoro-1-octenyl group, a perfluoro-7-octenyl group, a perfluoro-1-nonenyl group, a perfluoro-8-nonenyl group, a perfluoro-1-decenyl group, a perfluoro-9-decenyl group, a perfluoro-1-undecenyl group, a perfluoro-10-undecenyl group, a perfluoro-1-dodecenyl group, and a perfluoro-11-dodecenyl group.

Examples of the alkynyl group having 2-3 carbon atoms include an ethynyl group and a propargyl group.

Examples of the alkynyl group having 2-6 carbon atoms include an ethynyl group, a propargyl group, a 3-butyn-2-yl group, a 2-methyl-3-butyn-2-yl group, a 2-butynyl group, a 3-butynyl group, a 2-pentynyl group, a 3-pentynyl group, a 4-pentynyl group, a 1-hexynyl group, and a 5-hexynyl group.

Examples of the alkynyl group having 2-12 carbon atoms include an ethynyl group, a propargyl group, a 3-butyn-2-yl group, a 2-methyl-3-butyn-2-yl group, a 2-butynyl group, a 3-butynyl group, a 2-pentynyl group, a 3-pentynyl group, a 4-pentynyl group, a 1-hexynyl group, a 5-hexynyl group, a 1-heptynyl group, a 6-heptynyl group, a 1-octynyl group, a 7-octynyl group, a 1-nonynyl group, a 8-nonynyl group, a 1-decynyl group, a 9-decynyl group, a 1-undecynyl group, a 10-undecynyl group, a 1-dodecynyl group, and a 11-dodecynyl group.

The haloalkynyl group having 2-6 carbon atoms represents a group in which at least one hydrogen atom of an alkynyl group having 2-6 carbon atoms is substituted with a halogen atom, and examples thereof include a fluoroethynyl group, a 3-chloro-2-propynyl group, a 3-bromo-2-propynyl group, a 3-iodo-2-propynyl group, a 3-chloro-1-propynyl group, a 5-chloro-4-pentynyl group, a 3,3,3-trifluoro-1-propynyl group, a 3-fluoro-2-propynyl group, a perfluoro-2-butynyl group, a perfluoro-2-pentynyl group, a perfluoro-3-pentynyl group, and a perfluoro-1-hexynyl group.

The haloalkynyl group having 2-12 carbon atoms represents a group in which at least one hydrogen atom of an alkynyl group having 2-12 carbon atoms is substituted with a halogen atom, and examples thereof include a fluoroethynyl group, a 3-chloro-2-propynyl group, a 3-bromo-2-propynyl group, a 3-iodo-2-propynyl group, a 3-chloro-1-propynyl group, a 5-chloro-4-pentynyl group, a 3,3,3-trifluoro-1-propynyl group, a 3,3,3-trifluoro-1-propynyl group, a perfluoro-2-butynyl group, a perfluoro-3-butynyl group, a perfluoro-2-pentynyl group, a perfluoro-3-pentynyl group, a perfluoro-4-pentynyl group, a perfluoro-1-hexynyl group, a perfluoro-5-hexynyl group, a perfluoro-1-heptynyl group, a perfluoro-6-heptynyl group, a perfluoro-1-octynyl group, a perfluoro-7-octynyl group, a perfluoro-1-nonynyl group, a perfluoro-8-nonynyl group, a perfluoro-1-decynyl group, a perfluoro-9-decynyl group, a perfluoro-1-undecynyl group, a perfluoro-10-undecynyl group, a perfluoro-1-dodecynyl group, and a perfluoro-11-dodecynyl group.

Examples of the cycloalkyl group having 3-4 carbon atoms include a cyclopropyl group and a cyclobutyl group.

Examples of the cycloalkyl group having 3-6 carbon atoms include a cyclopropyl group, a cyclobutyl group, a cyclopentyl group, and a cyclohexyl group.

Examples of the cycloalkane ring having 3-6 carbon atoms include a cyclopropane ring, a cyclobutane ring, a cyclopentane ring, and a cyclohexane ring.

Examples of the cycloalkyl group having 3-12 carbon atoms include a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group.

The halocycloalkyl group having 3-12 carbon atoms represents a group in which at least one hydrogen atom of a cycloalkyl group having 3-12 carbon atoms is substituted with a halogen atom, and examples thereof include a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2,3,3-tetrafluorocyclobutyl group, a 2-chlorocyclopentyl group, a 2-chlorocyclohexyl group, a 4,4-difluorocyclohexyl group, a 4-chlorocyclohexyl group, a 2-fluorocycloheptyl group, a 2-fluorocyclooctyl group, a 2-fluorocyclononyl group, a 2-fluorocyclodecyl group, a 2-fluorocycloundecyl group, and a 2-fluorocyclododecyl group.

Examples of the alkoxy group having 1-3 carbon atoms include a methoxy group, an ethoxy group, a propoxy group, and an isopropoxy group.

Examples of the alkoxy group having 1-12 carbon atoms include a methoxy group, an ethoxy group, a propoxy group, an isopropoxy group, a butoxy group, an isobutoxy group, a sec-butoxy group, a tert-butoxy group, a pentyloxy group, an isoamyloxy group, a neopentyloxy group, a 2-pentyloxy group, a 3-pentyloxy group, a 2-methylbutoxy group, a hexyloxy group, an isohexyloxy group, a 3-methylpentyloxy group, and a 4-methylpentyloxy group.

The haloalkoxy group having 1-3 carbon atoms represents a group in which at least one hydrogen atom of an alkyl group having 1-3 carbon atoms is substituted with a halogen atom, and examples thereof include a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a 2,2,2-trifluoroethoxy group, a 2-fluoroethoxy group, a 2-chloroethoxy group, a 2,2-difluoroethoxy group, a 2,2,2-trifluoroethoxy group, a heptafluoropropoxy group, a 3,3,3-trifluoropropoxy group, a 3,3,3-trichloropropoxy group, a 2-fluoropropoxy group, a 3-fluoropropoxy group, a 2,2-difluoropropoxy group, a 2,3-difluoropropoxy group, and a 3,3,3-trifluoropropoxy group.

The haloalkoxy group having 1-12 carbon atoms represents a group in which at least one hydrogen atom of an alkoxy group having 1-12 carbon atoms is substituted with a halogen atom, and examples thereof include a trifluoromethoxy group, a fluoromethoxy group, a difluoromethoxy group, a 2,2,2-trichloroethoxy group, a 2,2,2-trifluoroethoxy group, a 2-fluoroethoxy group, a 2-chloroethoxy group, a 2,2-difluoroethoxy group, a heptafluoropropoxy group, a 3,3,3-trifluoropropoxy group, a 2-fluoropropoxy group, a 3-fluoropropoxy group, a 2,2-difluoropropoxy group, a 2,3-difluoropropoxy group, a 3,3,3-trifluoropropoxy group, a nonafluorobutoxy group, a perfluoropentyloxy group, a perfluorohexyloxy group, a perfluoroheptyloxy group, a perfluorooctyloxy group, a perfluorononyloxy group, a perfluorodecyloxy group, a perfluoroundecyloxy group, and a perfluorododecyloxy group.

Examples of the alkenyloxy group having 2-12 carbon atoms include a vinyloxy group, a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3-butenyloxy group, a 1,2-dimethyl-2-propenyloxy group, a 1,1-dimethyl-2-propenyloxy group, a 2-methyl-2-butenyloxy group, a 3-methyl-2-butenyloxy group, a 2-methyl-3-butenyloxy group, a 3-methyl-3-butenyloxy group, a 1-vinyl-2-propenyloxy group, a 5-hexenyloxy group, a 6-heptenyloxy group, a 7-octenyloxy group, a 8-nonenyloxy group, a 9-decenyloxy group, a 10-undecenyloxy group, and a 11-dodecenyloxy group.

The haloalkenyloxy group having 2-12 carbon atoms represents a group in which at least one hydrogen atom of an alkenyloxy group having 2-12 carbon atoms is substituted with a halogen atom, and examples thereof include a 1-fluorovinyloxy group, a 2-fluorovinyloxy group, a 3,3-difluoro-2-propenyloxy group, a 3,4,4-trifluoro-3-butenyloxy group, a 3,3-difluoro-2-methyl-2-propenyloxy group, a 4,4-difluoro-3-methyl-3-butenyloxy group, a 5,5-difluoro-4-pentenyloxy group, a 4,5,5-trifluoro-4-pentenyloxy group, a 4,4,4-trifluoro-3-methyl-2-butenyloxy group, a 3,5,5-trifluoro-2,4-pentadienyloxy group, a perfluoro-3-butenyloxy group, a perfluoro-4-pentenyloxy group, a perfluoro-5-hexenyloxy group, a perfluoro-6-heptenyloxy group, a perfluoro-7-octenyloxy group, a perfluoro-8-nonenyloxy group, a perfluoro-9-decenyloxy group, a perfluoro-10-undecenyloxy group, and a perfluoro-11-dodecenyloxy group.

Examples of the alkynyloxy group having 2-12 carbon atoms include an ethynyloxy group, a propargyloxy group, a 3-butyn-2-yloxy group, a 2-methyl-3-butyn-2-yloxy group, a 2-butynyloxy group, a 3-butynyloxy group, a 2-pentynyloxy group, a 3-pentynyloxy group, a 4-pentynyloxy group, a 5-hexynyloxy group, a 6-heptynyloxy group, a 7-octynyloxy group, a 8-nonynyloxy group, a 9-decynyloxy group, a 10-undecynyloxy group, and a 11-dodecynyloxy group.

The haloalkynyloxy group having 2-12 carbon atoms represents a group in which at least one hydrogen atom of an alkynyloxy group having 2-12 carbon atoms is substituted with a halogen atom, and examples thereof include a bromoethynyloxy group, a 3-chloro-2-propynyloxy group, a 3-bromo-2-propynyloxy group, a 3-iodo-2-propynyloxy group, a 5-chloro-4-pentynyloxy group, a 3,3,3-trifluoro-1-propynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group, a perfluoro-5-hexynyloxy group, a perfluoro-6-heptynyloxy group, a perfluoro-7-octynyloxy group, a perfluoro-8-nonynyloxy group, a perfluoro-9-decynyloxy group, a perfluoro-10-undecynyloxy group, and a perfluoro-11-dodecynyloxy group.

Examples of the cycloalkyloxy group having 3-12 carbon atoms include a cyclopropyloxy group, a cyclobutyloxy group, a cyclopentyloxy group, a cyclohexyloxy group, a cycloheptyloxy group, a cyclooctyloxy group, a cyclononyloxy group, a cyclodecyloxy group, a cycloundecyloxy group, and a cyclododecyloxy group.

The halocycloalkyloxy group having 3-12 carbon atoms represents a group in which at least one hydrogen atom of a cycloalkyloxy group having 3-12 carbon atoms is substituted with a halogen atom, and examples thereof include a 2-fluorocyclopropyloxy group, a 2,2-difluorocyclopropyloxy group, a 2,2-difluoro-1-methylcyclopropyloxy group, a 2,2-dichloro-1-methylcyclopropyloxy group, a 1-(trifluoromethyl)cyclopropyloxy group, a 2,2,3,3-tetrafluorocyclobutyloxy group, a 4,4-difluorocyclohexyloxy group, a 2-fluorocycloheptyloxy group, a 2-fluorocyclooctyloxy group, a 2-fluorocyclononyloxy group, a 2-fluorocyclodecyloxy group, a 2-fluorocycloundecyloxy group, and a 2-fluorocyclododecyloxy group.

Examples of the cycloalkylthio group having 3-12 carbon atoms include a cyclopropylthio group, a cyclobutylthio group, a cyclopentylthio group, a cyclohexylthio group, a cycloheptylthio group, a cyclooctylthio group, a cyclononylthio group, a cyclodecylthio group, a cycloundecylthio group, and a cyclododecylthio group.

Examples of the alkylthio group having 1-3 carbon atoms include a methylthio group, an ethylthio group, a propylthio group, and an isopropylthio group.

Examples of the alkylthio group having 1-12 carbon atoms include a methylthio group, an ethylthio group, a propylthio group, an isopropylthio group, a butylthio group, an isobutylthio group, a sec-butylthio group, a tert-butylthio group, a pentylthio group, an isopentylthio group, a neo-pentylthio group, an isoamylthio group, a 2-pentylthio group, a 3-pentylthio group, a 2-methylbutylthio group, a hexylthio group, an isohexylthio group, a sec-hexylthio group, a 3-methylpentylthio group, a 4-methylpentylthio group, a heptylthio group, an isoheptylthio group, a sec-heptylthio group, an octylthio group, a 2-ethylhexylthio group, a nonylthio group, a decylthio group, an undecylthio group, and a dodecylthio group.

The haloalkylthio group having 1-3 carbon atoms represents a group in which at least one hydrogen atom of an alkylthio group having 1-3 carbon atoms is substituted with a halogen atom, and examples thereof include a fluoromethylthio group, a bromodifluoromethylthio group, a difluoromethylthio group, a trifluoromethylthio group, a pentafluoroethylthio group, a 2,2,2-trifluoroethylthio group, a 2,2-difluoroethylthio group, a heptafluoropropylthio group, a 3,3,3-trifluoropropylthio group, or a 2,2-difluoropropylthio group.

The haloalkylthio group having 1-12 carbon atoms represents a group in which at least one hydrogen atom of an alkylthio group having 1-12 carbon atoms is substituted with a halogen atom, and examples thereof include a fluoromethylthio group, a bromodifluoromethylthio group, a difluoromethylthio group, a trifluoromethylthio group, a pentafluoroethylthio group, a 2,2,2-trifluoroethylthio group, a 2,2-difluoroethylthio group, a heptafluoropropylthio group, a 3,3,3-trifluoropropylthio group, a 2,2-difluoropropylthio group, a nonafluorobutylthio group, a perfluoropentylthio group, a perfluorohexylthio group, a perchlorohexylthio group, a perfluoroheptylthio group, a perfluorooctylthio group, a perfluorononylthio group, a perfluorodecylthio group, a perchlorodecylthio group, a perbromodecylthio group, a perfluoroundecylthio group, and a perfluorododecylthio group.

Examples of the alkenylthio group having 2-12 carbon atoms include a vinylthio group, a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 1,2-dimethyl-2-propenylthio group, a 1,1-dimethyl-2-propenylthio group, a 2-methyl-2-butenylthio group, a 3-methyl-2-butenylthio group, a 2-methyl-3-butenylthio group, a 3-methyl-3-butenylthio group, a 1-vinyl-2-propenylthio group, a 5-hexenylthio group, a 6-heptenylthio group, a 7-octenylthio group, a 8-nonenylthio group, a 9-decenylthio group, a 10-undecenylthio group, and a 11-dodecenylthio group.

The haloalkenylthio group having 2-12 carbon atoms represents a group in which at least one hydrogen atom of an alkenylthio group having 2-12 carbon atoms is substituted with a halogen atom, and examples thereof include a 1-fluorovinylthio group, a 2-fluorovinylthio group, a 3,3-difluoro-2-propenylthio group, a 4,4,4-trifluoro-2-butenylthio group, a 3,4,4-trifluoro-3-butenylthio group, a 3,3-difluoro-2-methyl-2-propenylthio group, a 4,4-difluoro-3-methyl-3-butenylthio group, a 5,5-difluoro-4-pentenylthio group, a 4,5,5-trifluoro-4-pentenylthio group, a 4,4,4-trifluoro-3-methyl-2-butenylthio group, a 3,5,5-trifluoro-2,4-pentadienylthio group, a 4,4,5,5,6,6-heptafluoro-2-hexenylthio group, a 4,5,5,5-tetrafluoro-4-trifluoromethyl-2-pentenylthio group, a perfluoro-3-butenylthio group, a perfluoro-4-pentenylthio group, a perfluoro-5-hexenylthio group, a perfluoro-6-heptenylthio group, a perfluoro-7-octenylthio group, a perfluoro-8-nonenylthio group, a perfluoro-9-decenylthio group, a perfluoro-10-undecenylthio group, and a perfluoro-11-dodecenylthio group.

Examples of the alkynylthio group having 2-12 carbon atoms include an ethynylthio group, a propargylthio group, a 3-butyn-2-ylthio group, a 2-methyl-3-butyn-2-ylthio group, a 2-butynylthio group, a 3-butynylthio group, a 2-pentynylthio group, a 3-pentynylthio group, a 4-pentynylthio group, a 5-hexynylthio group, a 6-heptynylthio group, a 7-octynylthio group, a 8-nonynylthio group, a 9-decynylthio group, a 10-undecynylthio group, and a 11-dodecynylthio group.

The haloalkynylthio group having 2-12 carbon atoms represents a group in which at least one hydrogen atom of an alkynylthio group having 2-12 carbon atoms is substituted with a halogen atom, and examples thereof include a bromoethynylthio group, a 3-chloro-2-propynylthio group, a 3-bromo-2-propynylthio group, a 3-iodo-2-propynylthio group, a 5-chloro-4-pentynylthio group, a 3,3,3-trifluoro-1-propynylthio group, a perfluoro-2-butynylthio group, a perfluoro-3-butynylthio group, a perfluoro-2-pentynylthio group, a perfluoro-3-pentynylthio group, a perfluoro-4-pentynylthio group, a perfluoro-5-hexynylthio group, a perfluoro-6-heptynylthio group, a perfluoro-7-octynylthio group, a perfluoro-8-nonynylthio group, a perfluoro-9-decynylthio group, a perfluoro-10-undecynylthio group, and a perfluoro-11-dodecynylthio group.

The alkylcarbonyl group having 2-12 carbon atoms has the total number of carbon atoms including carbon of carbonyl within a range of 2 to 12, and examples thereof include an acetyl group, a propionyl group, a butanoyl group, a pentanoyl group, a hexanoyl group, a heptanoyl group, an octanoyl group, a nonanoyl group, a decanoyl group, an undecanoyl group, and a dodecanoyl group.

The haloalkylcarbonyl group having 2-12 carbon atoms represents a group in which at least one hydrogen atom of an alkylcarbonyl group having 2-12 carbon atoms is substituted with a halogen atom, and examples thereof include a trichloroacetyl group, a fluoroacetyl group, a difluoroacetyl group, a trifluoroacetyl group, a pentafluoropropionyl group, a 3-fluoropropionyl group, and a 3,3,3-trifluoropropionyl group.

The alkylcarbonyloxy group having 2-12 carbon atoms has the total number of carbon atoms including carbon of carbonyl within a range of 2 to 12, and examples thereof include an acetoxy group, a propionyloxy group, an isopropionyloxy group, and a butanoyloxy group.

The alkylcarbonylthio group having 2-12 carbon atoms has the total number of carbon atoms including carbon of carbonyl within a range of 2 to 12, and examples thereof include an acetylthio group, a propionylthio group, an isopropionylthio group, and a butanoylthio group.

The alkoxycarbonyl group having 2-6 carbon atoms represents a group in which the total number of carbon atoms including carbon of carbonyl is within a range of 2 to 6, and examples thereof include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, and a pentyloxycarbonyl group.

The alkoxycarbonyl group having 2-12 carbon atoms has the total number of carbon atoms including carbon of carbonyl within a range of 2 to 12, and examples thereof include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, a hexyloxycarbonyl group, a heptyloxycarbonyl group, an octyloxycarbonyl group, a nonyloxycarbonyl group, a decyloxycarbonyl group, an undecyloxycarbonyl group, and a dodecyloxycarbonyl group.

Examples of the trialkylsilyl group having 3-12 carbon atoms include a trimethylsilyl group, a tert-butyldimethylsilyl group, a triethylsilyl group, an isopropyldimethylsilyl group, a triisopropylsilyl group, a tri(tert-butyl)silyl group, and a tributylsilyl group.

The trialkylsilylethynyl group having 5-14 carbon atoms represents an ethynyl group to which a trialkylsilyl group is attached, and also has total number of carbon atoms including carbon of an ethynyl group within a range of 5 to 14, three alkyl groups on the silyl group being the same or different to each other, and examples thereof include a trimethylsilylethynyl group, a tert-butyldimethylsilylethynyl group, a triethylsilylethynyl group, an isopropyldimethylsilylethynyl group, a triisopropylsilylethynyl group, a tri(tert-butyl)silylethynyl group, and a tributylsilylethynyl group.

Examples of the alkylsulfonyl group having 1-12 carbon atoms include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, an isopentylsulfonyl group, a neopentylsulfonyl group, an isoamylsulfonyl group, a 2-pentylsulfonyl group, a 3-pentylsulfonyl group, a 2-methylbutylsulfonyl group, a hexylsulfonyl group, an isohexylsulfonyl group, a sec-hexylsulfonyl group, a 3-methylpentylsulfonyl group, a 4-methylpentylsulfonyl group, a heptylsulfonyl group, an isoheptylsulfonyl group, a sec-heptylsulfonyl group, an octylsulfonyl group, a 2-ethylhexylsulfonyl group, a nonylsulfonyl group, a decylsulfonyl group, an undecylsulfonyl group, and a dodecylsulfonyl group.

The haloalkylsulfonyl group having 1-12 carbon atoms represents a group in which at least one hydrogen atom of an alkylsulfonyl group having 1-12 carbon atoms is substituted with a halogen atom, and examples thereof include a fluoromethylsulfonyl group, a bromodifluoromethylsulfonyl group, a difluoromethylsulfonyl group, a trifluoromethylsulfonyl group, a trichloromethylsulfonyl group and a 2,2,2-trifluoroethylsulfonyl group.

Examples of the alkylsulfinyl group having 1-12 carbon atoms include a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, and a pentylsulfinyl group.

The haloalkylsulfinyl group having 1-12 carbon atoms represents a group in which at least one hydrogen atom of an alkylsulfinyl group having 1-12 carbon atoms is substituted with a halogen atom, and examples thereof include a fluoromethylsulfinyl group, a difluoromethylsulfinyl group, a trifluoromethylsulfinyl group, a trichloromethylsulfinyl group, a tribromomethylsulfinyl group, a pentafluoroethylsulfinyl group, a 2,2,2-trichloroethylsulfinyl group, a 2-fluoroethylsulfinyl group, and a 2,2,2-trifluoroethylsulfinyl group.

The aminosulfonyl group which optionally has an alkyl group having 1-12 carbon atoms is an amino group in which one or two hydrogen atoms of an aminosulfonyl group are optionally substituted with an alkyl group and, when the total number of carbon atoms of the alkyl group is within a range of 1 to 12 and the number of alkyl groups is 2 or more, those groups may be the same or different to each other. Examples of the aminosulfonyl group which optionally has an alkyl group having 1-12 carbon atoms include an aminosulfonyl group, a methylaminosulfonyl group, an ethylaminosulfonyl group, a propylaminosulfonyl group, an isopropylaminosulfonyl group, a butylaminosulfonyl group, a dimethylaminosulfonyl group, a diethylaminosulfonyl group, a dipropylaminosulfonyl group, a diisopropylaminosulfonyl group, an ethyl(methyl)aminosulfonyl group, and a propyl(methyl)aminosulfonyl group.

The amino group which optionally has an alkyl group having 1-12 carbon atoms is an amino group in which one or two hydrogen atoms of an amino group are optionally substituted with an alkyl group and, when the total number of carbon atoms of the alkyl group is within a range of 1 to 12 and the number of alkyl groups is 2 or more, those groups may be the same or different to each other. Examples of the amino group which optionally has an alkyl group having 1-12 carbon atoms include an amino group, a methylamino group, an ethylamino group, a propylamino group, an isopropylamino group, a butylamino group, a pentylamino group, a hexylamino group, a heptylamino group, an octylamino group, a nonylamino group, a decylamino group, an undecylamino group, a dodecylamino group, a dimethylamino group, a diethylamino group, a dipropylamino group, a diisopropylamino group, a dibutylamino group, an ethyl(methyl)amino group, a propyl(methyl)amino group, a butyl(methyl)amino group, a pentyl(methyl)amino group, a hexyl(methyl)amino group, a heptyl(methyl)amino group, an octyl(methyl)amino group, a nonyl(methyl)amino group, a decyl(methyl)amino group, and an undecyl(methyl)amino group.

The aminocarbonyl group which optionally has an alkyl group having 1-12 carbon atoms represents a group in which the total number of carbon atoms including carbon of carbonyl is within a range of 1 to 12 and one or two hydrogen atoms of an aminocarbonyl group are optionally substituted with an alkyl group and, when the number of alkyl groups is 2 or more, those groups may be the same or different to each other. Examples of the aminocarbonyl group which optionally has an alkyl group having 1-12 carbon atoms include an aminocarbonyl group, a methylaminocarbonyl group, an ethylaminocarbonyl group, a propylaminocarbonyl group, an isopropylaminocarbonyl group, a butylaminocarbonyl group, a dimethylaminocarbonyl group, a diethylaminocarbonyl group, a dipropylaminocarbonyl group, a diisopropylaminocarbonyl group, an ethyl(methyl)aminocarbonyl group, and a propyl(methyl)aminocarbonyl group.

Examples of the aryl group having 6-16 carbon atoms include a phenyl group, a 1-naphthyl group, and a 2-naphthyl group.

The haloaryl group having 6-16 carbon atoms represents a group in which at least one hydrogen atom of an aryl group having 6-16 carbon atoms is substituted with a halogen atom, and examples thereof include a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,4-difluorophenyl group, a 2,5-difluorophenyl group, a 2,6-difluorophenyl group, a 3,5-difluorophenyl group, a 2,4-dichlorophenyl group, a 2,5-dichlorophenyl group, a 2,6-dichlorophenyl group, a 3,5-dichlorophenyl group, a 2,4,6-trifluorophenyl group, a 2,3,4-trifluorophenyl group, a 2,4,5-trifluorophenyl group, a 3,4,5-trifluorophenyl group, and a 2,4,6-trichlorophenyl group.

Examples of the aryloxy group having 6-16 carbon atoms include a phenyloxy group, a 1-naphthyloxy group, and a 2-naphthyloxy group.

The haloaryloxy group having 6-16 carbon atoms represents a group in which at least one hydrogen atom of an aryloxy group having 6-16 carbon atoms is substituted with a halogen atom, and examples thereof include a 2-fluorophenoxy group, a 3-fluorophenoxy group, a 4-fluorophenoxy group, a 2-chlorophenoxy group, a 4-fluorophenoxy group, a 2-chlorophenoxy group, a 4-fluorophenoxy group, a 4-fluorophenoxy group, a 4-fluorophenoxy group, a 2-chlorophenoxy group, a 4-fluorophenoxy group, a 4-fluorophenoxy group, a 2-chlorophenoxy group, a 4-fluorophenoxy group, a 2-chlorophenoxy group, a 4-fluorophenoxy group, a 2-chlorophenoxy group, a 4-fluorophenoxy group, a 2-chlorophenoxy group, a 4-fluorophenoxy group, a 2-chlorophenoxy group, a 4-fluorophenoxy group, a 2-chlorophenoxy group, a 4-fluorophenoxy group, a 2-chlorophenoxy group, a 4-fluorophenoxy group, a 2-chlorophenoxy group, a 3-chlorophenoxy group, a 4-fluorophenoxy group, a 2-chlorophenoxy group, a 3-chlorophenoxy group, a 3-chlorophenoxy group, a 3-chlorophenoxy group, a 2-chlorophenoxy group, a 3-chlorophenoxy group, a 3-chlorophenoxy group, a 3-chlorophenoxy group, a 3-chlorophenoxy group, a 3-chlorophenoxy group, a 3-chlorophenoxy group, a 2-chlorophenoxy group, a 3-chlorophenoxy group, a 2-chlorophenoxy group, a 3-chlorophenoxy group, a 3-chlorophenoxy group, a 2-chlorophenoxy group, a 3-chlorophenoxy group, a 2-chlorophenoxy group, a 3-chlorophenoxy group, a 3-chlorophenoxy group, a 3-chlorophenoxy group, a 4-chlorophenoxy group, a 2-bromophenoxy group, a 3-bromophenoxy group, a 4-bromophenoxy group, a 2-iodophenoxy group, a 3-iodophenoxy group, a 4-iodophenoxy group, a 2,4-difluorophenoxy group, a 2,5-difluorophenoxy group, a 2,6-difluorophenoxy group, a 3,5-difluorophenoxy group, a 2,4-dichlorophenoxy group, a 2,5-dichlorophenoxy group, a 2,6-dichlorophenoxy group, a 3,5-dichlorophenoxy group, a 2,4,6-trifluorophenoxy group, a 2,3,4-trifluorophenoxy group, and a 2,4,5-trifluorophenoxy group.

Examples of the arylthio group having 6-16 carbon atoms include a phenylthio group, a 1-naphthylthio group, and a 2-naphthylthio group.

The haloarylthio group having 6-16 carbon atoms represents a group in which at least one hydrogen atom of an arylthio group having 6-16 carbon atoms is substituted with a halogen atom, and examples thereof include a 2-fluorophenylthio group, a 3-fluorophenylthio group, a 4-fluorophenylthio group, a 2-chlorophenylthio group, a 3-chlorophenylthio group, a 4-chlorophenylthio group, a 2-bromophenylthio group, a 3-bromophenylthio group, a 4-bromophenylthio group, a 2-iodophenylthio group, a 3-iodophenylthio group, a 4-iodophenylthio group, a 2,4-difluorophenylthio group, a 2,5-difluorophenylthio group, a 2,6-difluorophenylthio group, a 3,5-difluorophenylthio group, a 2,4-dichlorophenylthio group, a 2,5-dichlorophenylthio group, a 2,6-dichlorophenylthio group, a 3,5-dichlorophenylthio group, a 2,4,6-trifluorophenylthio group, a 2,3,4-trifluorophenylthio group, and a pentafluorophenylthio group.

The aralkyl group having 7-18 carbon atoms represents a group in which the total number of carbon atoms of the alkyl moiety and the aryl moiety is within a range of 7 to 18, and examples thereof include a benzyl group, a phenethyl group, a 3-phenylpropyl group, a 4-phenylbutyl group, a 5-phenylpentyl group, a 1-naphthylmethyl group, a 2-(1-naphthyl)ethyl group, a 3-(1-naphthyl)propyl group, a 4-(1-naphthyl)butyl group, a 5-(1-naphthyl)pentyl group, a 6-(1-naphthyl)hexyl group, a 7-(1-naphthyl)heptyl group, a 8-(1-naphthyl)octyl group, a 2-naphthylmethyl group, a 2-(2-naphthyl)ethyl group, a 3-(2-naphthyl)propyl group, and a 4-(2-naphthyl)butyl group.

The haloaralkyl group having 7-18 carbon atoms represents a group in which at least one hydrogen atom of the aryl moiety and/or the alkyl moiety of an aralkyl group having 7-18 carbon atoms is substituted with a halogen atom, and examples thereof include a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, a 2-iodobenzyl group, a 3-iodobenzyl group, a 4-iodobenzyl group, a 2-(4-fluorophenyl)ethyl group, a 2-(4-chlorophenyl)ethyl group, a 2-(4-bromophenyl)ethyl group, a 2-(4-iodophenyl)ethyl group, a 3-(4-fluorophenyl)propyl group, a 3-(4-chlorophenyl)propyl group, a 3-(4-bromophenyl)propyl group, a 3-(4-iodophenyl)propyl group, a difluoro(phenyl)methyl group, a difluoro(4-fluorophenyl)methyl group, a difluoro(4-chlorophenyl)methyl group, a difluoro(4-bromophenyl)methyl group, and a difluoro(4-iodophenyl)methyl group.

The arylalkoxy group having 7-18 carbon atoms represents a group in which the total number of carbon atoms of the aryl moiety and the alkoxy moiety is within a range of 7 to 18, and examples of the arylalkoxy group having 7-18 carbon atoms include a benzyloxy group, a phenethyloxy group, a 3-phenylpropoxy group, a 4-phenylbutoxy group, a 2-(1-naphthyl)ethyloxy group, a 3-(1-naphthyl)propoxy group, a 4-(1-naphthyl)butoxy group, a 5-(1-naphthyl)pentyloxy group, a 6-(1-naphthyl)hexyloxy group, a 7-(1-naphthyl)heptyloxy group, a 8-(1-naphthyl)octyloxy group, a 2-naphthylmethyloxy group, a 2-(2-naphthyl)ethyloxy group, a 3-(2-naphthyl)propoxy group, and a 4-(2-naphthyl)butoxy group.

The haloarylalkoxy group having 7-18 carbon atoms represents a group in which at least one hydrogen atom of the aryl moiety and/or the alkyl moiety of an arylalkoxy group having 7-18 carbon atoms is substituted with a halogen atom, and examples thereof include a 2-fluorobenzyloxy group, a 3-fluorobenzyloxy group, a 4-fluorobenzyloxy group, a 2-chlorobenzyloxy group, a 3-chlorobenzyloxy group, a 4-chlorobenzyloxy group, a 2-bromobenzyloxy group, a 3-bromobenzyloxy group, a 4-bromobenzyloxy group, a 2-iodobenzyloxy group, a 3-iodobenzyloxy group, a 4-iodobenzyloxy group, a difluoro(phenyl)methoxy group, a difluoro(4-fluorophenyl)methoxy group, a difluoro(4-chlorophenyl)methoxy group, a difluoro(4-bromophenyl)methoxy group, and a difluoro(4-iodophenyl)methoxy group.

Examples of the arylsulfinyl group having 6-16 carbon atoms include a phenylsulfinyl group, a 1-naphthylsulfinyl group, and a 2-naphthylsulfinyl group.

The haloarylsulfinyl group having 6-16 carbon atoms represents a group in which at least one hydrogen atom of an arylsulfinyl group having 6-16 carbon atoms is substituted with a halogen atom, and examples thereof include a 2-fluorophenylsulfinyl group, a 3-fluorophenylsulfinyl group, a 4-fluorophenylsulfinyl group, a 2-chlorophenylsulfinyl group, a 3-chlorophenylsulfinyl group, a 4-chlorophenylsulfinyl group, a 2-bromophenylsulfinyl group, a 3-bromophenylsulfinyl group, a 4-bromophenylsulfinyl group, a 2-iodophenylsulfinyl group, a 3-iodophenylsulfinyl group, a 4-iodophenylsulfinyl group, a 2,4-difluorophenylsulfinyl group, a 2,5-difluorophenylsulfinyl group, a 2,6-difluorophenylsulfinyl group, a 3,5-difluorophenylsulfinyl group, a 2,4-dichlorophenylsulfinyl group, a 2,5-dichlorophenylsulfinyl group, a 2,6-dichlorophenylsulfinyl group, a 3,5-dichlorophenylsulfinyl group, a 2,4,6-trifluorophenylsulfinyl group, a 2,3,4-trifluorophenylsulfinyl group, a 2,4,5-trifluorophenylsulfinyl group, and a 3,4,5-trifluorophenylsulfinyl group.

The polyoxalkyloxy group having 2-11 carbon atoms is a group in which one methylene group of a straight alkoxy group having 3 carbon atoms is substituted with an oxygen atom, a group in which one or two methylene groups of a straight alkoxy group having 4 carbon atoms is substituted with an oxygen atom, or a group in which one, two, or three methylene groups of a straight alkoxy group having 5-12 carbon atoms is substituted with an oxygen atom, and the oxygen atoms are not adjacent to each other, and examples thereof include an —O—CH$_2$—O—CH$_3$ group, an —O—CH$_2$—O—CH$_2$—CH$_3$ group, an —O—(CH$_2$)$_2$—O—CH$_3$ group, and an —O—(CH$_2$)$_2$—O—CH$_2$—CH$_3$ group.

The oxacycloalkyloxy group having 2-5 carbon atoms is a group in which one methylene group in a ring of a cycloalkyloxy group having 3-6 carbon atoms is substituted with an oxygen atom, and examples thereof include an oxiranyloxy group, an oxetanyloxy group, a tetrahydrofuranyloxy group, and a tetrahydropyranyloxy group.

The aminocarbonyl group which optionally has an alkyl group having 1-12 carbon atoms and/or an aryl group having 6-12 carbon atoms represents a group in which one or two hydrogen atoms of an aminocarbonyl group are optionally substituted with an alkyl group having 1-12 carbon atoms and/or an aryl group having 6-12 carbon atoms, and substituents on the nitrogen atom may be the same or different to each other. Examples of the aminocarbonyl group which optionally has an alkyl group having 1-12 carbon atoms and/or an aryl group having 6-12 carbon atoms include an aminocarbonyl group, an N-methylaminocarbonyl group, an N-ethylaminocarbonyl group, an N-propylaminocarbonyl group, an N,N-dimethylaminocarbonyl group, an N,N-diethylaminocarbonyl group, an N,N-dipropylaminocarbonyl group, an N,N-diisopropylaminocarbonyl group, an N-ethyl-N-methylaminocarbonyl group, an N-propyl-N-methylaminocarbonyl group, an N-phenylaminocarbonyl group, an N-methyl-N-phenylaminocarbonyl group, and an N-ethyl-N-phenylaminocarbonyl group.

The aminosulfonyl group which optionally has an alkyl group having 1-12 carbon atoms and/or an aryl group having 6-12 carbon atoms represents a group in which one or two hydrogen atoms of an aminosulfonyl group are optionally substituted with an alkyl group having 1-12 carbon atoms and/or an aryl group having 6-12 carbon atoms, and substituents on the nitrogen atom may be the same or different to each other. Examples of the aminosulfonyl group which optionally has an alkyl group having 1-12 carbon atoms and/or an aryl group having 6-12 carbon atoms include an aminosulfonyl group, an N-methylaminosulfonyl group, an N-ethylaminosulfonyl group, an N-propylaminosulfonyl group, an N-isopropylaminosulfonyl group, an N,N-dimethylaminosulfonyl group, an N,N-diethylaminosulfonyl group, an N,N-dipropylaminosulfonyl group, an N,N-diisopropylaminosulfonyl group, an N-phenylaminosulfonyl group, an N-methyl-N-phenylaminosulfonyl group, an N-ethyl-N-phenylaminosulfonyl group, and an N-propyl-N-phenylaminosulfonyl group.

The amino group which optionally has an alkyl group having 1-12 carbon atoms and/or an aryl group having 6-12 carbon atoms represents a group in which one or two hydrogen atoms of an amino group are optionally substituted with an alkyl group having 1-12 carbon atoms and/or an aryl group having 6-12 carbon atoms, and substituents on the nitrogen atom may be the same or different to each other. Examples of the amino group which optionally has an alkyl group having 1-12 carbon atoms and/or an aryl group having 6-12 carbon atoms include an amino group, an N-methylamino group, an N-ethylamino group, an N-propylamino group, an N-isopropylamino group, an N,N-dimethylamino group, an N,N-diethylamino group, an N,N-dipropylamino group, an N,N-diisopropylamino group, an N-phenylamino group, an N-methyl-N-phenylamino group, an N-ethyl-N-phenylamino group, and an N-propyl-N-phenylamino group.

Examples of the arylsulfonyl group having 6-16 carbon atoms include a phenylsulfonyl group, a 1-naphthylsulfonyl group, a 2-naphthylsulfonyl group, a 1-acenaphthylsulfonyl group, a 1-phenanthrylsulfonyl group, a 9-anthrylsulfonyl group, and a 1-pyrenylsulfonyl group.

The haloarylsulfonyl group having 6-16 carbon atoms represents a group in which at least one hydrogen atom of an arylsulfonyl group having 6-16 carbon atoms is substituted with a halogen atom, and examples thereof include a 2-fluorophenylsulfonyl group, a 3-fluorophenylsulfonyl group, a 4-fluorophenylsulfonyl group, a 2-chlorophenylsulfonyl group, a 3-chlorophenylsulfonyl group, a 4-chlorophenylsulfonyl group, a 2-bromophenylsulfonyl group, a 3-bromophenylsulfonyl group, a 4-bromophenylsulfonyl group, a 2-iodophenylsulfonyl group, a 3-iodophenylsulfonyl group, a 4-iodophenylsulfonyl group, a 4-fluoro-1-naphthylsulfonyl group, a 4-chloro-1-naphthylsulfonyl group, a 3-fluoro-1-acenaphthylsulfonyl group, a 9-fluoro-1-phenanthrylsulfonyl group, a 10-fluoro-9-anthrylsulfonyl group, and a 6-fluoro-1-pyrenylsulfonyl group.

Examples of the aspect of the present compound include compounds in which a substituent in formula (1) is as following.

A tetrazolinone compound in which Y is an oxygen atom.
A tetrazolinone compound in which Y is a sulfur atom.
A tetrazolinone compound in which Q is an oxygen atom.
A tetrazolinone compound in which Q is a sulfur atom. A tetrazolinone compound in which Q is an NR$^{11}$ group.

A tetrazolinone compound in which Y and Q are oxygen atoms. A tetrazolinone compound in which Y is an oxygen atom and Q is a sulfur atom. A tetrazolinone compound in which Y is an oxygen atom and Q is an NR$^{11}$ group. A tetrazolinone compound in which Y is a sulfur atom and Q is an oxygen atom. A tetrazolinone compound in which Y and Q are sulfur atoms. A tetrazolinone compound in which Y is a sulfur atom and Q is an $NR^{11}$ group.

A tetrazolinone compound in which E is E1. A tetrazolinone compound in which E is E2. A tetrazolinone compound in which E is E3. A tetrazolinone compound in which E is E4. A tetrazolinone compound in which E is E5. A tetrazolinone compound in which E is E6. A tetrazolinone compound in which E is E7. A tetrazolinone compound in which E is E8. A tetrazolinone compound in which E is E9. A tetrazolinone compound in which E is E10. A tetrazolinone compound in which E is E11. A tetrazolinone compound in which E is E12. A tetrazolinone compound in which E is E13. A tetrazolinone compound in which E is E14. A tetrazolinone compound in which E is E15. A tetrazolinone compound in which E is E16. A tetrazolinone compound in which E is E17. A tetrazolinone compound in which E is E18. A tetrazolinone compound in which E is E19. A tetrazolinone compound in which E is E20. A tetrazolinone compound in which E is E21. A tetrazolinone compound in which E is E22. A tetrazolinone compound in which E is E23. A tetrazolinone compound in which E is E34. A tetrazolinone compound in which E is E25. A tetrazolinone compound in which E is E36. A tetrazolinone compound in which E is E37. A tetrazolinone compound in which E is E38. A tetrazolinone compound in which E is E29. A tetrazolinone compound in which E is E30. A tetrazolinone compound in which E is E31. A tetrazolinone compound in which E is E32. A tetrazolinone compound in which E is E33. A tetrazolinone compound in which E is E34. A tetrazolinone compound in which E is E35. A tetrazolinone compound in which E is E36. A tetrazolinone compound in which E is E37. A tetrazolinone compound in which E is E38. A tetrazolinone compound in which E is E39. A tetrazolinone compound in which E is E40. A tetrazolinone compound in which E is E41. A tetrazolinone compound in which E is E42. A tetrazolinone compound in which E is E43. A tetrazolinone compound in which E is E44. A tetrazolinone compound in which E is E45. A tetrazolinone compound in which E is E46.

A tetrazolinone compound in which $R^4$, $R^5$, $R^7$, $R^8$, and $R^9$ are hydrogen atoms; $R^{10}$ is a methyl group; and Q and Y are oxygen atoms. A tetrazolinone compound in which $R^4$, $R^5$, $R^7$, $R^8$, and $R^9$ are hydrogen atoms; $R^{10}$ is a methyl group; Q is an oxygen atom; and Y is a sulfur atom. A tetrazolinone compound in which E is E1; $R^4$, $R^5$, $R^7$, $R^8$, and $R^9$ are hydrogen atoms; $R^{10}$ is a methyl group; and Q and Y are oxygen atoms. A tetrazolinone compound in which E is E2; $R^4$, $R^5$, $R^7$, $R^8$, and $R^9$ are hydrogen atoms; $R^{10}$ is a methyl group; and Q and Y are oxygen atoms. A tetrazolinone compound in which E is E3; $R^4$, $R^5$, $R^7$, $R^8$, and $R^9$ are hydrogen atoms; $R^{10}$ is a methyl group; and Q and Y are oxygen atoms. A tetrazolinone compound in which E is E4; $R^4$, $R^5$, $R^7$, $R^8$, and $R^9$ are hydrogen atoms; $R^{10}$ is a methyl group; and Q and Y are oxygen atoms. A tetrazolinone compound in which E is E5; $R^4$, $R^5$, $R^7$, $R^8$, and $R^9$ are hydrogen atoms; $R^{10}$ is a methyl group; and Q and Y are oxygen atoms. A tetrazolinone compound in which E is E6; $R^4$, $R^5$, $R^7$, $R^8$, and $R^9$ are hydrogen atoms; $R^{10}$ is a methyl group; and Q and Y are oxygen atoms. A tetrazolinone compound in which E is E7; $R^4$, $R^5$, $R^7$, $R^8$, and $R^9$ are hydrogen atoms; $R^{10}$ is a methyl group; and Q and Y are oxygen atoms. A tetrazolinone compound in which E is E8; $R^4$, $R^5$, $R^7$, $R^8$, and $R^9$ are hydrogen atoms; $R^{10}$ is a methyl group; and Q and Y are oxygen atoms. A tetrazolinone compound in which E is E9; $R^4$, $R^5$, $R^7$, $R^8$, and $R^9$ are hydrogen atoms; $R^{10}$ is a methyl group; and Q and Y are oxygen atoms. A tetrazolinone compound in which E is E10; $R^4$, $R^5$, $R^7$, $R^8$, and $R^9$ are hydrogen atoms; $R^{10}$ is a methyl group; and Q and Y are oxygen atoms.

A tetrazolinone compound in which E is E11; $R^4$, $R^5$, $R^7$, $R^8$, and $R^9$ are hydrogen atoms; $R^{10}$ is a methyl group; and Q and Y are oxygen atoms. A tetrazolinone compound in which E is E12; $R^4$, $R^5$, $R^7$, $R^8$, and $R^9$ are hydrogen atoms; $R^{10}$ is a methyl group; and Q and Y are oxygen atoms. A tetrazolinone compound in which E is E13; $R^4$, $R^5$, $R^7$, $R^8$, and $R^9$ are hydrogen atoms; $R^{10}$ is a methyl group; and Q and Y are oxygen atoms. A tetrazolinone compound in which E is E14; $R^4$, $R^5$, $R^7$, $R^8$, and $R^9$ are hydrogen atoms; $R^{10}$ is a methyl group; and Q and Y are oxygen atoms. A tetrazolinone compound in which E is E15; $R^4$, $R^5$, $R^7$, $R^8$, and $R^9$ are hydrogen atoms; $R^{10}$ is a methyl group; and Q and Y are oxygen atoms. A tetrazolinone compound in which E is E16; $R^4$, $R^5$, $R^7$, $R^8$, and $R^9$ are hydrogen atoms; $R^{10}$ is a methyl group; and Q and Y are oxygen atoms. A tetrazolinone compound in which E is E17; $R^4$, $R^5$, $R^7$, $R^8$, and $R^9$ are hydrogen atoms; $R^{10}$ is a methyl group; and Q and Y are oxygen atoms. A tetrazolinone compound in which E is E18; $R^4$, $R^5$, $R^7$, $R^8$, and $R^9$ are hydrogen atoms; $R^{10}$ is a methyl group; and Q and Y are oxygen atoms. A tetrazolinone compound in which E is E19; $R^4$, $R^5$, $R^7$, $R^8$, and $R^9$ are hydrogen atoms; $R^{10}$ is a methyl group; and Q and Y are oxygen atoms. A tetrazolinone compound in which E is E20; $R^4$, $R^5$, $R^7$, $R^8$, and $R^9$ are hydrogen atoms; $R^{10}$ is a methyl group; and Q and Y are oxygen atoms.

A tetrazolinone compound in which E is E21; $R^4$, $R^5$, $R^7$, $R^8$, and $R^9$ are hydrogen atoms; $R^{10}$ is a methyl group; and Q and Y are oxygen atoms. A tetrazolinone compound in which E is E22; $R^4$, $R^5$, $R^7$, $R^8$, and $R^9$ are hydrogen atoms; $R^{10}$ is a methyl group; and Q and Y are oxygen atoms. A tetrazolinone compound in which E is. E23; $R^4$, $R^5$, $R^7$, $R^8$, and $R^9$ are hydrogen atoms; $R^{10}$ is a methyl group; and Q and Y are oxygen atoms. A tetrazolinone compound in which E is E24; $R^4$, $R^5$, $R^7$, $R^8$, and $R^9$ are hydrogen atoms; $R^{10}$ is a methyl group; and Q and Y are oxygen atoms. A tetrazolinone compound in which E is E25; $R^4$, $R^5$, $R^7$, $R^8$, and $R^9$ are hydrogen atoms; $R^{10}$ is a methyl group; and Q and Y are oxygen atoms. A tetrazolinone compound in which E is E26; $R^4$, $R^5$, $R^7$, $R^8$, and $R^9$ are hydrogen atoms; $R^{10}$ is a methyl group; and Q and Y are oxygen atoms. A tetrazolinone compound in which E is E27; $R^4$, $R^5$, $R^7$, $R^8$, and $R^9$ are hydrogen atoms; $R^{10}$ is a methyl group; and Q and Y are oxygen atoms. A tetrazolinone compound in which E is E28; $R^4$, $R^5$, $R^7$, $R^8$, and $R^9$ are hydrogen atoms; $R^{10}$ is a methyl group; and Q and Y are oxygen atoms. A tetrazolinone compound in which E is E29; $R^4$, $R^5$, $R^7$, $R^8$, and $R^9$ are hydrogen atoms; $R^{10}$ is a methyl group; and Q and Y are oxygen atoms. A tetrazolinone compound in which E is E30; $R^4$, $R^5$, $R^7$, $R^8$, and $R^9$ are hydrogen atoms; $R^{10}$ is a methyl group; and Q and Y are oxygen atoms.

A tetrazolinone compound in which E is E31; $R^4$, $R^5$, $R^7$, $R^8$, and $R^9$ are hydrogen atoms; $R^{10}$ is a methyl group; and Q and Y are oxygen atoms. A tetrazolinone compound in which E is E32; $R^4$, $R^5$, $R^7$, $R^8$, and $R^9$ are hydrogen atoms; $R^{10}$ is a methyl group; and Q and Y are oxygen atoms. A tetrazolinone compound in which E is E33; $R^4$, $R^5$, $R^7$, $R^8$, and $R^9$ are hydrogen atoms; $R^{10}$ is a methyl group; and Q and Y are oxygen atoms. A tetrazolinone compound in which E is E34; $R^4$, $R^5$, $R^7$, $R^8$, and $R^9$ are hydrogen atoms; $R^{10}$ is a methyl group; and Q and Y are oxygen atoms. A tetrazolinone compound in which E is E35; $R^4$, $R^5$, $R^7$, $R^8$, and $R^9$ are hydrogen atoms; $R^{10}$ is a methyl group; and Q and Y are oxygen atoms. A tetrazolinone compound in which E is E36; $R^4$, $R^5$, $R^7$, $R^8$, and $R^9$ are hydrogen atoms; $R^{10}$ is a methyl group; and Q and Y are oxygen atoms. A tetrazolinone compound in which E is E37; $R^4$, $R^5$, $R^7$, $R^8$, and $R^9$ are hydrogen atoms; $R^{10}$ is a methyl group; and Q and Y are oxygen atoms. A tetrazolinone compound in which E is E38; $R^4$, $R^5$, $R^7$, $R^8$, and $R^9$ are hydrogen atoms; $R^{10}$ is a methyl group; and Q and Y are oxygen atoms. A tetrazolinone compound in which E is E39; $R^4$, $R^5$, $R^7$, $R^8$, and $R^9$ are hydrogen atoms; $R^{10}$ is a methyl group; and Q and Y are oxygen atoms. A tetrazolinone compound in which E is E40; $R^4$, $R^5$, $R^7$, $R^8$, and $R^9$ are hydrogen atoms; $R^{10}$ is a methyl group; and Q and Y are oxygen atoms.

A tetrazolinone compound in which E is E41; $R^4$, $R^5$, $R^7$, $R^8$, and $R^9$ are hydrogen atoms; $R^{10}$ is a methyl group; and Q and Y are oxygen atoms. A tetrazolinone compound in which E is E42; $R^4$, $R^5$, $R^7$, $R^8$, and $R^9$ are hydrogen atoms; $R^{10}$ is a methyl group; and Q and Y are oxygen atoms. A tetrazolinone compound in which E is E42; $R^4$, $R^5$, $R^7$, $R^8$, and $R^9$ are hydrogen atoms; $R^{10}$ is a methyl group; and Q and Y are oxygen atoms. A tetrazolinone compound in which E is E43; $R^4$, $R^5$, $R^7$, $R^8$, and $R^9$ are hydrogen atoms; $R^{10}$ is a methyl group; and Q and Y are oxygen atoms. A tetrazolinone compound in which E is E44; $R^4$, $R^5$, $R^7$, $R^8$, and $R^9$ are hydrogen atoms; $R^{10}$ is a methyl group; and Q and Y are oxygen atoms. A tetrazolinone compound in which E is E45; $R^4$, $R^5$, $R^7$, $R^8$, and $R^9$ are hydrogen atoms; $R^{10}$ is a methyl group; and Q and Y are oxygen atoms. A tetrazolinone compound in which E is E46; $R^4$, $R^5$, $R^7$, $R^8$, and $R^9$ are hydrogen atoms; $R^{10}$ is a methyl group; and Q and Y are oxygen atoms.

A tetrazolinone compound in which E is E1; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E2; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E3; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ and $R^{11}$ are methyl groups; and Q and Y are oxygen atoms. A tetrazolinone compound in which E is E4; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E5; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E6; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E7; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E8; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E9; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E10; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms.

A tetrazolinone compound in which E is E11; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E12; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E13; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E14; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E15; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E16; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E17; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E18; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E19; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E20; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms.

A tetrazolinone compound in which E is E21; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E22; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E23; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E24; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E25; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E26; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E27; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E28; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E29; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E30; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms.

A tetrazolinone compound in which E is E31; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E32; $R^1$ is a phenyl group optionally having one or more substituents selected from Group; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E33; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E34; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E35; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E36; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E37; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E38; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E39; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E40; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms.

A tetrazolinone compound in which E is E41; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E42; $R^1$ is a phenyl group optionally having one or more substituents selected from Group $P^1$; $R^6$ is a group selected from Group $P^3$; $R^4$, $R^5$, $R^7$, $R^5$, and $R^9$ are hydrogen atoms; $R^{10}$ is a methyl group; and Q and Y are oxygen atoms. A tetrazolinone compound in which E is E43; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E44; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E45; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms. A tetrazolinone compound in which E is E46; $R^1$ is a phenyl group optionally having one or more substituents selected from Group $P^1$; $R^6$ is a group selected from Group $P^3$; $R^4$, $R^5$, $R^7$, $R^8$, and $R^9$ are hydrogen atoms; $R^{10}$ is a methyl group; and Q and Y are oxygen atoms.

A tetrazolinone compound in which E is E1; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E2; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E3; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E4; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E5; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E6; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E7; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E8; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E9; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E10; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms.

A tetrazolinone compound in which E is E11; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E12; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E13; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E14; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E15; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E16; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E17; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E18; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E19; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E20; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms.

A tetrazolinone compound in which E is E21; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E22; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E23; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E24; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E25; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E26; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E27; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E28; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E29; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E30; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms.

A tetrazolinone compound in which E is E31; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E32; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E33; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E34; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E35; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E36; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4$, $R^5$, $R^7$, $R^8$, and $R^9$ are hydrogen atoms; $R^{10}$ is a methyl group; and Q and Y are oxygen atoms. A tetrazolinone compound in which E is E37; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4, R^5, R^7, R^8$, and $R^9$ are hydrogen atoms; $R^{10}$ is a methyl group; and Q and Y are oxygen atoms. A tetrazolinone compound in which E is E38; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4, R^5, R^7, R^8$, and $R^9$ are hydrogen atoms; $R^{10}$ is a methyl group; and Q and Y are oxygen atoms. A tetrazolinone compound in which E is E39; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4, R^5, R^7, R^8$, and $R^9$ are hydrogen atoms; $R^{10}$ is a methyl group; and Q and Y are oxygen atoms. A tetrazolinone compound in which E is E40; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4, R^5, R^7, R^8$, and $R^9$ are hydrogen atoms; $R^{10}$ is a methyl group; and Q and Y are oxygen atoms.

A tetrazolinone compound in which E is E41; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4, R^5, R^7, R^5$, and $R^9$ are hydrogen atoms; $R^{10}$ is a methyl group; and Q and Y are oxygen atoms. A tetrazolinone compound in which E is E42; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4, R^5, R^7, R^8$, and $R^9$ are hydrogen atoms; $R^{10}$ is a methyl group; and Q and Y are oxygen atoms. A tetrazolinone compound in which E is E43; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4, R^5, R^7, R^8$, and $R^9$ are hydrogen atoms; $R^{10}$ is a methyl group; and Q and Y are oxygen atoms. A tetrazolinone compound in which E is E44; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4, R^5, R^7, R^8$, and $R^9$ are hydrogen atoms; $R^{10}$ is a methyl group; and Q and Y are oxygen atoms. A tetrazolinone compound in which E is E45; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4, R^5, R^7, R^8$, and $R^9$ are hydrogen atoms; $R^{10}$ is a methyl group; and Q and Y are oxygen atoms. A tetrazolinone compound in which E is E46; $R^1$ is a phenyl group optionally having one or more substituents selected from Group $P^3$; $R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, or a haloalkoxy group having 1-3 carbon atoms; $R^4, R^5, R^7, R^8$, and $R^9$ are hydrogen atoms; $R^{10}$ is a methyl group; and Q and Y are oxygen atoms.

A tetrazolinone compound in which E is E19; $R^1$ is a phenyl group optionally having one or more halogen atoms; $R^0, R^{11}, R^4, R^5, R^7, R^8$, and $R^9$ are hydrogen atoms; $R^6$ is an alkyl group having 1-3 carbon atoms or an alkoxy group having 1-3 carbon atoms; $R^{10}$ is an alkyl group having 1-3 carbon atoms; and Q and Y are oxygen atoms.

A tetrazolinone compound in which E is E1; $R^1$ is a phenyl group optionally having one or more halogen atoms; $R^0, R^3, R^4, R^5, R^7, R^8$, and $R^9$ are hydrogen atoms; $R^6$ is an alkyl group having 1-3 carbon atoms or an alkoxy group having 1-3 carbon atoms; $R^{10}$ is an alkyl group having 1-3 carbon atoms; and Q and Y are oxygen atoms.

A tetrazolinone compound in which E is E1; $R^1$ is a phenyl group optionally having one or more halogen atoms; $R^0, R^3, R^4, R^5, R^7, R^5$, and $R^9$ are hydrogen atoms; $R^6$ is an alkyl group having 1-3 carbon atoms; $R^{10}$ is an alkyl group having 1-3 carbon atoms; and Q and Y are oxygen atoms.

A tetrazolinone compound in which E is E23; $R^1$ is a phenyl group optionally having one or more halogen atoms; $R^2, R^4, R^5, R^7, R^8$, and $R^9$ are hydrogen atoms; $R^6$ is an alkyl group having 1-3 carbon atoms or an alkoxy group having 1-3 carbon atoms; $R^{10}$ is an alkyl group having 1-3 carbon atoms; and Q and Y are oxygen atoms.

A tetrazolinone compound in which E is E23; R is a phenyl group; $R^2, R^4, R^5, R^7, R^8$, and $R^9$ are hydrogen atoms; $R^6$ is an alkyl group having 1-3 carbon atoms; $R^{10}$ is an alkyl group having 1-3 carbon atoms; and Q and Y are oxygen atoms.

A tetrazolinone compound in which E is E3; $R^1$ is a phenyl group optionally having one or more halogen atoms; $R^2, R^4, R^5, R^7, R^8$, and $R^9$ are hydrogen atoms; $R^6$ is an alkyl group having 1-3 carbon atoms or an alkoxy group having 1-3 carbon atoms; $R^{10}$ is an alkyl group having 1-3 carbon atoms; and Q and Y are oxygen atoms.

A tetrazolinone compound in which E is E3; $R^1$ is a phenyl group optionally having one or more halogen atoms; $R^2, R^4, R^5, R^7, R^8$, and $R^9$ are hydrogen atoms; $R^6$ is an alkyl group having 1-3 carbon atoms; $R^{10}$ is an alkyl group having 1-3 carbon atoms; and Q and Y are oxygen atoms.

A tetrazolinone compound in which E is E8; $R^1$ is a phenyl group optionally having one or more halogen atoms; $R^0, R^2, R^4, R^5, R^7, R^8$, and $R^9$ are hydrogen atoms; $R^6$ is an alkyl group having 1-3 carbon atoms or an alkoxy group having 1-3 carbon atoms; $R^{10}$ is an alkyl group having 1-3 carbon atoms; and Q and Y are oxygen atoms.

A tetrazolinone compound in which E is E8; $R^1$ is a phenyl group; $R^0, R^2, R^4, R^5, R^7, R^8$, and $R^9$ are hydrogen atoms; $R^6$ is an alkyl group having 1-3 carbon atoms; $R^{10}$ is an alkyl group having 1-3 carbon atoms; and Q and Y are oxygen atoms.

A tetrazolinone compound in which E is E11; $R^1$ is a phenyl group optionally having one or more halogen atoms;

$R^2$, $R^4$, $R^5$, $R^7$, $R^8$, and $R^9$ are hydrogen atoms; $R^6$ is an alkyl group having 1-3 carbon atoms or an alkoxy group having 1-3 carbon atoms; $R^{10}$ is an alkyl group having 1-3 carbon atoms; and Q and Y are oxygen atoms.

A tetrazolinone compound in which E is E11; $R^1$ is a phenyl group; $R^2$, $R^4$, $R^5$, $R^7$, $R^8$, and $R^9$ are hydrogen atoms; $R^6$ is an alkyl group having 1-3 carbon atoms or an alkoxy group having 1-3 carbon atoms; $R^{10}$ is an alkyl group having 1-3 carbon atoms; and Q and Y are oxygen atoms.

Next, a process for producing the present compound will be described.

The present compound can be produced, for example, by the following Production Processes.

(Production Process A)

The present compound represented by formula (1) (hereinafter referred to as the compound (1)) can be produced by reacting a compound represented by formula (A1) (hereinafter referred to as the compound (A1)) with a compound represented by formula (A2) (hereinafter referred to as the compound (A2)) in the presence of a base:

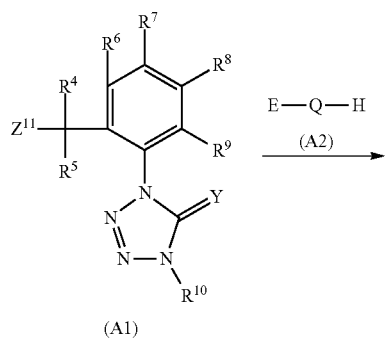

wherein $R^4$, $R^5$, $R^6$, $R^7$, $R^8$, $R^9$, $R^{10}$, E, Q, and Y are the same as defined above, $Z^{11}$ represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A2) is usually used in the proportion within a range of 1 to 10 mols, and the base is usually used in the proportion within a range of 0.5 to 5 mols, based on 1 mol of the compound (A1).

The reaction temperature of the reaction is usually within a range of −20 to 150° C. The reaction time is usually within a range of 0.1 to 24 hours.

In the reaction, if necessary, sodium iodide, tetrabutylammonium iodide, and the like may be added, and these compounds are usually used in the proportion of 0.001 to 1.2 mols based on 1 mol of the compound (A1).

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process B)

A compound (1) can be produced by reacting a compound represented by formula (1-3) (hereinafter referred to as the compound (1-3)) with a compound represented by formula (E1) (hereinafter referred to as the compound (E1)) in the presence of a base:

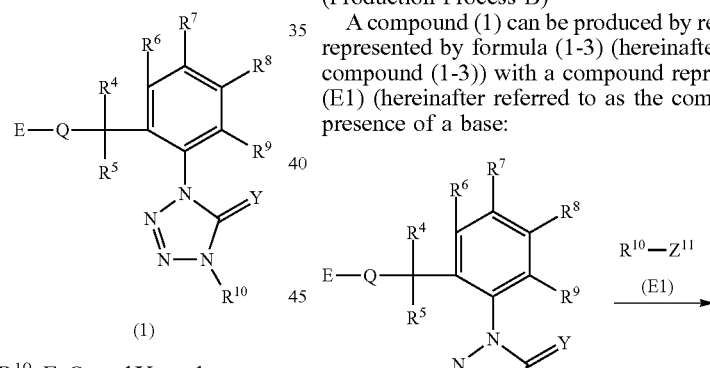

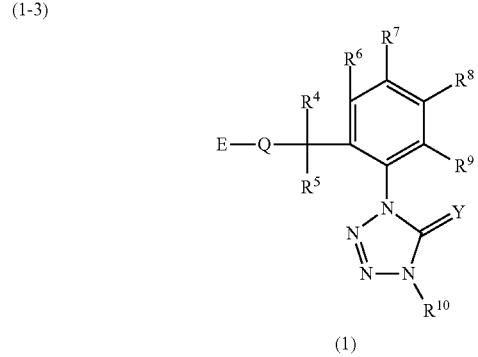

wherein $R^4$, $R^5$, $R^6$, $R^7$, $R^8$, $R^9$, $R^{10}$, E, Q, $Z^{11}$, and Y are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

It is possible to usually use, as the compound (E1) to be used in the reaction, commercially available compounds. Specific examples thereof include halogenated alkyls such as chlorodifluoromethane, methyl bromide, ethyl bromide, propyl bromide, methyl iodide, ethyl iodide, and 1,1-difluoro-2-iodoethane; dialkyl sulfates such as dimethyl sulfate; and sulfonic acid esters such as methyl p-toluenesulfonate, ethyl p-toluenesulfonate, propyl p-toluenesulfonate, methyl methanesulfonate, ethyl methanesulfonate, and propyl methanesulfonate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal hydrides such as lithium hydride, sodium hydride, and potassium hydride; and alkali metal alkoxides such as sodium tert-butoxide and potassium tert-butoxide.

In the reaction, the compound (E1) is usually used in the proportion within a range of 1 to 10 mols, and the base is usually used in the proportion within a range of 1 to 10 mols, based on 1 mol of the compound (1-3).

The reaction temperature of the reaction is usually within a range of −20 to 150° C. The reaction time is usually within a range of 0.1 to 24 hours.

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process C)

It is possible to produce a compound in which Y is a sulfur atom (hereinafter referred to as the compound (1-S)) among the compounds (1) by reacting a compound in which Y is an oxygen atom (hereinafter referred to as the compound (1-O)) among the compounds (1) with a sulfurizing agent:

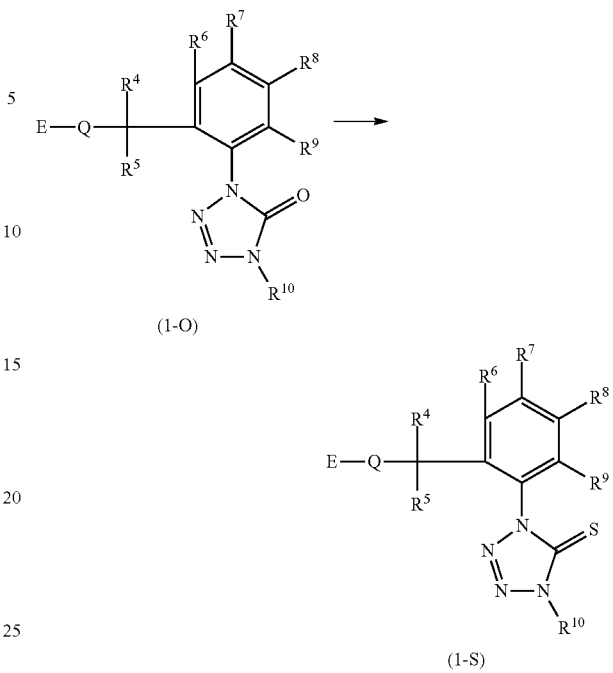

wherein $R^4$, $R^5$, $R^6$, $R^7$, $R^8$, $R^9$, $R^{10}$, E, and Q are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; nitriles such as acetonitrile and propionitrile; and mixtures thereof.

Examples of the sulfurizing agent to be used in the reaction include phosphorous pentasulfide and Lawesson's reagent (2,4-Bis(4-methoxyphenyl)-1,3,2,4-dithiadiphosphetane 2,4-disulfide).

In the reaction, the sulfurizing agent is preferably used in the proportion within a range of 0.5 to 1.5 mols based on 1 mol of the compound (1-O).

The reaction temperature of the reaction is usually within a range of −20 to 150° C. The reaction time is usually within a range of 0.1 to 24 hours.

In the reaction, if necessary, organic bases such as pyridine and triethylamine; and inorganic bases such as alkali metal hydroxide and alkali metal carbonate may be added, and the amount of the base to be added is within a range of 0.5 to 1.5 mols based on the compound (1-O).

After completion of the reaction, the compound (1-S) can be isolated by performing post-treatment operations such as extraction of the reaction mixture with an organic solvent, and drying and concentration of the organic layer. The isolated present compound can be further purified by chromatography, recrystallization, and the like.

(Production Process D)

Among the compounds (1), a compound represented by formula (1-1) in which $R^6$ is $R^{71}$ (hereinafter referred to as the compound (1-1)) can be produced by subjecting a compound represented by formula (F11) (hereinafter referred to as the compound (F11)) and a compound represented by formula (F21) (hereinafter referred to as the compound (F21)) to a coupling reaction in the presence of a base and a catalyst:

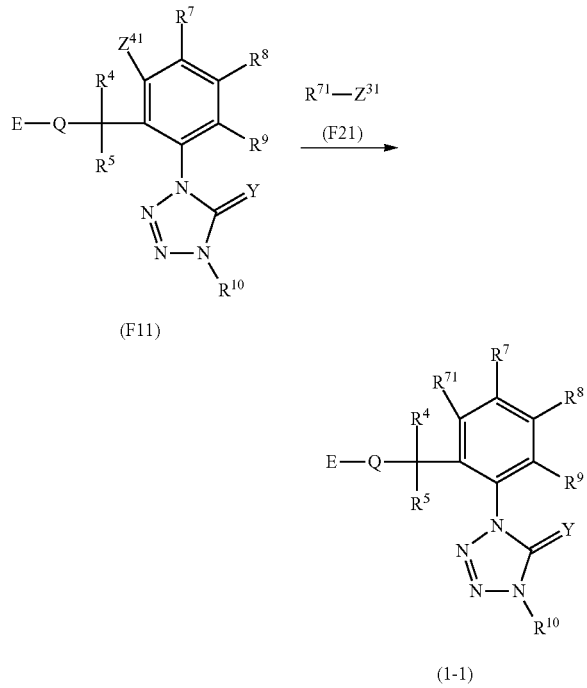

(F11)

(1-1)

wherein $R^4$, $R^5$, $R^7$, $R^8$, $R^9$, $R^{10}$, and X are the same as defined above, $Z^{41}$ represents a chlorine atom, a bromine atom, an iodine atom, or a trifluoromethanesulfonyloxy group, $R^{71}$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, or a C3-C6 halocycloalkyl group, and $Z^{31}$ represents $B(OH)_2$, an alkoxyboranyl group, or a trifluoroborate $BF_3^-K^+$.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; alcohols such as methanol, ethanol, propanol, and butanol; water; and mixtures thereof.

It is possible to usually use, as the organic boron compound (F21) to be used in the reaction, commercially available compounds, or compounds produced by a known method mentioned in review paper such as N. Miyaura and A. Suzuki, Chem. Rev., 1995, 95, 2457. It is possible to produce, as the organic boron compound (F21) to be used in the reaction, a boronic acid ester derivative by reacting an iodine compound ($R^{71}$—I) or a bromo compound ($R^{71}$—Br) with an alkyllithium such as butyllithium, followed by a reaction with a boric acid ester. It is possible to produce a boronic acid derivative by optionally hydrolyzing the boronic acid ester derivative obtained by the above-mentioned reaction. It is also possible to produce a trifluoroborate $BF_3^-K^+$ by fluorinating the boronic acid ester with potassium hydrogen fluoride in accordance with a known method mentioned in review paper such as Molander et al. Acc. Chem. Res., 2007, 40, 275.

Examples of the catalyst to be used in the reaction include palladium(II) acetate, dichlorobis(triphenylphosphine)palladium, tetrakis(triphenylphosphine)palladium(0), palladium (II) acetate/triscyclohexylphosphine, bis(diphenylphosphinoferrocenyl)palladium(II) dichloride, 1,3-bis(2,6-diisopropylphenyl)imidazol-2-ylidene(1,4-naphthoquinone) palladium dimer, allyl(chloro)(1,3-dimesityl-1,3-dihydro-2H-imidazol-2-ylidene)palladium or palladium(II) acetate/dicyclohexyl(2',4',6'-triisopropylbiphenyl-2-yl)phosphine, tris(dibenzylidineacetone)dipalladium, and the like.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (F21) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (F11).

The reaction temperature of the reaction is usually within a range of 0 to 150° C. The reaction time is usually within a range of 0.1 to 24 hours.

After completion of the reaction, the compound (1-1) can be isolated by performing post-treatment operations such as extraction of the reaction mixture with an organic solvent, and drying and concentration of the organic layer. The isolated present compound can be further purified by chromatography, recrystallization, and the like.

Among the compounds (1), a compound represented by formula (1-2) in which $R^7$ is $R^{72}$ (hereinafter referred to as the compound (1-2)) can be produced by subjecting a compound represented by formula (F12) (hereinafter referred to as the compound (F12)) and a compound represented by formula (F22) (hereinafter referred to as the compound (F22)) to a coupling reaction in the presence of a base and a catalyst:

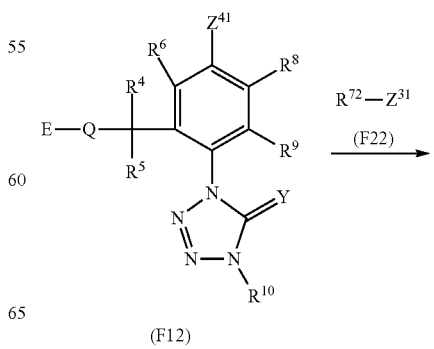

(F12)

-continued

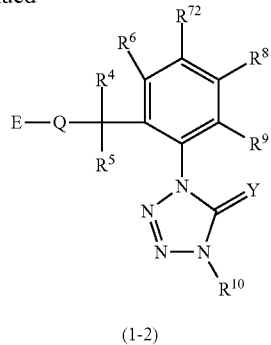

(1-2)

wherein $R^4$, $R^5$, $R^6$, $R^8$, $R^9$, $R^{10}$, $Z^{41}$, $Z^{31}$, and X are the same as defined above, and $R^{72}$ represents a C1-C4 alkyl group, a C1-C4 haloalkyl group, a C3-C5 cycloalkyl group, or a C3-C5 halocycloalkyl group.

The reaction is carried out in accordance with Production Process D.

Among the compounds (1), a compound represented by formula (1-3) in which $R^8$ is $R^{72}$ (hereinafter referred to as the compound (1-3)) can be produced by subjecting a compound represented by formula (F13) (hereinafter referred to as the compound (F13)) and the compound (F22) to a coupling reaction in the presence of a base and a catalyst:

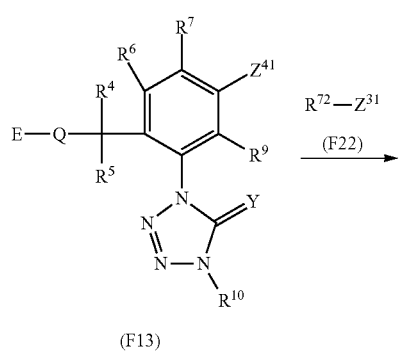

(F13)

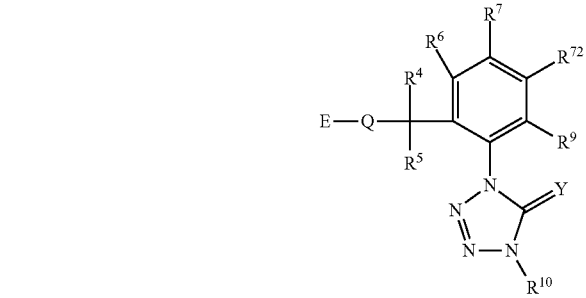

(1-3)

wherein $R^4$, $R^5$, $R^6$, $R^7$, $R^9$, $R^{10}$, $R^{72}$, $Z^{41}$, $Z^{31}$ and X are the same as defined above.

The reaction is carried out in accordance with Production Process D.

Among the compounds (1), a compound represented by formula (1-4) in which $R^9$ is $R^{72}$ (hereinafter referred to as the compound (1-4)) can be produced by subjecting a compound represented by formula (F14) (hereinafter referred to as the compound (F14)) and the compound (F22) to a coupling reaction in the presence of a base and a catalyst:

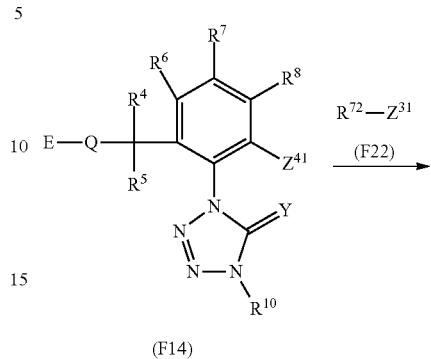

(F14)

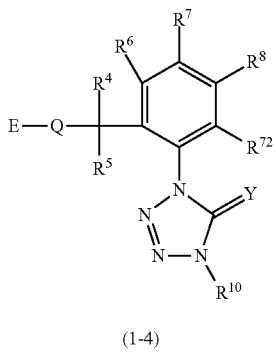

(1-4)

wherein $R^4$, $R^5$, $R^6$, $R^7$, $R^8$, $R^{10}$, $R^{72}$, $Z^{41}$, $Z^{31}$ and X are the same as defined above.

The reaction is carried out in accordance with Production Process D.

In accordance with Production Process D, it is possible to produce a compound in which two or more substituents selected from $R^6$, $R^7$, $R^8$ and $R^9$ are respectively $R^{71}$ or $R^{72}$, among the present compounds (1).

It is also possible to produce the compound (1) by using other known coupling reactions in place of the coupling reaction of Production Process D.

The process for synthesizing an intermediate compound will be mentioned in detail below.

(Reference Production Process A)

A compound represented by formula (XA3) (hereinafter referred to as the compound (XA3)) can be produced by reacting a compound represented by formula (XA1) (hereinafter referred to as the compound (XA1)) or a compound represented by formula (XA2) (hereinafter referred to as the compound (XA2)) with an azidation agent:

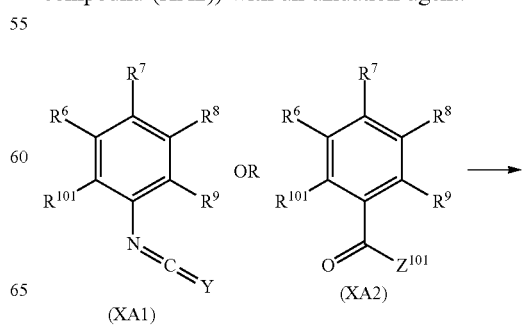

(XA1)    (XA2)

-continued

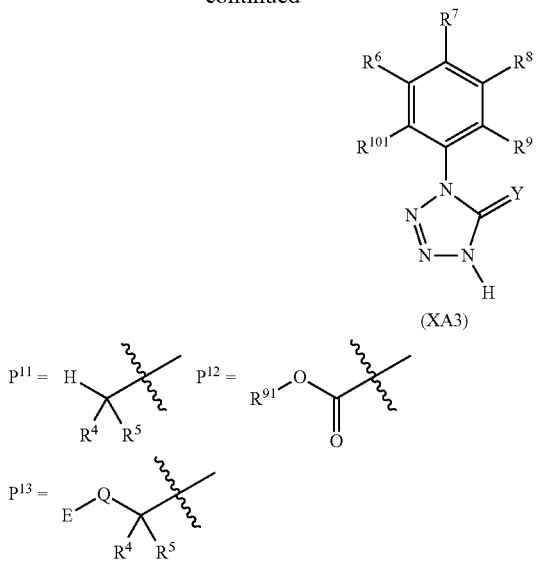

(XA3)

wherein $R^4$, $R^5$, $R^6$, $R^7$, $R^8$, $R^9$, E, Q, and Y are the same as defined above, $R^{101}$ represents $P^{11}$, $P^{12}$, or $P^{13}$, $R^{91}$ represents a C1-C12 alkyl group, $Z^{101}$ represents a chlorine atom or a bromine atom, and the wavy line represents a binding site.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (XA1) or the compound (XA2).

The reaction temperature of the reaction is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (XA1) or the compound (XA2).

After completion of the reaction, the compound (XA3) can be isolated by performing post-treatment operations such as extraction of the reaction mixture with an organic solvent, and drying and concentration of the organic layer. The isolated compound (XA3) can be further purified by chromatography, recrystallization, and the like.

(Reference Production Process B)

The compound (XA1) can be produced by reacting a compound represented by formula (XB1) (hereinafter referred to as the compound (XB1)) with an isocyanating agent:

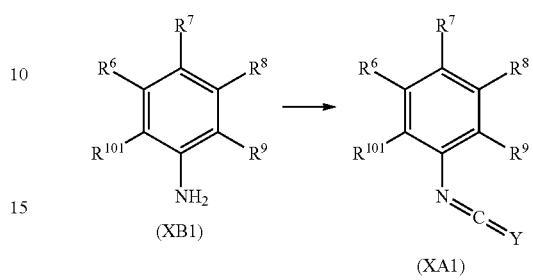

wherein $R^6$, $R^7$, $R^8$, $R^9$, $R^{101}$, and Y are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; and mixtures thereof.

Examples of the isocyanating agent to be used in the reaction include phosgene, diphosgene, triphosgene, thiophosgene, N,N-carbodiimidazole, and N,N-thiocarbodiimidazole.

In the reaction, the isocyanating agent is usually used in the proportion within a range of 0.34 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added, and these compounds are usually used in the proportion within a range of 0.05 to 5 mols based on 1 mol of the compound (XB1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process C)

The compound (XA2) can be produced by reacting a compound represented by formula (XC1) (hereinafter referred to as the compound (XC1)) with a halogenating agent:

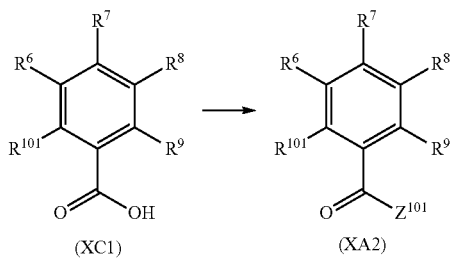

wherein $R^6$, $R^7$, $R^8$, $R^9$, $R^{101}$ and $Z^{101}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; and mixtures thereof.

Examples of the halogenating agent to be used in the reaction include phosphorus oxychloride, phosphorus trichloride, phosphorus pentachloride, thionyl chloride, phosphorus oxybromide, phosphorus tribromide, phosphorus pentabromide, oxalyl dichloride, oxalyl dibromide, triphosgene, diphosgene, phosgene, and sulfuryl chloride.

In the reaction, the halogenating agent is usually used in the proportion within a range of 1 to 10 mols based on 1 mol of the compound (XC1).

The reaction temperature of the reaction is usually within a range of −20 to 150° C. The reaction time is usually within a range of 0.1 to 24 hours.

In the reaction, if necessary, a catalyst may be added, and organic bases such as N,N-dimethylformamide, triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added, and these compounds are usually used in the proportion within a range of 0.001 to 5 mols based on 1 mol of the compound (XC1).

After completion of the reaction, the compound (XA2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process D)

The compound (XA1) can be produced by reacting the compound (XB1) with a carbamating agent to obtain a compound represented by the following formula (XD1) (hereinafter referred to as the compound (XD1)), and then reacting the compound (XD1) with an isocyanating agent:

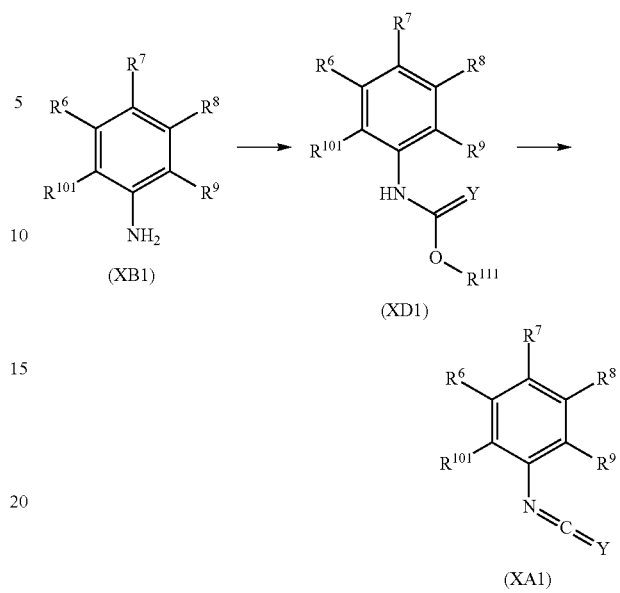

wherein $R^6$, $R^7$, $R^8$, $R^9$, $R^{101}$, and Y are the same as defined above, and $R^{111}$ represents a C1-C12 alkyl group or a phenyl group.

The process for producing the compound (XD1) from the compound (XB1) will be described below.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the carbamating agent to be used in the reaction include phenyl chlorocarbonate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, O-phenyl chlorothioformate, O-methyl chlorothioformate, O-ethyl chlorothioformate, and the like.

In the reaction, the carbamating agent is usually used in the proportion within a range of 1 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added, and these compound are usually used in the proportion within a range of 0.05 to 5 mols based on 1 mol of the compound (XB1).

After completion of the reaction, the compound (XD1) can be isolated by performing post-treatment operations such as extraction of the reaction mixture with an organic solvent, and drying and concentration of the organic layer. The isolated compound may be further purified by operations such as distillation, chromatography, and recrystallization.

The process for producing the compound (XA1) from the compound (XD1) will be described below.

The reaction is usually performed in a solvent.

Examples of the solvent to be used in the reaction include ethers such as tetrahydrofuran, dioxane, ethylene glycol dimethyl ether, and methyl tert-butyl ether; aromatic hydrocarbons such as toluene and xylene; halogenated hydrocarbons such as carbon tetrachloride, chloroform or 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

It is possible to use, as the isocyanating agent to be used in the reaction, for example, phosphorus pentachloride, phosphorus oxychloride, diphosphorus pentaoxide, trichlorosilane, dichlorosilane, monochlorosilane, boron trichloride, 2-chloro-1,3,2-benzodioxaborole, diiodosilane, methyltrichlorosilane, dimethyldichlorosilane, chlorotrimethylsilane, and the like.

In the reaction, the isocyanating agent is usually used in the proportion within a range of 1 to 10 mols based on 1 mol of the compound (XD1).

The reaction temperature of the reaction is usually within a range of −20 to 250° C. The reaction time is usually within a range of 0.1 to 24 hours.

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added, and these compounds are usually used in the proportion within a range of 0.05 to 5 mols based on 1 mol of the compound (XD1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process E)

A compound represented by formula (XE2) (hereinafter referred to as the compound (XE2)) can be produced by reacting a compound represented by formula (XE1) (hereinafter referred to as the compound (XE1)) with an excess amount of hydrogen in the presence of a catalyst:

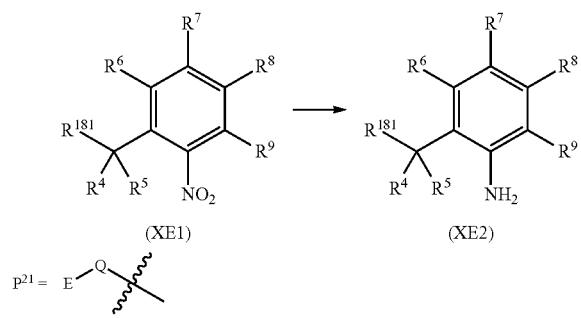

wherein $R^4$, $R^5$, $R^6$, $R^7$, $R^8$, $R^9$, E, and Q are the same as defined above, $R^{181}$ represents a hydrogen atom or $P^{21}$, and the wavy line represents a binding site.

The reaction is usually performed in a solvent.

Examples of the solvent to be used in the reaction include alcohols such as methanol, ethanol, propanol, and butanol; esters such as ethyl acetate and butyl acetate; halogenated hydrocarbons such as carbon tetrachloride, chloroform, dichloromethane, 1,2-dichloroethane, tetrachloroethane, and chlorobenzene; ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; water; and mixtures thereof.

Examples of the catalyst to be used in the reaction include palladium-supported carbon (Pd/C), platinum-supported carbon (Pt/C), osmium-supported carbon (Os/C), ruthenium-supported carbon (Ru/C), rhodium-supported carbon (Rh/C), Raney (registered trademark) nickel, and the like.

In the reaction, the catalyst is usually used in the proportion within a range of 0.0001 to 1 mols based on 1 mol of the compound (XE1).

The reaction temperature of the reaction is usually within a range of −20 to 150° C. The reaction time is usually within a range of 0.1 to 24 hours.

After completion of the reaction, the compound (XE2) can be isolated by performing post-treatment operations such as concentration of the organic layer after filtration of the catalyst. The isolated compound may be further purified by operations such as distillation, chromatography, and recrystallization.

(Reference Production Process F)

The compound (XE2) can be produced by reacting the compound (XE1) with a reducing agent in the presence of an acid:

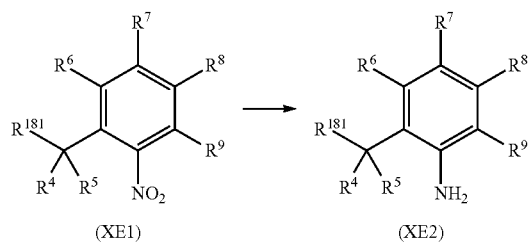

wherein $R^4$, $R^5$, $R^6$, $R^7$, $R^8$, $R^9$ and $R^{181}$ are the same as defined above.

The reaction is usually performed in a solvent.

Examples of the solvent to be used in the reaction include aliphatic carboxylic acids such as acetic acid; alcohols such as methanol and ethanol; water; and mixtures thereof.

Examples of the reducing agent to be used in the reaction include iron, tin, and zinc.

Examples of the acid to be used in the reaction include hydrochloric acid, sulfuric acid, acetic acid, aqueous ammonium chloride solution, and the like, and the acid is usually used in the proportion within a range of 0.01 to 30 mols based on 1 mol of the compound (XE1).

In the reaction, the reducing agent is usually used in the proportion within a range of 1 to 30 mols based on 1 mol of the compound (XE1).

The reaction temperature of the reaction is usually within a range of −20 to 150° C. The reaction time is usually within a range of 0.1 to 24 hours.

After completion of the reaction, the compound (XE2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process G)

A compound represented by formula (XG2) (hereinafter referred to as the compound (XG2)) can be produced by reacting a compound represented by formula (XG1) (hereinafter referred to as the compound (XG1)) with the compound (E1) in the presence of a base:

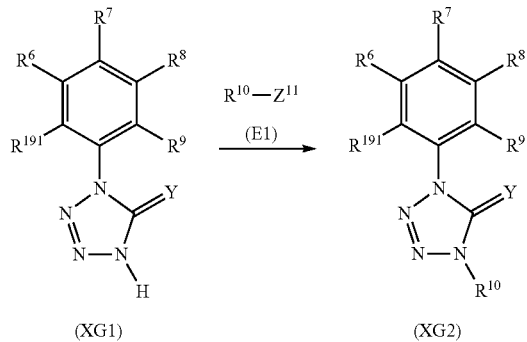

wherein $R^6$, $R^7$, $R^8$, $R^9$, $R^{10}$, Y and $Z^{11}$ are the same as defined above, and $R^{191}$ represents $P^{11}$ or $P^{12}$.

The reaction can be carried out in accordance with Production Process E mentioned above.

(Reference Production Process H)

A compound represented by formula (XH2) (hereinafter referred to as the compound (XH2)) can be produced by reacting a compound represented by formula (XH1) (hereinafter referred to as the compound (XH1)) with a halogenating agent:

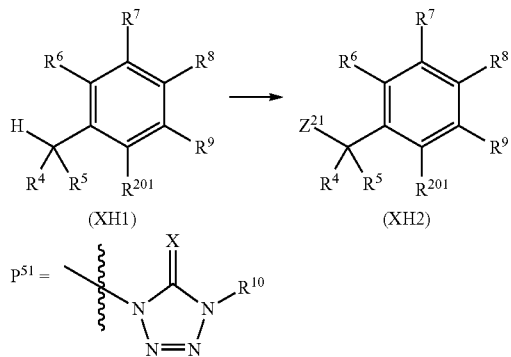

wherein $R^4$, $R^5$, $R^6$, $R^7$, $R^8$, $R^9$, $R^{10}$, and Y are the same as defined above, and $R^{201}$ represents $P^{51}$ or a nitro group. $Z^{21}$ represents a chlorine atom, a bromine atom, or an iodine atom.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, fluorobenzene, difluorobenzene, trifluorobenzene, chlorobenzene, dichlorobenzene, trichlorobenzene, α,α,α-trifluorotoluene, and α,α,α-trichlorotoluene; esters such as ethyl acetate and methyl acetate; ketones such as acetone, methyl ethyl ketone, and methyl isobutyl ketone; nitriles such as acetonitrile and propionitrile; and mixtures thereof.

Examples of the halogenating agent usable in the reaction include a chlorinating agent, a brominating agent, or an iodinating agent, for example, chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonimide, N-bromophthalimide, and the like.

In the reaction, a radical initiator can also be used.

Examples of the radical initiator to be used in the reaction include benzoyl peroxide, azobisisobutyronitrile (AIBN), and the like.

In the reaction, the halogenating agent is usually used in the proportion within a range of 1 to 10 mols, and the radical initiator is usually used in the proportion within a range of 0.01 to 5 mols, based on 1 mol of the compound (XH1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process I)

A compound represented by formula (XJ2) (hereinafter referred to as the compound (XJ2)) can be produced by reacting the compound (XH2) with a compound represented by formula (XJ1) (hereinafter referred to as the compound (XJ1)):

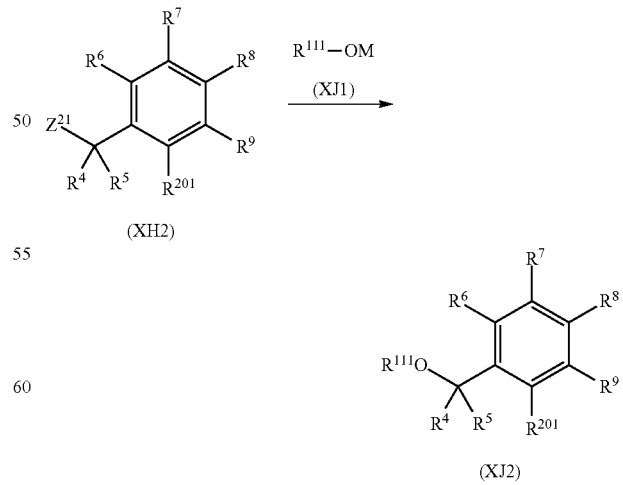

wherein $R^4$, $R^5$, $R^6$, $R^7$, $R^8$, $R^9$, $R^{111}$, $R^{201}$ and $Z^{21}$ are the same as defined above, and M represents sodium, potassium, or lithium.

The reaction is usually performed in a solvent.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the compound (XJ1) usable in the reaction include sodium methoxide, sodium ethoxide, sodium propoxide, sodium butoxide, sodium isopropoxide, sodium sec-butoxide, sodium tert-butoxide, potassium methoxide, potassium ethoxide, potassium propoxide, potassium butoxide, potassium isopropoxide, potassium sec-butoxide, potassium tert-butoxide, sodium phenoxide, and the like.

In the reaction, the compound (XJ1) is usually used in the proportion within a range of 1 to 10 mols based on 1 mol of the compound (XH2).

The reaction temperature of the reaction is usually within a range of −20 to 150° C. The reaction time is usually within a range of 0.1 to 24 hours.

After completion of the reaction, the compound (XJ2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process J)

A compound represented by formula (XK1) (hereinafter referred to as the compound (XK1)) can be produced by reacting the compound (XH2) with water in the presence of a base:

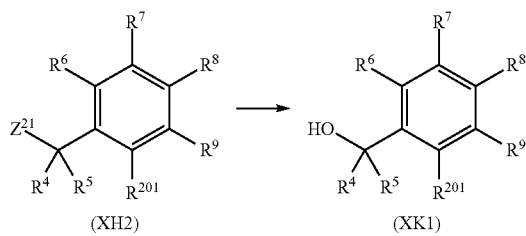

wherein $R^4$, $R^5$, $R^6$, $R^7$, $R^8$, $R^9$, $R^{201}$, and $Z^{21}$ are the same as defined above.

The reaction is usually performed in water, or a solvent containing water.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; metal organic acid salts such as lithium formate, lithium acetate, sodium formate, sodium acetate, potassium formate, and potassium acetate; metal nitrates such as silver nitrate and sodium nitrate; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; and alkali metal alkoxides such as sodium methoxide, sodium ethoxide, sodium tert-butoxide, and potassium tert-butoxide.

In the reaction, the base is usually used in the proportion within a range of 1 to 100 mols based on 1 mol of the compound (XH2).

In the reaction, water is usually used in the proportion within a range of 1 mol to large excess based on 1 mol of the compound (XH2).

The reaction temperature of the reaction is usually within a range of −20 to 150° C. The reaction time is usually within a range of 0.1 to 24 hours.

After completion of the reaction, the compound (XK1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process K)

The compound (XH2) can be produced by reacting the compound (XJ2) with a halogenating agent:

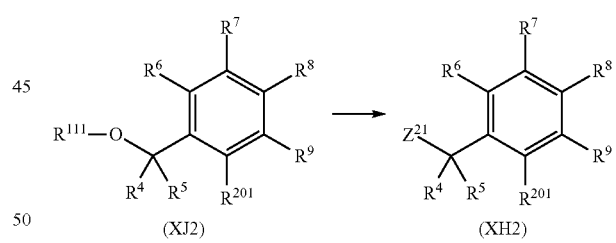

wherein $R^4$, $R^5$, $R^6$, $R^7$, $R^8$, $R^9$, $R^{111}$, $R^{201}$, and $Z^{21}$ are the same as defined above.

The reaction is usually performed in a solvent.

Examples of the solvent to be used in the reaction include hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; ketones such as acetone, methyl ethyl ketone, and methyl isobutyl ketone; nitriles such as acetonitrile and propionitrile; organic acids such as formic acid, acetic acid, and trifluoroacetic acid; water; and mixtures thereof.

Examples of the halogenating agent to be used in the reaction include hydrochloric acid, hydrobromic acid, and hydroiodic acid.

In the reaction, the halogenating agent is usually used in the proportion of 1 mol or more based on 1 mol of the compound (XJ2).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process L)

The compound (XH2) can be produced by reacting the compound (XK1) with a halogenating agent:

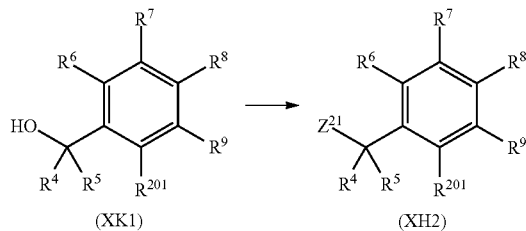

wherein $R^4$, $R^5$, $R^6$, $R^7$, $R^8$, $R^9$, $R^{201}$, and $Z^{21}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; organic acids such as formic acid, acetic acid, and trifluoroacetic acid; water; and mixtures thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorus oxychloride, phosphorus trichloride, phosphorus pentachloride, thionyl chloride, phosphorus oxybromide, phosphorus pentabromide, phosphorus triiodide, oxalyl dichloride, oxalyl dibromide, acetyl chloride, carbon tetrabromide, N-bromosuccinimide, lithium chloride, sodium iodide, acetyl bromide, and the like.

In the reaction, the halogenating agent is usually used in the proportion within a range of 1 to 10 mols based on 1 mol of the compound (XK1).

In order to accelerate the reaction, additives may be added according to the halogenating agent to be used, and specific examples thereof include zinc chloride for acetyl chloride, triphenylphosphine for carbon tetrabromide, dimethyl sulfide for N-bromosuccinimide, boron trifluoride diethyl ether complex for sodium iodide, boron trifluoride diethyl ether complex for acetyl bromide, triethylamine and methanesulfonyl chloride for lithium chloride, aluminum chloride for sodium iodide, trimethylsilyl chloride for sodium iodide, and the like. Any additives are usually used in the proportion within a range of 0.01 to 5 mols based on 1 mol of the compound (XK1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process M)

A compound represented by formula (XM3) (hereinafter referred to as the compound (XM3)) can be produced by reacting the compound (XK1) with a compound represented by formula (XM2) (hereinafter referred to as the compound (XM2)) in the presence of a base:

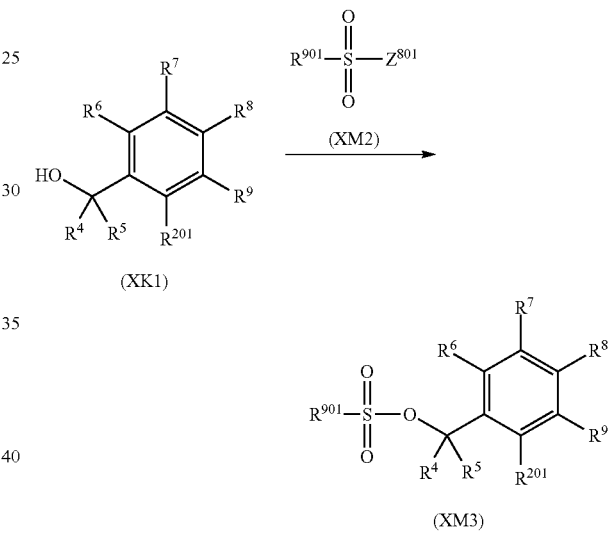

wherein $R^4$, $R^5$, $R^6$, $R^7$, $R^8$, $R^9$ and $R^{201}$ are the same as defined above, $R^{901}$ represents a C1-C6 alkyl group, a C1-C6 haloalkyl group, a C6-C16 aryl group, or a C6-C16 haloaryl group, and $Z^{801}$ represents a fluorine atom, a chlorine atom, a bromine atom, or an iodine atom.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium methoxide, sodium ethoxide, sodium tert-butoxide, and potassium tert-butoxide.

The compound (XM2) is generally a commercially available compound.

In the reaction, the compound (XM2) is usually used in the proportion within a range of 1 to 10 mols, and the base is usually used in the proportion within a range of 1 to 5 mols, based on 1 mol of the compound (XK1).

The reaction temperature of the reaction is usually within a range of −20 to 150° C. The reaction time is usually within a range of 0.1 to 24 hours.

In the reaction, if necessary, sodium iodide, tetrabutylammonium iodide, and the like may be added, and these compounds are usually used in the proportion within a range of 0.001 to 1.2 mols based on 1 mol of the compound (XK1).

After completion of the reaction, the compound (XM3) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process N)

A compound represented by formula (XN12) (hereinafter referred to as the compound (XN12)) can be produced by subjecting a compound represented by formula (XN11) (hereinafter referred to as the compound (XN11)) and the compound (G21) to a coupling reaction in the presence of a base and a catalyst:

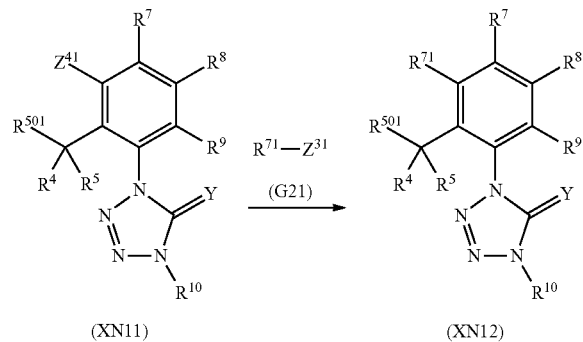

(XN11)    (XN12)

wherein $R^{501}$ represents a hydrogen atom or $OR^{111}$, and $R^{111}$, $R^4$, $R^5$, $R^6$, $R^7$, $R^8$, $R^9$, $Z^{41}$, $Z^{31}$, $R^{71}$, and Y are the same as defined above.

The reaction can be carried out in accordance with the reaction mentioned in the Production Process D.

A compound represented by formula (XN22) (hereinafter referred to as the compound (XN22)) can be produced by subjecting a compound represented by formula (XN21) (hereinafter referred to as the compound (XN21)) and the compound (G22) to a coupling reaction in the presence of a base and a catalyst:

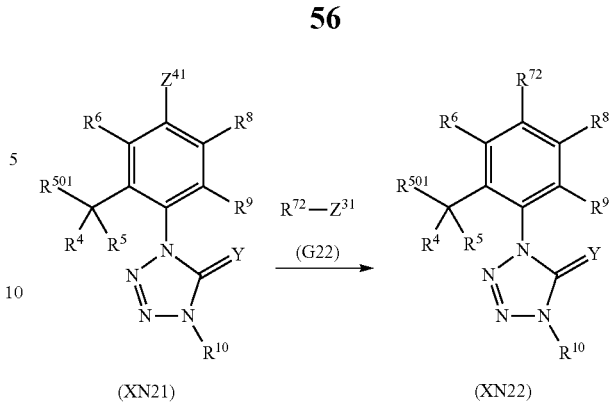

(XN21)    (XN22)

wherein $R^4$, $R^5$, $R^6$, $R^7$, $R^8$, $R^9$, $R^{10}$, $R^{72}$, $R^{501}$, X, $Z^{31}$, and $Z^{41}$ are the same as defined above.

The reaction can be carried out in accordance with the reaction mentioned in the Production Process D.

A compound represented by formula (XN32) (hereinafter referred to as the compound (XN32)) can be produced by subjecting a compound represented by formula (XN31) (hereinafter referred to as the compound (XN31)) and the compound (G22) to a coupling reaction in the presence of a base and a catalyst:

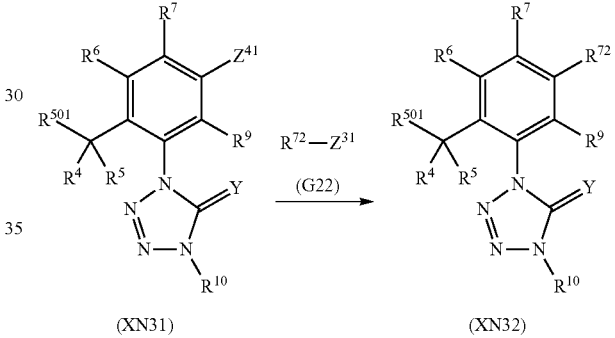

(XN31)    (XN32)

wherein $R^4$, $R^5$, $R^6$, $R^7$, $R^8$, $R^9$, $R^{72}$, $R^{501}$, Y, $Z^{31}$, and $Z^{41}$ are the same as defined above.

The reaction can be carried out in accordance with the reaction mentioned in the Production Process D.

A compound represented by formula (XN42) (hereinafter referred to as the compound (XN42)) can be produced by subjecting a compound represented by formula (XN41) (hereinafter referred to as the compound (XN41)) and the compound (G22) to a coupling reaction in the presence of a base and a catalyst:

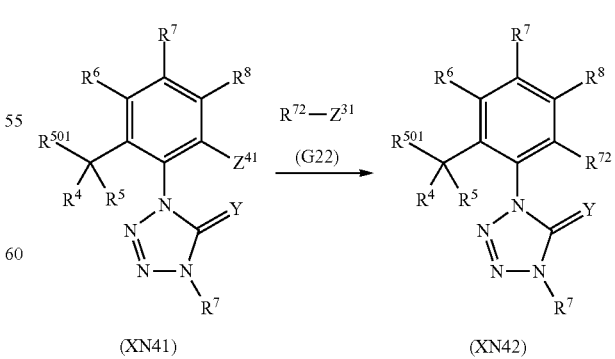

(XN41)    (XN42)

wherein $R^4$, $R^5$, $R^6$, $R^7$, $R^8$, $R^9$, $R^{72}$, $R^{501}$, X, $Z^{31}$, and $Z^{41}$ are the same as defined above.

The reaction can be carried out in accordance with the reaction mentioned in the Production Process D.

In accordance with Production Process B mentioned above, it is possible to produce a compound in which two or more substituents selected from $R^3$, $R^4$, $R^5$, and $R^6$ are $R^{71}$ and/or $R^{72}$, among the compounds represented by formula (XN50):

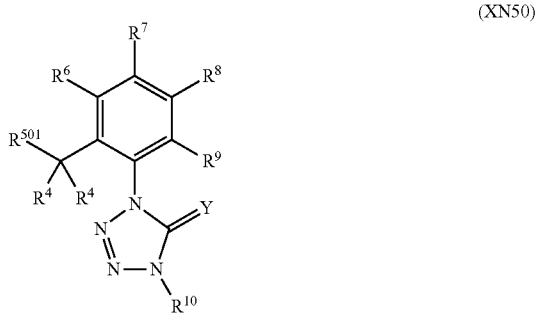

wherein $R^4$, $R^5$, $R^6$, $R^7$, $R^8$, $R^9$, $R^{10}$, $R^{501}$, and y are the same as defined above.

Furthermore, it is possible to produce the compound (XN50) by other known coupling reactions in place of the coupling reaction mentioned in Production Process D mentioned above.

(Reference Production Process O)

A compound represented by formula (XW2) (hereinafter referred to as the compound (XW2)) can be produced by reacting a compound represented by formula (XW1) (hereinafter referred to as the compound (XW1)) with a compound represented by formula (XW3) (hereinafter referred to as the compound (XW3)) in the presence of a reaction accelerator:

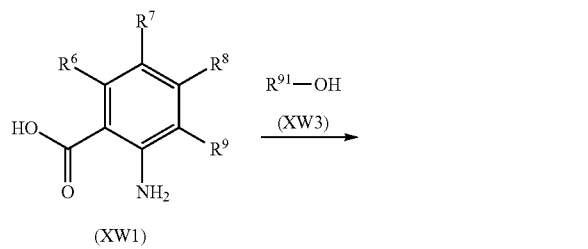

wherein $R^6$, $R^7$, $R^8$, $R^9$ and $R^{91}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl test-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof, and the compound (XW3) may be used as the solvent.

Examples of the compound (XW3) usable in the reaction include methanol, ethanol, propanol, isopropanol, n-butanol, sec-butanol, tert-butanol, n-pentanol, and the like.

Examples of the reaction accelerator to be used in the reaction include mineral acids such as hydrochloric acid and sulfuric acid; carbodiimides such as dicyclohexylcarbodiimide, diisopropylcarbodiimide, and N'-(3-dimethylaminopropyl)-N-ethylcarbodiimide; organic acids such as methanesulfonic acid and toluenesulfonic acid; Mitsunobu reaction reagents such as triphenylphosphine/diethyl azodicarboxylate; thionyl chloride, boron trifluoride-ethyl ether complex, and the like.

In the reaction, the reaction accelerator is usually used in the proportion within a range of 0.01 to 10 mols based on 1 mol of the compound (XW1).

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added, and these compounds are usually used in the proportion within a range of 0.001 to 5 mols based on 1 mol of the compound (XW1).

In the reaction, an excess amount of the compound (XW3) is used based on the compound (XW1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process P)

The compound (XW2) can be produced by reacting the compound (XW1) with a halogenating agent to obtain a compound represented by formula (XV1) (hereinafter referred to as the compound (XV1)), and then reacting the compound (XV1) with the compound (XW3):

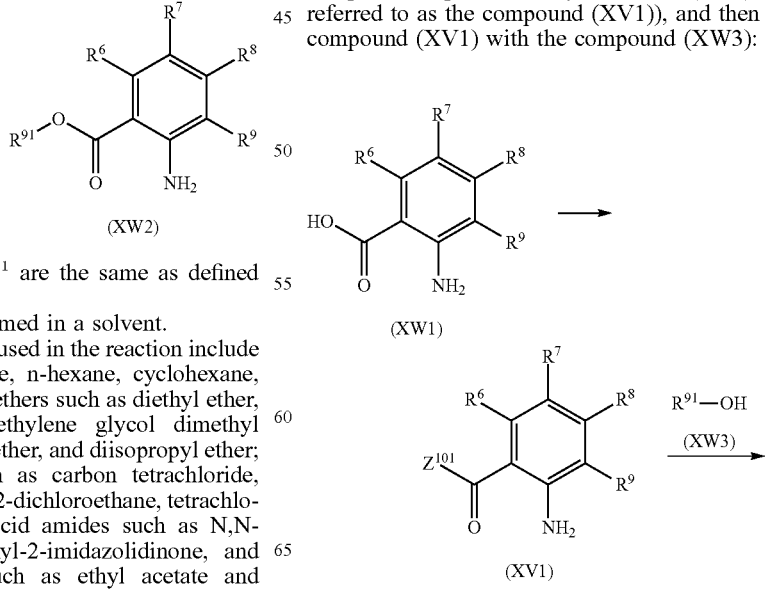

-continued

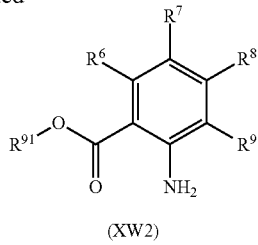

wherein $R^6$, $R^7$, $R^8$, $R^9$, $R^{91}$, and $Z^{101}$ are the same as defined above.

The process for producing the compound (XV1) by reacting the compound (XW1) with a halogenating agent can be carried out in accordance with the reaction mentioned in Reference Production Process C.

The process for producing the compound (XW2) from the compound (XV1) will be described below.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof, and the compound (XW3) may be used as the solvent.

In the reaction, an excess amount of the compound (XW3) is used based on the compound (XV1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process Q)

The compound (XW2) can be produced by reacting the compound (XW1) with an alkylating agent:

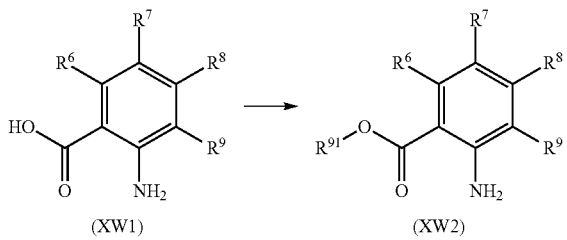

wherein $R^6$, $R^7$, $R^8$, $R^9$, and $R^{91}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the alkylating agent usable in the reaction include halogenated alkyls such as diazomethane, trimethylsilyldiazomethane, methyl bromide, ethyl bromide, propyl bromide, methyl iodide, ethyl iodide, and propyl iodide; dialkyl sulfates such as dimethyl sulfate, diethyl sulfate, and di-n-propyl sulfate; and sulfonic acid esters such as methyl p-toluenesulfonate, ethyl p-toluenesulfonate, n-propyl p-toluenesulfonate, methyl methanesulfonate, ethyl methanesulfonate, and propyl methanesulfonate.

In the reaction, the alkylating agent is usually used in the proportion within a range of 1 to 10 mols based on 1 mol of the compound (XW1).

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; and quaternary ammonium salts such as tetra(n-butyl)ammonium hydroxide may be added, and these compounds are usually used in the proportion within a range of 0.001 to 5 mols based on 1 mol of the compound (XW1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process T)

A compound represented by formula (XS2) (hereinafter referred to as the compound (XS2)) can be produced by reacting a compound represented by formula (XS1) (hereinafter referred to as the compound (XS1)) with the compound (A2) in the presence of a base:

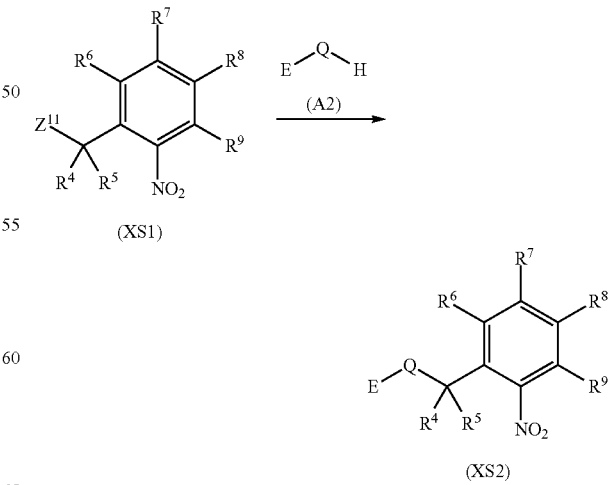

wherein $R^4$, $R^5$, $R^6$, $R^7$, $R^8$, $R^9$, E, Q, and $Z^{11}$ are the same as defined above.

The reaction can be carried out in accordance with the reaction mentioned in Production Process A.

Although a form used for the present compound may be the present compound as itself, the present compound is usually used after mixing with solid carriers, liquid carriers, surfactants, and the like, and optionally adding auxiliary agents for formulation, such as stickers, dispersers, and stabilizers to thereby formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexanone, and kerosene), esters (for example, ethyl acetate and butyl acetate), nitriles (for example, acetonitrile and isobutyronitrile), ethers (for example, dioxane and diisopropylether), acid amides (for example, DMF and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyethylene glycol ethers, polyhydric alcohol esters, and sugar alcohol derivatives.

Examples of other auxiliary agents for formulation include stickers and dispersers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof, and the like.

The method for applying the present control agent is not particularly limited, as long as the applying form is a form by which the present control agent can be applied substantially, and includes, for example, an application to plants such as a foliage application; an application to area for cultivating plants such as a submerged treatment; and an application to soil such as seed disinfection.

The present control agent may be used as a mixture with various oils or surfactants such as mineral oils or vegetable oils. Specific examples of oils or surfactants, which can be used as a mixture with various oils or surfactants include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), BANOLE (registered trademark), and the like.

Also, in another embodiment, for example, the present compound can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, or administration via injection subcutaneously, intramuscularly or intravenously. Examples of a method of the external administration include transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., and it is desirable in general to administer the present compound so that a dose of the active ingredient (the present compound or salts thereof) is generally within a range of 0.1 mg to 2,000 mg, and preferably 0.5 mg to 1,000 mg, per 1 kg of body weight of the animal.

The present compound can be used as an agent for controlling plant diseases in agricultural lands such as fields, paddy fields, lawns, and orchards. The present compound can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), umbelliferous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, and the like; Flowers; Ornamental foliage plants;

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, persimmon, olive, loquat, banana, coffee, date palm, coconuts, and the like;

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir tree, hemlock, juniper, *Pinus, Picea*, and *Taxus* cuspidate); and the like.

The above-mentioned "plants" include genetically modified crops.

The pests which can be controlled by the present compound include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium graminearum, F. avenaceum, F. culmorum, Microdochium nivale*), rust (*Puccinia striiformis, P. graminis, P. recondita*), snow mould (*Micronectriella nivale*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), yellow spot (*Pyrenophora tritici-repentis*), seeding blight caused by rhizoctonia fungus (*Rhizoctonia solani*), and take-all disease (*Gaeumannomyces graminis*); Barley diseases: powdery mildew (*Erysiphe graminis*), *fusarium* blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and seeding blight caused by rhizoctonia fungus (*Rhizoctonia solani*); Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum graminicola*), gray leaf spot (*Cercospora zeae-maydis*), eyespot (*Kabatiella zeae*), and *phaeosphaeria* leaf spot (*Phaeosphaeria maydis*); Cotton diseases: anthracnose (*Colletotrichum gossypii*), grey mildew (*Ramularia areola*), and *alternaria* leaf spot (*Alternaria macrospora, A. gossypii*);

Coffee diseases: rust (*Hemileia vastatrix*); Rape seed diseases: *sclerotinia* rot (*Sclerotinia sclerotiorum*), gray leaf spot (*Alternaria brassicae*), and root rot (*Phoma lingam*); Citrus diseases: melanose (*Diaporthe citri*), scab (*Elsinoe fawcetti*), and green mold (*Penicillium digitatum, P. italicum*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Glomerellaa cingulata, Colletotrichum acutatum*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata, Colletotrichum acutatum*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), *Corynespora* leaf spot (*Corynespora cassiicola*), *fusarium* wilt (*Fusarium oxysporum*), downy mildew (*Pseudoperonospora cubensis*), phytophthora rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), and late blight (*Phytophthora infestans*); Eggplant diseases: brown spot (*Phomopsis vexans*) and powdery mildew (*Erysiphe cichoracearum*);

Cruciferous vegetables diseases: *alternaria* leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), sphaceloma scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, C. truncatum*), *Rhizoctonia* rot (*Rhizoctonia solani*), septoria brown spot (*Septoria glycines*), and frog eye leaf spot (*Cercospora sojina*); Kidney bean diseases: anthracnose (*Colletotrichum lindemuthianum*); Peanut diseases: leaf spot (*Cercospora personata*), brown leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), and verticillium wilt (*Verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*); Sugar beet diseases: *cercospora* leaf spot (*Cercospora beticola*), leaf blight (*Thanatephorus cucumeris*), root rot (*Thanatephorus cucumeris*), and *aphanomyces* root rot (*Aphanomyces cochlioides*); Rose diseases: black spot (*Diplocarpon rosae*) and powdery mildew (*Sphaerotheca pannosa*);

Chrysanthemum diseases: leaf blight (*Septoria chrysanthemi-indici*) and white rust (*Puccinia horiana*); Onion diseases: *botrytis* leaf blight (*Botrytis cinerea, B. byssoidea, B. squamosa*), gray-mold neck rot (*Botrytis alli*), and small sclerotial rot (*Botrytis squamosa*); various crops diseases: gray mold (*Botrytis cinerea*) and *sclerotinia* rot (*Sclerotinia sclerotiorum*); Japanese radish diseases: alternaria leaf spot (*Alternaria brassicicola*); Turfgrass diseases: dollar spot (*Sclerotinia homoeocarpa*) and brown patch and large patch (*Rhizoctonia solani*); and Banana diseases: Sigatoka disease (*Mycosphaerella fijiensis, Mycosphaerella musicola*).

Hemiptera: planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), and tarnished plant bug (*Lygus lineolaris*); whiteflies (Aleyrodidae) such as greenhouse whitefly (*Trialeurodes vaporariorum*) and silverleaf whitefly (*Bemisia argentifolii*); scales (Coccidae) such as California red scale (*Aonidiella aurantii*), San Jose scale (*Comstockaspis perniciosa*), citrus north scale (*Unaspis citri*), red wax scale (*Ceroplastes rubens*), and cottony cushion scale (*Icerya purchasi*); lace bugs (Tingidae); jumping plant lice (Homoptera, Psylloidea); and bed bugs (*Cimex lectularius*).

Lepidoptera: pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit *tortrix* (*Adoxophyes orana fasciata*), smaller tea *tortrix* (*Adoxophyes* sp.), oriental tea *tortrix* (*Homona magnanima*), apple *tortrix* (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); leaf miners (Gracillariidae) such as tea leafroller (*Caloptilia theivora*) and apple leafminer (*Phyllonorycter ringoneella*); codling moths (Carposimidae) such as peach fruit moth (*Carposina niponensis*); lyonetiid moths (Lyonetiidae) such as *Lyonetia* spp.; tussock moths (Lymantriidae) such as *Lymantria* spp. and *Euproctis* spp.; yponomeutid moths (Yponomeutidae) such as diamondback (*Plutella xylostella*); gelechild moths (Gelechiidae) such as pink bollworm (*Pectinophora gossypiella*) and potato tubeworm (*Phthorimaea operculella*); tiger moths and allies (Arctiidae) such as fall webworm (*Hyphantria cunea*); and tineid moths (Tineidae) such as casemaking clothes moth (*Tinea translucens*), and webbing clothes moth (*Tineola bisselliella*).

Thysanoptera: yellow citrus *thrips* (*Frankliniella occidentalis*), melon *thrips* (*Thrips palmi*), yellow tea *thrips* (*Scirtothrips dorsalis*), onion *thrips* (*Thrips tabaci*), flower *thrips* (*Frankliniella intonsa*), and tobacco *thrips* (*Frankliniella fusca*).

Diptera: houseflies (*Musca domestica*), common mosquito (*Culex pipiens pallens*), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Mediterranean fruit fly (*Ceratitis capitata*), and legume leafminer (*Liriomyza trifolii*).

Coleoptera: twenty-eight-spotted ladybirds (*Epilachna vigintioctopunctata*), cucurbit leaf beetle (*Aulacophora femoralis*), yellow striped flea beetle (*Phyllotreta striolata*), rice leaf beetle (*Oulema oryzae*), rice curculio (*Echinocnemus squameus*), rice water weevil; (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*).

Orthoptera: asiatic locusts (*Locusta migratoria*), African mole cricket (*Gryllotalpa africana*), rice grasshopper (*Oxya yezoensis*), and rice grasshopper (*Oxya japonica*).

Hymenoptera: cabbage sawflies (*Athalia rosae*), leafcutting ant (*Acromyrmex* spp.), and fire ant (*Solenopsis* spp.).

Nematodes: white-tip nematode (*Aphelenchoides besseyi*), strawberry bud nematode (*Nothotylenchus acris*), soybean cyst nematode (*Heterodera glycines*), southern root-knot nematode (*Meloidogyne incognita*), cobb's root-lesion nematode (*Pratylenchus penetrans*), and false root-knot nematode (*Nacobbus aberrans*).

Blattariae: German cockroach (*Blattella germanica*), smoky-brown cockroach (*Periplaneta fuliginosa*), American cockroach (*Periplaneta americana*), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus citri*), and *Oligonychus* spp.); Eriophyidae (for example, pink citrus rust mite (*Aculops pelekassi*)); Tarsonemidae (for example, broad mite (*Polyphagotarsonemus latus*)); Tenuipalpidae; Tuckerellidae; Tuckerellidae Acaridae (for example, common grain mite (*Tyrophagus putrescentiae*)); Pyroglyphidae (for example, Americal house dust mite (*Dermatophagoides farinae*) and house dust mite (*Dermatophagoides ptrenyssnus*)); Cheyletidae (for example, cheyletid mite (*Cheyletus eruditus*), *Cheyletus malaccensis*, and *Cheyletus moorei*; and Dermanyssidae.

The formulation comprising the present compound or salts thereof can be used in the field relating to a treatment of livestock diseases or livestock industry, and can exterminate the living things or parasites which are parasitic on the inside and/or the outside of vertebrates such as human being, cow, sheep, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *Dermacentor* spp., *Ornithodoros* spp. (for example, *Ornithodoros moubata*), red mite (*Dermanyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Aedes* spp. (for example, Asian tiger mosquito (*Aedes albopictus*)), *Anopheles* spp., *Culex* spp., *Culicoides* spp., *Musca* spp., *Hypoderma* spp., *Gasterophilus* spp., *Haematobia* spp., *Tabanus* spp., *Simulium* spp., *Triatoma* spp., lice (Phthiraptera) (for example, *Damalinia* spp.), *Linognathus* spp., *Haematopinus* spp., *Ctenocephalides* spp. (for example, cat flea (*Ctenocephalides felis*)) *Xenosylla* spp., Pharaoh's ant (*Monomorium pharaonis*) and nematodes [for example, hairworm (for example, *Nippostrongylus brasiliensis*, *Trichostrongylus axei*, *Trichostrongylus colubriformis*), *Trichinella* spp. (for example, *Trichinella spiralis*), barber pole worm (*Haemonchus contortus*), *Nematodirus* spp. (for example, *Nematodirus battus*), *Ostertagia circumcincta*, *Cooperia* spp., *Hymenolepis nana*, and the like.

EXAMPLES

The present invention will be described in more detail below by way of Production Examples, Formulation Examples, and Test Examples, but the present invention is not limited to these Examples.

First, Production Examples will be described.

Production Example 1

A mixture of 1 mmol (0.3 g) of 1-(2-bromomethyl-3-methoxyphenyl)-4-methyl-1,4-dihydro-tetrazol-5-one, 1 mmol (0.2 g) of 3-(2-chlorophenyl)-1-methyl-1H-pyrazol-5-ol, 1.3 mmol (0.18 g) of potassium carbonate, and 20 ml of acetonitrile was stirred with heating under reflux for 7 hours. The reaction mixture was cooled to room temperature and filtered, and then the filtrate was concentrated under reduced pressure and subjected to silica gel chromatography to obtain 0.25 g of 1-{2-[5-(2-chlorophenyl)-2-methyl-2H-pyrazol-3-yloxymethyl]-3-methoxyphenyl}-4-methyl-1,4-dihydro-tetrazol-5-one (hereinafter referred to as the present compound 1).

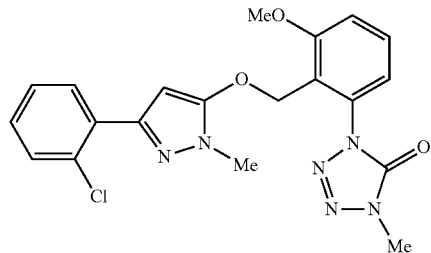 [SMILES: COc1cccc(-n2nnn(C)c2=O)c1COc1cc(-c2ccccc2Cl)nn1C]

$^1$H-NMR (CDCl$_3$) δ: 7.76 (1H, dd, J=7.6, 1.7 Hz), 7.50 (1H, t, J=8.2 Hz), 7.40 (1H, dd, J=7.9, 1.3 Hz), 7.29-7.19 (2H, m), 7.10 (1H, d, J=8.5 Hz), 7.07 (1H, d, J=8.0 Hz), 6.13 (1H, s), 5.31 (2H, s), 3.94 (3H, s), 3.65 (3H, s), 3.54 (3H, s).

Production Example 2

The same reaction was carried out, except that 3-(2-chlorophenyl)-1-methyl-1H-pyrazol-5-ol of Production Example 1 was replaced by 3-(3-chlorophenyl)-1-methyl-1H-pyrazol-5-ol, the present compound 2 was obtained.

Production Example 3

The same reaction was carried out, except that 3-(2-chlorophenyl)-1-methyl-1H-pyrazol-5-ol of Production Example 1 was replaced by 3-(4-chlorophenyl)-1-methyl-1H-pyrazol-5-ol, the present compound 3 was obtained.

Production Example 4

The same reaction was carried out, except that 3-(2-chlorophenyl)-1-methyl-1H-pyrazol-5-ol of Production Example 1 and 1-(2-bromomethyl-3-methoxyphenyl)-4-methyl-1,4-dihydro-tetrazol-5-one were respectively replaced by 3-(4-chlorophenyl)-1-methyl-1H-pyrazol-5-ol and 1-(2-bromomethyl-3-methylphenyl)-4-methyl-1,4-dihydrotetrazol-5-one, the present compound 4 was obtained.

Production Example 5

The same reaction was carried out, except that 3-(2-chlorophenyl)-1-methyl-1H-pyrazol-5-ol of Production Example 1 was replaced by 3-(3-chlorophenyl)-1-ethyl-1H-pyrazol-5-ol, the present compound 5 was obtained.

Production Example 6

The same reaction was carried out, except that 3-(2-chlorophenyl)-1-methyl-1H-pyrazol-5-ol of Production Example 1 and 1-(2-bromomethyl-3-methoxyphenyl)-4-methyl-1,4-dihydro-tetrazol-5-one were respectively replaced by 3-(3-chlorophenyl)-1-ethyl-1H-pyrazol-5-ol and 1-(2-bromomethyl-3-methylphenyl)-4-methyl-1,4-dihydrotetrazol-5-one, the present compound 6 was obtained.

Production Example 7

The same reaction was carried out, except that 3-(2-chlorophenyl)-1-methyl-1H-pyrazol-5-ol of Production Example 1 was replaced by 3-(4-chlorophenyl)-1,4-dimethyl-1H-pyrazol-5-ol, the present compound 7 was obtained.

Production Example 8

The same reaction was carried out, except that 3-(2-chlorophenyl)-1-methyl-1H-pyrazol-5-ol of Production Example 1 and 1-(2-bromomethyl-3-methoxyphenyl)-4-methyl-1,4-dihydro-tetrazol-5-one were respectively replaced by 3-phenyl-1,4-dimethyl-1H-pyrazol-5-ol and 1-(2-bromomethyl-3-methylphenyl)-4-methyl-1,4-dihydro-tetrazol-5-one, the present compound 8 was obtained.

Production Example 9

The same reaction was carried out, except that 3-(2-chlorophenyl)-1-methyl-1H-pyrazol-5-ol of Production Example 1 and 1-(2-bromomethyl-3-methoxyphenyl)-4-methyl-1,4-dihydro-tetrazol-5-one were replaced by 3-(4-chlorophenyl)-1-ethyl-1H-pyrazol-4-ol and 1-(2-bromomethyl-3-methylphenyl)-4-methyl-1,4-dihydrotetrazol-5-one, the present compound 9 was obtained.

Production Example 10

The same reaction was carried out, except that 3-(2-chlorophenyl)-1-methyl-1H-pyrazol-5-ol of Production Example 1 and 1-(2-bromomethyl-3-methoxyphenyl)-4-methyl-1,4-dihydro-tetrazol-5-one were respectively replaced by 2-phenylthiazol-4-one and 1-(2-bromomethyl-3-methylphenyl)-4-methyl-1,4-dihydrotetrazol-5-one, the present compound 10 was obtained.

Production Example 11

The same reaction was carried out, except that 3-(2-chlorophenyl)-1-methyl-1H-pyrazol-5-ol of Production Example 1 and 1-(2-bromomethyl-3-methoxyphenyl)-4-methyl-1,4-dihydro-tetrazol-5-one were respectively replaced by 1-methyl-4-(4-chlorophenyl)-1,3-dihydroimidazol-2-one and 1-(2-bromomethyl-3-methylphenyl)-4-methyl-1,4-dihydrotetrazol-5-one, the present compound 11 was obtained.

The structural formulas of the present compounds obtained in Production Examples 2 to 11 and $^1$H-NMR data thereof are shown below.

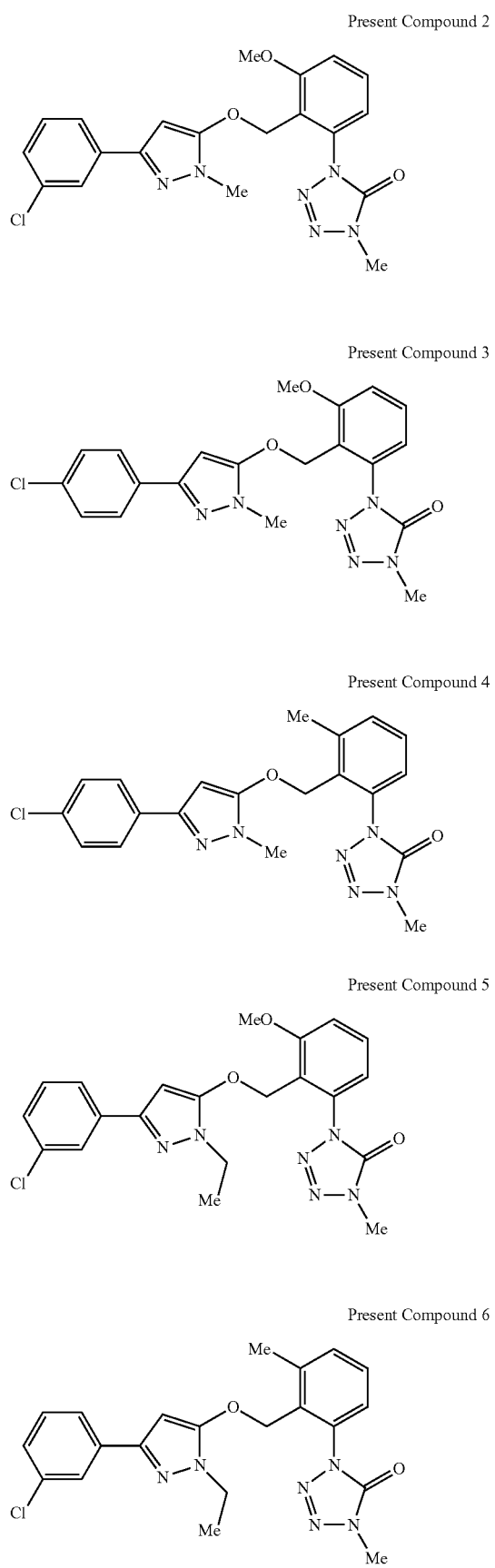
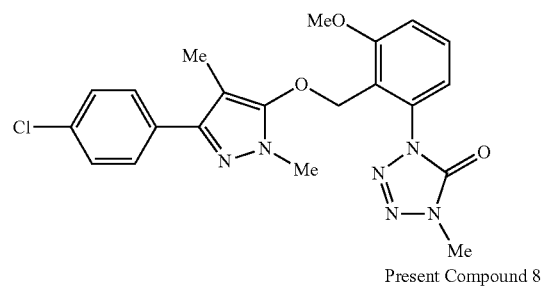
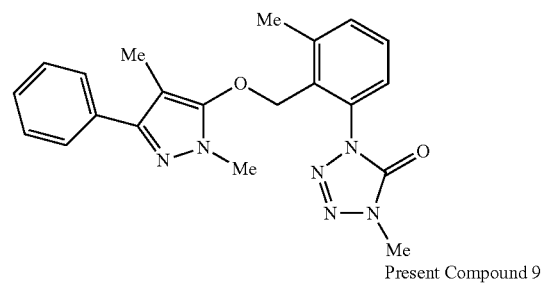
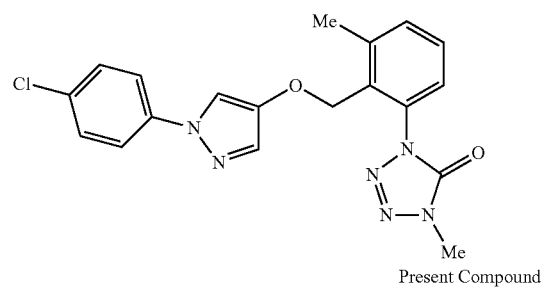
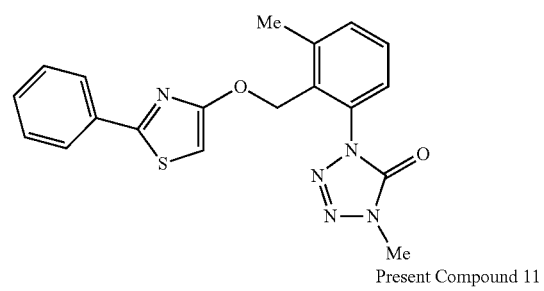
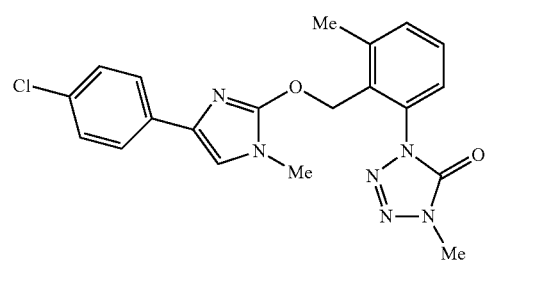
Present Compound 2
$^1$H-NMR (CDCl$_3$) δ: 7.44 (1H, t, J=8.2 Hz), 7.37-7.28 (3H, m), 7.07 (1H, d, J=8.0 Hz), 7.02 (1H, d, J=8.0 Hz), 6.69 (2H, d, J=3.6 Hz), 5.33 (2H, s), 3.92 (3H, s), 3.67 (3H, s), 1.88 (3H, s).
Present Compound 3
$^1$H-NMR (CDCl$_3$) δ: 7.67-7.63 (2H, m), 7.51 (1H, t, J=8.2 Hz), 7.33 (2H, dt, J=8.8, 2.2 Hz), 7.11 (1H, d, J=8.5 Hz), 7.09-7.07 (1H, m), 5.84 (1H, s), 5.29 (2H, s), 3.94 (3H, s), 3.62 (3H, s), 3.52 (3H, s).

Present Compound 4

¹H-NMR (CDCl₃) δ: ¹H-NMR (CDCl₃) δ: 7.67-7.64 (2H, m), 7.49-7.42 (2H, m), 7.36-7.29 (3H, m), 5.80 (1H, s), 5.14 (2H, s), 3.64 (3H, s), 3.58 (3H, s), 2.53 (3H, s).

Present Compound 5

¹H-NMR (CDCl₃) δ: ¹H-NMR (CDCl₃) δ: 7.74 (1H, t, J=1.7 Hz), 7.61-7.59 (1H, m), 7.52 (1H, t, J=8.2 Hz), 7.31-7.22 (2H, m), 7.11 (1H, d, J=8.5 Hz), 7.09 (1H, d, J=8.0 Hz), 5.85 (1H, s), 5.28 (2H, s), 3.94 (3H, s), 3.88 (2H, q, J=7.2 Hz), 3.63 (3H, s), 1.29 (3H, t, J=7.2 Hz).

Present Compound 6

¹H-NMR (CDCl₃) δ: 7.75 (1H, t, J=1.8 Hz), 7.61 (1H, dt, J=7.6, 1.5 Hz), 7.49-7.42 (2H, m), 7.32-7.23 (3H, m), 5.82 (1H, s), 5.13 (2H, s), 3.94 (2H, q, J=7.2 Hz), 3.65 (3H, s), 2.53 (3H, s), 1.32 (3H, t, J=7.2 Hz).

Present Compound 7

¹H-NMR (CDCl₃) δ: 7.57-7.50 (3H, m), 7.37-7.34 (2H, m), 7.09 (2H, dd, J=8.2, 1.9 Hz), 5.23 (2H, s), 3.88 (3H, s), 3.63 (3H, s), 3.51 (3H, s), 1.96 (3H, s).

Present Compound 8

¹H-NMR (CDCl₃) δ: 7.46-7.36 (5H, m), 7.28-7.24 (3H, m), 5.28 (2H, s), 3.69 (3H, s), 3.57 (3H, s), 2.58 (3H, s), 1.75 (3H, s).

Present Compound 9

¹H-NMR (CDCl₃) δ: 7.56-7.52 (2H, m), 7.49 (1H, d, J=1.0 Hz), 7.44-7.37 (5H, m), 7.28-7.26 (1H, m), 4.99 (2H, s), 3.66 (3H, s), 2.51 (3H, s).

Present Compound 10

¹H-NMR (CDCl₃) δ: 7.90-7.87 (2H, m), 7.42-7.38 (5H, m), 7.26-7.23 (1H, m), 6.11 (1H, s), 5.35 (2H, s), 3.59 (3H, s), 2.57 (3H, s).

Present Compound 11

¹H-NMR (CDCl₃) δ: 7.57 (2H, dt, J=8.8, 2.1 Hz), 7.39-7.44 (2H, m), 7.29 (2H, dt, J=8.9, 2.2 Hz), 7.24 (1H, dd, J=6.0, 3.1 Hz), 6.74 (1H, s), 5.50 (2H, s), 3.57 (3H, s), 3.30 (3H, s), 2.60 (3H, s).

Production Example 12

A mixture of 0.85 g of 5-{[2-(4,5-dihydro-4-methyl-5-oxo-1H-tetrazol-1-yl)-6-methylphenyl]methyloxy}-3-bromo-1,2,4-thiadiazole, 0.36 g of 4-chlorophenylboronic acid, 0.19 g of [1,1'-bis(diphenylphosphino)ferrocene]palladium(II) dichloride dichloromethane adduct, 0.63 of potassium carbonate, 10 mL of dimethoxyethane, and 1 mL of water was heated under reflux for 5 hours. To the reaction mixture, a saturated sodium bicarbonate solution was added and the mixture was extracted with ethyl acetate. The organic layer was washed with water and a saturated sodium bicarbonate solution, dried over anhydrous sodium sulfate, and then concentrated under reduced pressure. The residue thus obtained was subjected to silica gel column chromatography to obtain 0.07 g of 1-(2-{[3-(4-chlorophenyl)-1,2,4-thiadiazol-5-yl]oxymethyl}-3-methylphenyl)-4-methyl-1,4-dihydrotetrazol-5-one (hereinafter referred to as the present compound 12).

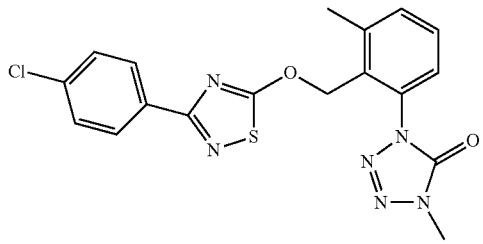 [SMILES: Cc1cccc(-n2nnn(C)c2=O)c1COc1nc(-c2ccc(Cl)cc2)ns1]

¹H-NMR (CDCl₃) δ: 2.58 (3H, s), 3.63 (3H, s), 5.67 (2H, s), 7.30 (1H, dd, J=7.5, 1.6 Hz), 7.41-7.43 (3H, m), 7.47 (1H, t, J=7.6 Hz), 8.09 (2H, dt, J=9.0, 2.2 Hz).

Production Example 13

To a mixture of 1.97 g of triphenylphosphine and 20 mL of tetrahydrofuran, 3.4 mL of diethyl azodicarboxylate (40% toluene solution) was added under ice cooling. Under ice cooling, after further stirring for 10 minutes, 1.10 g of 1-(2-(hydroxymethyl)-3-methylphenyl)-4-methyl-1,4-dihydrotetrazol-5-one was added. Under ice cooling, after further stirring for 10 minutes, 0.75 g of 2(5H)-thiophenone was added, followed by stirring at room temperature for 5 hours. To the reaction mixture, a saturated sodium bicarbonate solution was added and the mixture was extracted with ethyl acetate. The organic layer was washed with water and a saturated sodium bicarbonate solution, dried over anhydrous sodium sulfate, and then concentrated under reduced pressure. The residue thus obtained was subjected to silica gel column chromatography to obtain 0.60 g of 1-[2-(thiophen-2-yloxymethyl)-3-methylphenyl]-4-methyl-1,4-dihydrotetrazol-5-one (hereinafter referred to as the present compound 13).

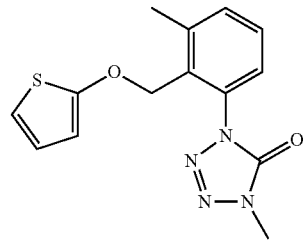 [SMILES: Cc1cccc(-n2nnn(C)c2=O)c1COc1cccs1]

¹H-NMR (CDCl₃) δ: 2.51 (3H, s), 3.68 (3H, s), 5.08 (2H, s), 6.20 (1H, dd, J=3.8, 1.5 Hz), 6.55 (1H, dd, J=5.7, 1.6 Hz), 6.67 (1H, dd, J=5.8, 3.8 Hz), 7.27-7.28 (1H, m), 7.38 (1H, dd, J=7.7, 1.5 Hz), 7.42 (1H, t, J=7.6 Hz).

Production Example 14

To a mixture of 0.60 g of 1-[2-(thiophen-2-yloxymethyl)-3-methylphenyl]-4-methyl-1,4-dihydrotetrazol-5-one and 10 mL of chloroform, 0.35 g of N-bromosuccinimide was added under ice cooling. Under ice cooling, after stirring for 1 hour, a saturated sodium bicarbonate solution was added to the reaction mixture, and the mixture was extracted with ethyl acetate. The organic layer was washed with water and a saturated sodium bicarbonate solution, dried over anhydrous sodium sulfate, and then concentrated under reduced pressure to obtain 0.68 g of 1-[2-(5-bromothiophen-2-yloxymethyl)-3-methylphenyl]-4-methyl-1,4-dihydrotetrazol-5-one (hereinafter referred to as the present compound 14).

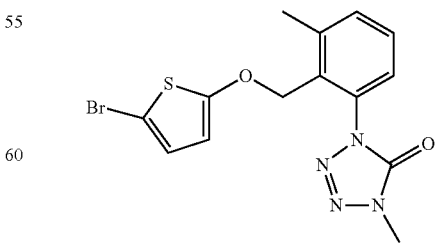

1H-NMR (CDCl3) δ: 2.49 (3H, s), 3.70 (3H, s), 5.05 (2H, s), 5.97 (1H, d, J=3.9 Hz), 6.65 (1H, d, J=4.1 Hz), 7.27-7.28 (1H, m), 7.39 (1H, d, J=6.6 Hz), 7.43 (1H, t, J=7.6 Hz).

Production Example 15

A mixture of 0.34 g of 1-[2-(5-bromothiophen-2-yloxymethyl)-3-methylphenyl]-4-methyl-1,4-dihydrotetrazol-5-one, 0.18 g of 4-chlorophenylboronic acid, 0.10 g of tetrakis(triphenylphosphine)palladium, 0.26 of sodium carbonate, 5 mL of dimethoxyethane, and 5 mL of water was heated at 100° C. for 5 hours. To the reaction mixture, a saturated sodium bicarbonate solution was added and the mixture was extracted with ethyl acetate. The organic layer was washed with water and a saturated sodium bicarbonate solution, dried over anhydrous sodium sulfate, and then concentrated under reduced pressure. The residue thus obtained was subjected to silica gel column chromatography to obtain 0.19 g of 1-{2-[5-(4-chlorophenyl)thiophen-2-yloxymethyl]-3-methylphenyl}-4-methyl-1,4-dihydrotetrazol-5-one (hereinafter referred to as the present compound 15).

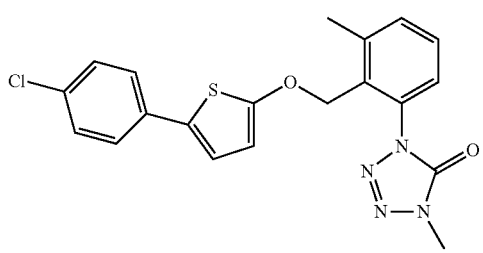 [SMILES: Cc1cccc(-n2nnn(C)c2=O)c1COc1ccc(-c2ccc(Cl)cc2)s1]

¹H-NMR (CDCl₃) δ: 2.53 (3H, s), 3.67 (3H, s), 5.12 (2H, s), 6.18 (1H, d, J=3.9 Hz), 6.89 (1H, d, J=4.1 Hz), 7.26-7.30 (3H, m), 7.39-7.42 (4H, m).

Production Example 16

A mixture of 0.11 g of 4-(2-methoxyphenyl)-4-oxazolin-2-one, 0.16 g of 1-(2-bromomethyl-3-methylphenyl)-4-methyl-1,4-dihydrotetrazol-5-one, 0.16 g of potassium carbonate, and 5 mL of N,N-dimethylformamide was stirred at room temperature for 3 hours. To the reaction mixture, water was added and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 0.05 g of 1-(2-{[4-(2-methoxyphenyl)-1,3-oxazol-2-yloxy]methyl}-3-methylphenyl)-4-methyl-1,4-dihydrotetrazol-5-one (hereinafter referred to as the present compound 16).

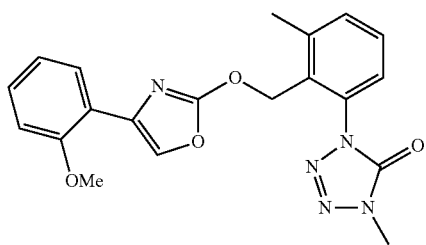 [SMILES: COc1ccccc1-c1coc(OCc2c(C)cccc2-n2nnn(C)c2=O)n1]

¹H-NMR (CDCl₃) δ: 7.97-7.95 (1H, m), 7.68 (1H, s), 7.59-7.57 (1H, m), 7.41-7.38 (2H, m), 7.28-7.25 (1H, m), 7.07-7.03 (1H, m), 6.93-6.91 (1H, m), 5.56 (2H, s), 3.91 (3H, s), 3.62 (3H, s), 2.59 (3H, s).

Production Example 17

The same reaction was carried out, except that 4-(2-methoxyphenyl)-4-oxazolin-2-one of Production Example 16 was replaced by 4-(4-chlorophenyl)-4-oxazolin-2-one, 1-(2-{[4-(4-chlorophenyl)-1,3-oxazol-2-yloxy]methyl}-3-methylphenyl)-4-methyl-1,4-dihydrotetrazol-5-one (hereinafter referred to as the present compound 17) was obtained.

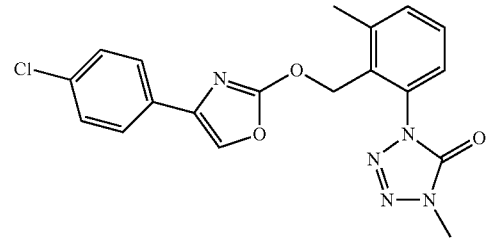 [SMILES: Cc1cccc(-n2nnn(C)c2=O)c1COc1nc(-c2ccc(Cl)cc2)co1]

1H-NMR (CDCl3) δ: 7.55 (2H, d, J=8.7 Hz), 7.44-7.40 (3H, m), 7.34 (2H, d, J=8.7 Hz), 7.29-7.26 (1H, m), 5.54 (2H, s), 3.63 (3H, s), 2.58 (3H, s).

Production Example 18

The same reaction was carried out, except that 4-(2-methoxyphenyl)-4-oxazolin-2-one of Production Example 16 was replaced by 4-(4-methoxyphenyl)-4-oxazolin-2-one, 1-(2-{[4-(4-methoxyphenyl)-1,3-oxazol-2-yloxy]methyl}-3-methylphenyl)-4-methyl-1,4-dihydrotetrazol-5-one (hereinafter referred to as the present compound 18) was obtained.

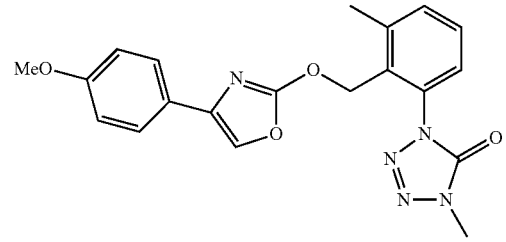 [SMILES: COc1ccc(-c2coc(OCc3c(C)cccc3-n3nnn(C)c3=O)n2)cc1]

¹H-NMR (CDCl₃) δ: 7.55 (2H, d, J=8.8 Hz), 7.43-7.39 (2H, m), 7.35 (1H, s), 7.28-7.25 (1H, m), 6.91 (2H, d, J=8.8 Hz), 5.54 (2H, s), 3.82 (3H, s), 3.61 (3H, s), 2.58 (3H, s).

Production Example 19

The same reaction was carried out, except that 4-(2-methoxyphenyl)-4-oxazolin-2-one of Production Example 16 was replaced by 4-(3-chlorophenyl)-4-oxazolin-2-one, 1-(2-{[4-(3-chlorophenyl)-1,3-oxazol-2-yloxy]methyl}-3-methylphenyl)-4-methyl-1,4-dihydrotetrazol-5-one (hereinafter referred to as the present compound 19) was obtained.

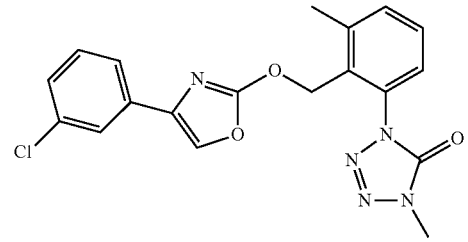 [SMILES: Cc1cccc(-n2nnn(C)c2=O)c1COc1nc(-c2cccc(Cl)c2)co1]

¹H-NMR (CDCl₃) δ: 7.62-7.60 (1H, m), 7.46-7.45 (1H, m), 7.40-7.38 (1H, m), 7.34-7.32 (3H, m), 7.26-7.24 (1H, m), 7.22-7.20 (1H, m), 5.55 (2H, s), 3.63 (3H, s), 2.57 (3H, s).

Production Example 20

The same reaction was carried out, except that 4-(2-methoxyphenyl)-4-oxazolin-2-one of Production Example 16 was replaced by 4-phenyl-4-oxazolin-2-one, 1-{2-[(4-phenyl-1,3-oxazol-2-yloxy)methyl]-3-methylphenyl}-4-methyl-1,4-dihydrotetrazol-5-one (hereinafter referred to as the present compound 20) was obtained.

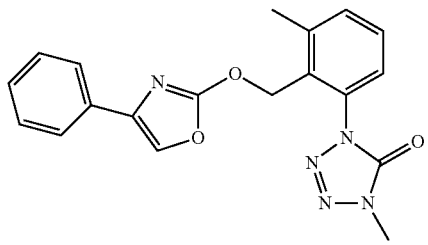

$^1$H-NMR (CDCl$_3$) δ: 7.62-7.60 (2H, m), 7.43 (1H, s), 7.38-7.34 (4H, m), 7.27-7.24 (2H, m), 5.55 (2H, s), 3.58 (3H, s), 2.56 (3H, s).

Production Example 21

The same reaction was carried out, except that 4-(2-methoxyphenyl)-4-oxazolin-2-one of Production Example 16 was replaced by 4-(4-cyanophenyl)-4-oxazolin-2-one, 1-(2-{[4-(4-cyanophenyl)-1,3-oxazol-2-yloxy]methyl}-3-methylphenyl)-4-methyl-1,4-dihydrotetrazol-5-one (hereinafter referred to as the present compound 21) was obtained.

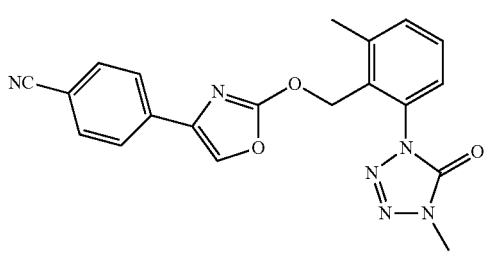

$^1$H-NMR (CDCl$_3$) δ: 7.72 (2H, d, J=8.7 Hz), 7.65 (2H, d, J=8.7 Hz), 7.56 (1H, s), 7.44-7.40 (2H, m), 7.30-7.27 (1H, m), 5.55 (2H, s), 3.65 (3H, s), 2.59 (3H, s).

Production Example 22

A mixture of 0.4 g of 4-phenyl-4-oxazoline-2-thione, 0.58 g of 1-(2-bromomethyl-3-methyl-phenyl)-4-methyl-1,4-dihydrotetrazol-5-one, 0.62 g of potassium carbonate, and 10 mL of N,N-dimethylformamide was stirred at room temperature for 2 hours. To the reaction mixture, water was added and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 0.58 g of 1-{2-[(4-phenyl-1,3-oxazol-2-ylthio)methyl]-3-methylphenyl}-4-methyl-1,4-dihydrotetrazol-5-one (hereinafter referred to as the present compound 22).

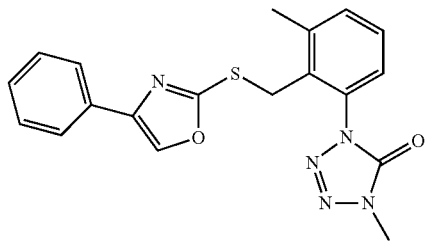 [SMILES: Cc1cccc(-n2nnn(C)c2=O)c1COc1nc(-c2ccccc2)co1]

$^1$H-NMR (CDCl$_3$) δ: 7.86 (1H, s), 7.70-7.67 (2H, m), 7.41-7.37 (2H, m), 7.33-7.29 (3H, m), 7.21-7.19 (1H, m), 4.58 (2H, s), 3.54 (3H, s), 2.52 (3H, s).

Production Example 23

The same reaction was carried out, except that 4-phenyl-4-oxazoline-2-thione of Production Example 22 was replaced by 4-(4-chlorophenyl)-4-oxazoline-2-thione, 1-(2-{[4-(4-chlorophenyl)-1,3-oxazol-2-ylthio]methyl}-3-methylphenyl)-4-methyl-1,4-dihydrotetrazol-5-one (hereinafter referred to as the present compound 23) was obtained.

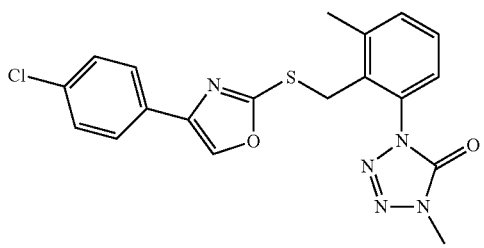

$^1$H-NMR (CDCl$_3$) δ: 7.85 (1H, s), 7.61 (2H, d, J=8.4 Hz), 7.36-7.32 (4H, m), 7.21-7.19 (1H, m), 4.56 (2H, s), 3.57 (3H, s), 2.52 (3H, s).

Production Example 24

The same reaction was carried out, except that 4-phenyl-4-oxazoline-2-thione of Production Example 22 was replaced by 4-(3-chlorophenyl)-4-oxazoline-2-thione, 1-(2-{[4-(3-chlorophenyl)-1,3-oxazol-2-ylthio]methyl}-3-methylphenyl)-4-methyl-1,4-dihydrotetrazol-5-one (hereinafter referred to as the present compound 24) was obtained.

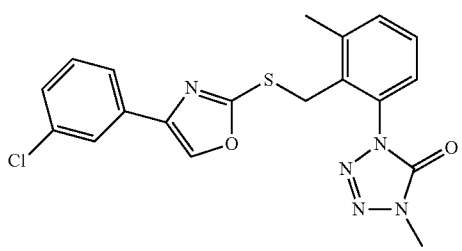 [SMILES: Cc1cccc(-n2nnn(C)c2=O)c1CSc1nc(-c2cccc(Cl)c2)co1]

$^1$H-NMR (CDCl$_3$) δ: 7.88 (1H, s), 7.70-7.69 (1H, m), 7.57-7.55 (1H, m), 7.37-7.27 (4H, m), 7.23-7.21 (1H, m), 4.57 (2H, s), 3.62 (3H, s), 2.56 (3H, s).

Production Example 25

A mixture of 1.05 g of 5-(4-chlorophenyl)-1,2-dihydro-1-methyl-3H-pyrazol-3-one (synthesized in accordance with the process mentioned in CN102584705 A), 1.35 g of 1-(2-bromomethyl-3-methylphenyl)-4-methyl-1,4-dihydro-tetrazol-5-one, 1.34 g of potassium carbonate, and 20 mL of acetonitrile was stirred with heating under reflux for 3 hours. To the reaction mixture allowed to cool, water was added and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 1.48 g of 1-(2-{[1-methyl-5-(4-chlorophenyl)-1H-pyrazol-3-yloxy]methyl}-3-methylphenyl)-4-methyl-1,4-dihydrotet-razol-5-one (hereinafter referred to as the present compound 25).

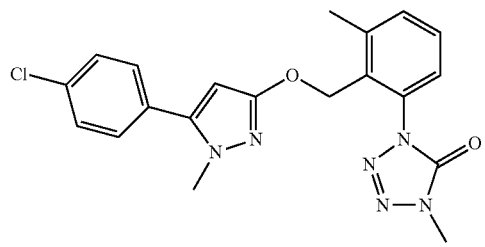 [SMILES: Cc1cccc(-n2nnn(C)c2=O)c1COc1cc(-c2ccc(Cl)cc2)n(C)n1]

$^1$H-NMR (CDCl$_3$) δ: 7.39-7.36 (4H, m), 7.29-7.25 (3H, m), 5.62 (1H, s), 5.22 (2H, s), 3.68 (3H, s), 3.65 (3H, s), 2.55 (3H, s).

Production Example 26

A mixture of 0.30 g of 1-{2-[4-bromo-1,3-thiazol-2-yloxymethyl]-3-methylphenyl}-4-methyl-1,4-dihydrotetra-zol-5-one, 0.11 g of phenylboronic acid, 0.34 g of tripotassium phosphate, 0.5 mL of water, 0.07 g of [1,1'-bis(diphenylphosphino)ferrocene]palladium(II) dichloride dichloromethane adduct, and 5 mL of 1,2-dimethoxyethane was stirred with heating under reflux for 1 hour. After cooling, the reaction solution was filtered through Cerite and the filtrate was concentrated under reduced pressure. The residue thus obtained was subjected to silica gel column chromatography to obtain 0.21 g of 1-{2-[(4-phenyl-1,3-thiazol-2-yloxy)methyl]-3-methylphenyl}-4-methyl-1,4-di-hydrotetrazol-5-one (hereinafter referred to as the present compound 26).

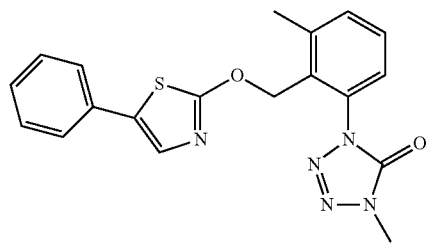 [SMILES: Cc1cccc(-n2nnn(C)c2=O)c1COc1ncc(-c2ccccc2)s1]

$^1$H-NMR (CDCl$_3$) δ: 7.41-7.38 (4H, m), 7.34-7.31 (2H, m), 7.29-7.24 (3H, m), 5.49 (2H, s), 3.69 (3H, s), 2.54 (3H, s).

Production Example 27

The same reaction was carried out, except that phenyl-boronic acid of Production Example 26 was replaced by 2-methoxyphenylboronic acid, 1-(2-{[4-(2-methoxyphe-nyl)-1,3-thiazol-2-yloxy]methyl}-3-methylphenyl)-4-methyl-1,4-dihydrotetrazol-5-one (hereinafter referred to as the present compound 27) was obtained.

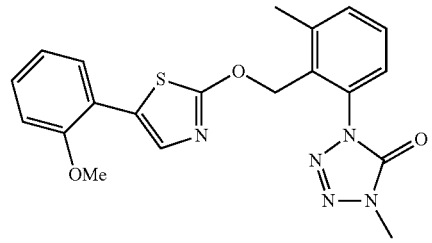 [SMILES: COc1ccccc1-c1cnc(OCc2c(C)cccc2-n2nnn(C)c2=O)s1]

$^1$H-NMR (CDCl$_3$) δ: 7.48-7.44 (2H, m), 7.41-7.36 (2H, m), 7.28-7.20 (2H, m), 6.97-6.90 (2H, m), 5.49 (2H, s), 3.86 (3H, s), 3.68 (3H, s), 2.53 (3H, s).

Production Example 28

The same reaction was carried out, except that phenyl-boronic acid of Production Example 26 was replaced by 4-methoxyphenylboronic acid, 1-(2-{[4-(4-methoxyphe-nyl)-1,3-thiazol-2-yloxy]methyl}-3-methylphenyl)-4-methyl-1,4-dihydrotetrazol-5-one (hereinafter referred to as the present compound 28) was obtained.

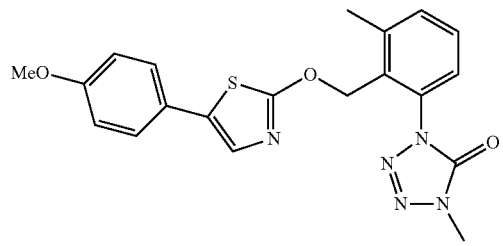 [SMILES: COc1ccc(-c2cnc(OCc3c(C)cccc3-n3nnn(C)c3=O)s2)cc1]

$^1$H-NMR (CDCl$_3$) δ: 7.41-7.37 (2H, m), 7.31 (2H, d, J=8.9 Hz), 7.28-7.26 (1H, m), 7.11 (1H, s), 6.86 (2H, d, J=8.9 Hz), 5.47 (2H, s), 3.79 (3H, s), 3.68 (3H, s), 2.53 (3H, s).

Production Example 29

A mixture of 0.4 g of 5-(4-chlorophenyl)-1,2-dihydro-1,4-dimethyl-3H-pyrazol-3-one (synthesized in accordance with the process mentioned in International Publication WO CN102584705 A), 0.51 g of 1-(2-bromomethyl-3-methyl-phenyl)-4-methyl-1,4-dihydro-tetrazol-5-one, 0.5 g of potassium carbonate and 10 mL of acetonitrile was stirred with heating under reflux for 3 hours. To the reaction mixture allowed to cool, water was added and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 0.6 g of 1-(2-{[1,4-dimethyl-5-(4-chlorophenyl)-1H-pyrazol-3-yloxy]methyl}-3-methylphenyl)-4-methyl-1,4-dihydrotetrazol-5-one (hereinafter referred to as the present compound 29).

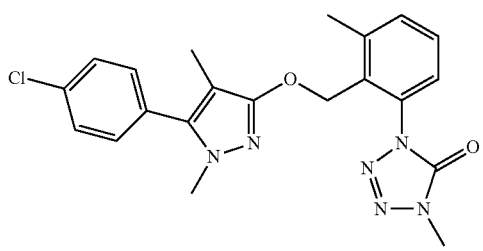 [SMILES: Cc1cccc(-n2nnn(C)c2=O)c1COc1nn(C)c(-c2ccc(Cl)cc2)c1C]

¹H-NMR (CDCl₃) δ: 7.43-7.37 (4H, m), 7.26-7.23 (1H, m), 7.20 (2H, d, J=8.6 Hz), 5.28 (2H, s), 3.69 (3H, s), 3.55 (3H, s), 2.58 (3H, s), 1.73 (3H, s).

Production Example 30

A mixture of 0.19 g of 5-(4-chlorophenyl)-1,3,4-thiadiazol-2-one, 0.23 g of 1-(2-bromomethyl-3-methylphenyl)-4-methyl-1,4-dihydro-tetrazol-5-one, 0.24 g of potassium carbonate, and 10 mL of acetonitrile was stirred with heating under reflux for 3 hours. To the reaction mixture allowed to cool, water was added and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 0.3 g of 1-(2-{[5-(4-chlorophenyl)-1,3,4-thiadiazol-2-yloxy]methyl}-3-methylphenyl)-4-methyl-1,4-dihydrotetrazol-5-one (hereinafter referred to as the present compound 30).

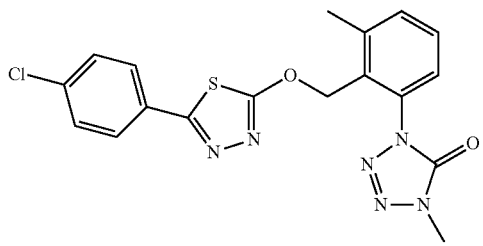 [SMILES: Cc1cccc(-n2nnn(C)c2=O)c1COc1nnc(-c2ccc(Cl)cc2)s1]

¹H-NMR (CDCl₃) δ: 7.65 (2H, d, J=8.6 Hz), 7.42-7.37 (4H, m), 7.25-7.23 (1H, m), 5.06 (2H, s), 3.74 (3H, s), 2.66 (3H, s).

With respect to the production of intermediates for the production of the above-mentioned present compounds, Reference Production Examples are shown below.

Reference Production Example 1

A mixture of 25.0 g of 1-bromo-2-methyl-3-aminobenzene, 60.0 g of triphosgene, and 400 ml of toluene was stirred with heating under reflux for 3 hours. The reaction mixture allowed to cool was concentrated under reduced pressure to obtain 30.3 g of 1-bromo-3-isocyanato-2-methylbenzene.

¹H-NMR (CDCl₃) δ(ppm): 2.42 (3H, s), 7.00 (1H, dt, J=0.5, 8.0 Hz), 7.05 (1H, dd, J=1.7, 8.0 Hz), 7.39 (1H, dd, J=1.5, 7.7 Hz).

Reference Production Example 2

A mixture of 15.0 g of 3-amino-1-methoxy-2-methylbenzene, 48.7 g of triphosgene, and 350 ml of toluene was stirred with heating under reflux for 3 hours. The reaction mixture allowed to cool was concentrated under reduced pressure to obtain 17.0 g of 1-methoxy-3-isocyanato-2-methylbenzene.

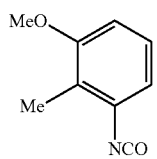

¹H-NMR (CDCl₃) δ(ppm): 2.19 (3H, s), 3.82 (3H, s), 6.69 (1H, d, J=8.2 Hz), 6.72 (1H, dd, J=0.5, 8.0 Hz), 7.09 (1H, t, J=8.2 Hz).

Reference Production Example 3

Under ice cooling, 21.9 g of anhydrous aluminum chloride was added to 250 mL of N,N-dimethylformamide, followed by stirring for 15 minutes. To this was added 10.7 g of sodium azide and, after stirring for 15 minutes, 25.0 g of 1-chloro-3-isocyanato-2-methylbenzene was added, followed by heating at 80° C. for 5 hours. After cooling, the reaction solution was added in a mixture of 35 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 17.0 g of 1-(2-methyl-3-chlorophenyl)-1,4-dihydrotetrazol-5-one.

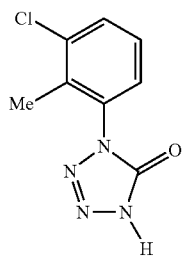 [SMILES: Cc1c(Cl)cccc1-n1nn[nH]c1=O]

¹H-NMR (CDCl₃) δ(ppm): 2.32 (3H, s), 7.28-7.36 (2H, m), 7.57 (1H, dd, J=6.8, 2.2 Hz), 13.08 (1H, s).

Reference Production Example 4

To a mixture of 10.00 g of 1-(2-methyl-3-chlorophenyl)-1,4-dihydrotetrazol-5-one mentioned in Reference Production Example 3 and 100 mL of N,N-dimethylformamide, 2.30 g of 60% sodium hydride was added under ice cooling. The temperature of the mixture was raised to room temperature, followed by stirring for 1 hour. To the reaction mixture, 3.2 mL of methyl iodide was added under ice cooling. The temperature of the mixture was raised to room temperature, followed by stirring for 14 hours. To the reaction mixture, water was added and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 1.56 g of 1-(2-methyl-3-chlorophenyl)-4-methyl-1,4-dihydrotetrazol-5-one.

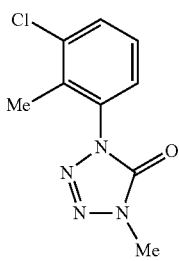

$^1$H-NMR (CDCl$_3$) δ(ppm): 2.30 (3H, s), 3.73 (3H, s), 7.27 (1H, d, J=2.7 Hz), 7.28 (1H, d, J=7.1 Hz), 7.52 (1H, dd, J=2.7, 6.8 Hz).

Reference Production Example 5

A mixture of 1.56 g of 1-(2-methyl-3-chlorophenyl)-4-methyl-1,4-dihydrotetrazol-5-one mentioned in Reference Production Example 4, 0.34 g of 1,1'-azobis(cyclohexane-1-carbonitrile), 1.42 g of N-bromosuccinimide, and 30 mL of chlorobenzene was stirred with heating under reflux for 5 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.94 g of 1-(2-bromomethyl-3-chlorophenyl)-4-methyl-1,4-dihydrotetrazol-5-one.

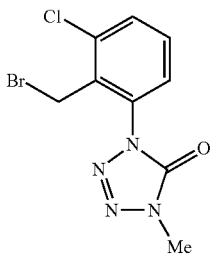 [SMILES: Cn1nnn(-c2cccc(Cl)c2CBr)c1=O]

$^1$H-NMR (CDCl$_3$) δ(ppm): 3.76 (3H, s), 4.69 (2H, s), 7.35 (1H, dd, J=1.2, 8.1 Hz), 7.43 (1H, t, J=8.1 Hz), 7.58 (1H, dd, J=1.2, 8.1 Hz).

Reference Production Example 6

Under ice cooling, 16.0 g of anhydrous aluminum chloride was added to 180 mL of N,N-dimethylformamide, followed by stirring for 15 minutes. To this was added 7.8 g of sodium azide and, after stirring for 15 minutes, 17.0 g of 1-methoxy-3-isocyanato-2-methylbenzene mentioned in Reference Production Example 4 was added, followed by heating at 80° C. for 4.5 hours. After cooling, the reaction solution added in a mixture of 25 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 16.2 g of 1-(2-methyl-3-methoxyphenyl)-1,4-dihydrotetrazol-5-one.

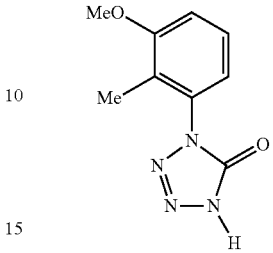

$^1$H-NMR (DMSO-d$_6$) δ(ppm): 1.99 (3H, s), 3.87 (3H, s), 7.01 (1H, d, J=8.1 Hz), 7.17 (1H, d, J=8.1 Hz). 7.36 (1H, t, J=8.3 Hz), 14.63 (1H, s).

Reference Production Example 7

To a mixture of 10.00 g of 1-(2-methyl-3-methoxyphenyl)-1,4-dihydrotetrazol-5-one mentioned in Reference Production Example 6 and 100 mL of N,N-dimethylformamide, 2.47 g of 60% sodium hydride was added under ice cooling. The temperature of the mixture was raised to room temperature, followed by stirring for 1 hour. To the reaction mixture, 3.5 mL of methyl iodide was added under ice cooling. The temperature of the mixture was raised to room temperature, followed by stirring for 14 hours. To the reaction mixture, water was added and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 2.19 g of 1-(2-methyl-3-methoxyphenyl)-4-methyl-1,4-dihydrotetrazol-5-one.

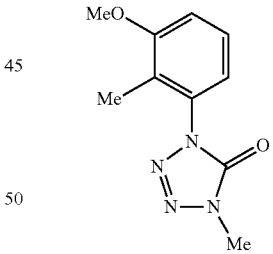

$^1$H-NMR (CDCl$_3$) δ(ppm): 2.11 (3H, s), 3.72 (3H, s), 3.88 (3H, s), 6.95 (1H, d, J=8.2 Hz), 6.98 (1H, d, J=8.5 Hz), 7.29 (1H, t, J=8.2 Hz)

Reference Production Example 8

A mixture of 2.19 g of 1-(2-methyl-3-methoxyphenyl)-4-methyl-1,4-dihydrotetrazol-5-one mentioned in Reference Production Example 7, 0.52 g of 1,1'-azobis(cyclohexane-1-carbonitrile), 2.16 g of N-bromosuccinimide, and 40 mL of chlorobenzene was stirred with heating under reflux for 5 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 2.36 g of 1-(2-bromomethyl-3-methoxyphenyl)-4-methyl-1,4-dihydrotetrazol-5-one.

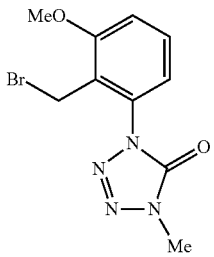 [SMILES: COc1cccc(-n2nnn(C)c2=O)c1CBr]

$^1$H-NMR (CDCl$_3$) δ(ppm): 3.74 (3H, s), 3.96 (3H, s), 4.93 (2H, s), 7.02 (1H, dd, J=1.0, 8.5 Hz), 7.04 (1H, d, J=9.0 Hz), 7.43 (1H, t, J=8.1 Hz).

Reference Production Example 9

To a mixture of 4.99 g of triisopropylsilanethiol and 30 mL of toluene, 0.63 g of 60% sodium hydride was added under ice cooling, followed by stirring for 30 minutes. To the reaction mixture, 2.82 g of 1-(2-methyl-3-bromophenyl)-4-methyl-1,4-dihydrotetrazol-5-one mentioned in Synthesis Example 10, and 0.856 g of [1,1'-bis(diphenylphosphino)ferrocene]palladium(II) dichloride dichloromethane adduct were added and the temperature of the reaction mixture was raised to 90° C., followed by stirring for 4 hours. After cooling, water was added to the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 3.64 g of 1-(2-methyl-3-triisopropylsilylthiophenyl)-4-methyl-1,4-dihydrotetrazol-5-one.

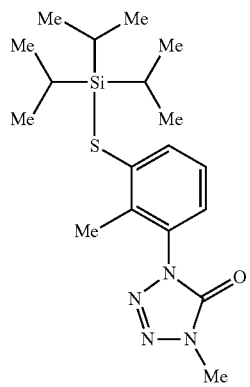 [SMILES: Cc1c(S[Si](C(C)C)(C(C)C)C(C)C)cccc1-n1nnn(C)c1=O]

$^1$H-NMR (CDCl$_3$) δ(ppm): 1.09 (18H, d, J=6.6 Hz), 1.31 (3H, q, J=6.6 Hz), 2.45 (3H, s), 3.71 (3H, s), 7.16-7.21 (2H, m), 7.64 (1H, dd, J=6.6, 2.7 Hz).

Reference Production Example 10

A mixture of 3.63 g of 1-(2-methyl-3-triisopropylsilylthiophenyl)-4-methyl-1,4-dihydrotetrazol-5-one mentioned in Reference Production Example 9, 2.91 g of cesium fluoride, and 10 mL of N,N-dimethylformamide was stirred at room temperature for 30 minutes. To the mixture, 2.72 g of methyl iodide was added, followed by stirring at room temperature for 3 hours. To the reaction mixture, water was added and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.65 g of 1-(2-methyl-3-methylthiophenyl)-4-methyl-1,4-dihydrotetrazol-5-one.

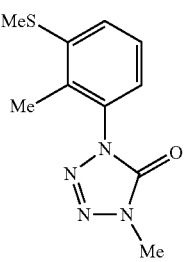 [SMILES: CSc1cccc(-n2nnn(C)c2=O)c1C]

$^1$H-NMR (CDCl$_3$) δ(ppm): 2.22 (3H, s), 2.51 (3H, s), 3.72 (3H, s), 7.10-7.16 (1H, m), 7.36-7.29 (2H, m).

Reference Production Example 11

A mixture of 1.50 g of 1-(2-methyl-3-methylthiophenyl)-4-methyl-1,4-dihydrotetrazol-5-one mentioned in Reference Production Example 10, 0.620 g of 1,1'-azobis(cyclohexane-1-carbonitrile), 1.30 g of N-bromosuccinimide, and 15 mL of chlorobenzene was stirred with heating under reflux for 4 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.400 g of 1-(2-bromomethyl-3-methylthiophenyl)-4-methyl-1,4-dihydrotetrazol-5-one.

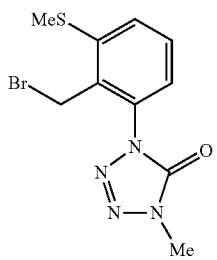 [SMILES: CSc1cccc(-n2nnn(C)c2=O)c1CBr]

$^1$H-NMR (CDCl$_3$) δ(ppm): 2.57 (3H, s), 3.75 (3H, s), 4.69 (2H, s), 7.20 (1H, t, J=4.5 Hz), 7.44 (2H, d, J=4.5 Hz).

Reference Production Example 12

Under ice cooling, 19.7 g of anhydrous aluminum chloride was added to 220 mL of N,N-dimethylformamide, followed by stirring for 15 minutes. To this was added 9.6 g of sodium azide and, after stirring for 15 minutes, 30.3 g of 1-bromo-3-isocyanato-2-methylbenzene mentioned in Reference Production Example 3 was added, followed by stirring at 80° C. for 5 hours. After cooling, the reaction solution was added in a mixture of 33 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 31.4 g of 1-(2-methyl-3-bromophenyl)-1,4-dihydrotetrazol-5-one.

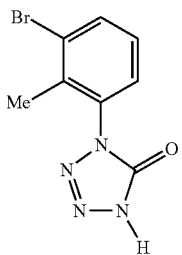 [SMILES: Cc1c(Br)cccc1-n1nn[nH]c1=O]

$^1$H-NMR (DMSO-d$_6$) δ(ppm): 2.22 (3H, s), 7.34 (1H, t, J=7.2 Hz), 7.49 (1H, dd, J=8.2, 1.1 Hz), 7.82 (1H, dd, J=8.0, 1.0 Hz), 14.72 (1H, s).

Reference Production Example 13

To a mixture of 31.40 g of 1-(2-methyl-3-bromophenyl)-1,4-dihydrotetrazol-5-one mentioned in Reference Production Example 12 and 250 mL of N,N-dimethylformamide, 5.90 g of 60% sodium hydride was added under ice cooling. The temperature of the mixture was raised to room temperature, followed by stirring for 1 hour. To the reaction mixture, 8.4 mL of methyl iodide was added under ice cooling. The temperature of the mixture was raised to room temperature, followed by stirring for 14 hours. To the reaction mixture, water was added and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 8.47 g of 1-(2-methyl-3-bromophenyl)-4-methyl-1,4-dihydrotetrazol-5-one).

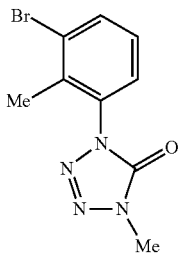 [SMILES: Cc1c(Br)cccc1-n1nnn(C)c1=O]

$^1$H-NMR (CDCl$_3$) δ(ppm): 2.33 (3H, s), 3.73 (3H, s), 7.21 (1H, dt, J=0.5, 7.8 Hz), 7.30 (1H, dd, J=1.0, 8.0 Hz), 7.71 (1H, dd, J=1.2, 8.3 Hz).

Reference Production Example 14

A mixture of 8.47 g of 1-(2-methyl-3-bromophenyl)-4-methyl-1,4-dihydrotetrazol-5-one mentioned in Reference Production Example 13, 1.54 g of 1,1'-azobis(cyclohexane-1-carbonitrile), 6.44 g of N-bromosuccinimide, and 125 mL of chlorobenzene was stirred with heating under reflux for 5 hours. After cooling, water was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 7.52 g of 1-(2-bromomethyl-3-bromophenyl)-4-methyl-1,4-dihydrotetrazol-5-one.

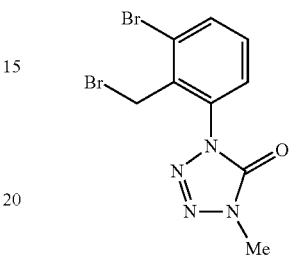

$^1$H-NMR (CDCl$_3$) δ(ppm): 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Production Example 15

A mixture of 45.0 g of 1-(2-bromomethyl-3-bromophenyl)-4-methyl-1,4-dihydrotetrazol-5-one mentioned in Reference Production Example 14, 37.4 g of sodium methoxide, and 600 mL of tetrahydrofuran was stirred at room temperature for 3 hours. To the reaction mixture, a saturated sodium bicarbonate solution was added and the mixture was extracted with ethyl acetate. The organic layer was washed with a saturated sodium bicarbonate solution, dried over anhydrous sodium sulfate, and then concentrated under reduced pressure to obtain 36.2 g of 1-(2-methoxymethyl-3-bromophenyl)-4-methyl-1,4-dihydrotetrazol-5-one.

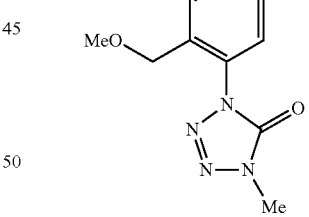

$^1$H-NMR (CDCl$_3$) δ(ppm): 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

Reference Production Example 16

A mixture of 36.2 g of 1-(2-methoxymethyl-3-bromophenyl)-4-methyl-1,4-dihydrotetrazol-5-one mentioned in Reference Production Example 15, 23.2 g of methylboronic acid, 66.7 g of cesium fluoride, 10.6 g of [1,1'-bis(diphenylphosphino)ferrocene]palladium(II) dichloride dichloromethane adduct, and 500 ml of dioxane was stirred at 90° C. for 5.5 hours. After cooling, the reaction mixture was filtered and the filtrate was concentrated under reduced pressure. The residue thus obtained was subjected to silica gel column chromatography to obtain 25.6 g of 1-(2-methoxymethyl-3-methylphenyl)-4-methyl-1,4-dihydrotetrazol-5-one.

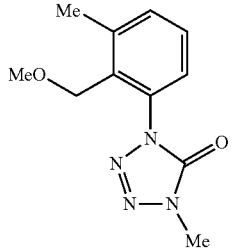 [SMILES: COCc1c(C)cccc1-n1nnn(C)c1=O]

¹H-NMR (CDCl₃) δ(ppm): 2.48 (3H, s), 3.23 (3H, s), 3.72 (3H, s), 4.42 (2H, s), 7.21 (1H, t, J=5.1 Hz), 7.35 (2H, d, J=4.8 Hz).

Reference Production Example 17

A mixture of 25.6 g of 1-(2-methoxymethyl-3-methylphenyl)-4-methyl-1,4-dihydrotetrazol-5-one mentioned in Reference Production Example 16, 50 mL of acetic acid, and 50 mL of a 25% hydrogen bromide-acetic acid solution was stirred at 65° C. for 1 hour. To the reaction mixture, a saturated saline solution was added and the mixture was extracted with ethyl acetate. The organic layer was washed with a saturated sodium bicarbonate solution, dried over anhydrous sodium sulfate, and then concentrated under reduced pressure to obtain 27.9 g of 1-(2-bromomethyl-3-methylphenyl)-4-methyl-1,4-dihydrotetrazol-5-one.

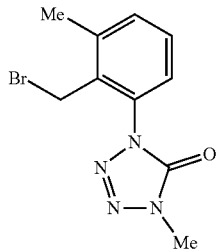 [SMILES: Cc1cccc(-n2nnn(C)c2=O)c1CBr]

¹H-NMR (CDCl₃) δ(ppm): 2.51 (3H, s), 3.75 (3H, s), 4.51 (2H, s), 7.22-7.24 (1H, m), 7.36-7.39 (2H, m).

Reference Production Example 18

A mixture of 30.1 g of 1-(2-methoxymethyl-3-bromophenyl)-4-methyl-1,4-dihydrotetrazol-5-one mentioned in Reference Production Example 15, 12.9 g of cyclopropylboronic acid, 46.2 g of cesium fluoride, 8.2 g of [1,1'-bis(diphenylphosphino)ferrocene]palladium(II) dichloride dichloromethane adduct, and 680 ml of dioxane was stirred at 90° C. for 4 hours. After cooling, the reaction mixture was filtered and the filtrate was concentrated under reduced pressure. The residue thus obtained was subjected to silica gel column chromatography to obtain 26.0 g of 1-(2-methoxymethyl-3-cyclopropylphenyl)-4-methyl-1,4-dihydrotetrazol-5-one.

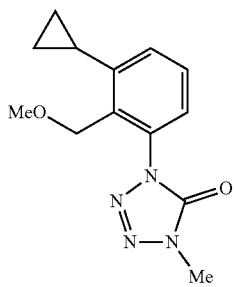 [SMILES: COCc1c(C2CC2)cccc1-n1nnn(C)c1=O]

¹H-NMR (CDCl₃) δ(ppm): 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).

Reference Production Example 19

A mixture of 26.0 g of 1-(2-methoxymethyl-3-cyclopropylphenyl)-4-methyl-1,4-dihydrotetrazol-5-one mentioned in Reference Production Example 18, 40 mL of acetic acid, and 40 mL of a 25% hydrogen bromide-acetic acid solution was stirred 65° C. for 2 hours. To the reaction mixture, a saturated saline solution was added and the mixture was extracted with ethyl acetate. The organic layer was washed with a saturated sodium bicarbonate solution, dried over anhydrous sodium sulfate, and then concentrated under reduced pressure to obtain 30.8 g of 1-(2-bromomethyl-3-cyclopropylphenyl)-4-methyl-1,4-dihydrotetrazol-5-one.

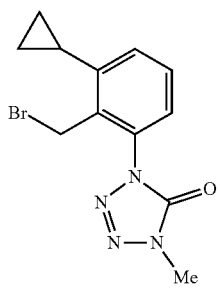 [SMILES: Cn1nnn(-c2cccc(C3CC3)c2CBr)c1=O]

¹H-NMR (CDCl₃) δ(ppm): 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Production Example 20

A mixture of 29.8 g of 1-(2-methoxymethyl-3-bromophenyl)-4-methyl-1,4-dihydrotetrazol-5-one mentioned in Reference Production Example 15, 35.2 g of tributylvinyltin, 11.6 g of tetrakistriphenylphosphinepalladium, and 500 mL of toluene was stirred with heating under reflux for 14 hours. After cooling, an aqueous saturated ammonium chloride solution was added to the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 19.7 g of 1-(2-methoxymethyl-3-ethenylphenyl)-4-methyl-1,4-dihydrotetrazol-5-one.

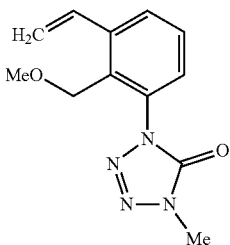

¹H-NMR (CDCl₃) δ(ppm): 7.67 (1H, dd, J=7.8, 1.3 Hz), 7.44 (1H, t, J=7.8 Hz), 7.29 (1H, dd, J=7.8, 1.3 Hz), 7.11 (1H, dd, J=17.4, 11.1 Hz), 5.72 (1H, dd, J=17.4, 1.3 Hz), 5.44 (1H, dd, J=11.1, 1.3 Hz), 4.45 (2H, s), 3.72 (3H, s), 3.23 (3H, s).

Reference Production Example 21

A mixture of 19.7 g of 1-(2-methoxymethyl-3-ethenyl-phenyl)-4-methyl-1,4-dihydrotetrazol-5-one mentioned in Reference Production Example 20, 3.02 g of a palladium-fibroin complex, and 1 L of methanol was stirred in a hydrogen atmosphere at room temperature for 11 hours. The reaction mixture was filtered and the filtrate was concentrated under reduced pressure. The residue thus obtained was subjected to silica gel column chromatography to obtain 19.3 g of 1-(2-methoxymethyl-3-ethylphenyl)-4-methyl-1,4-dihydrotetrazol-5-one.

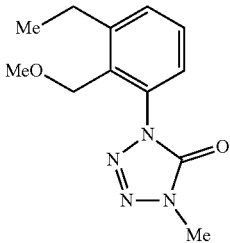

¹H-NMR (CDCl₃) δ(ppm): 7.42-7.38 (2H, m), 7.23-7.20 (1H, m), 4.44 (2H, s), 3.72 (3H, s), 3.22 (3H, s), 2.82 (2H, q, J=7.6 Hz), 1.27 (3H, t, J=7.6 Hz).

Reference Production Example 22

A mixture of 19.3 g of 1-(2-methoxymethyl-3-ethylphenyl)-4-methyl-1,4-dihydrotetrazol-5-one mentioned in Reference Production Example 21, 40 mL of acetic acid, and 40 mL of a 25% hydrogen bromide-acetic acid solution was stirred at 65° C. for 1.5 hours. To the reaction mixture, a saturated saline solution was added and the mixture was extracted with ethyl acetate. The organic layer was washed with a saturated sodium bicarbonate solution, dried over anhydrous sodium sulfate, and then concentrated under reduced pressure to obtain 23.3 g of 1-(2-bromomethyl-3-ethylphenyl)-4-methyl-1,4-dihydrotetrazol-5-one.

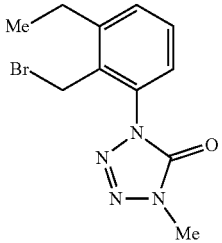

¹H-NMR (CDCl₃) δ(ppm): 7.44-7.37 (2H, m), 7.23 (1H, dd, J=7.1, 2.0 Hz), 4.56 (2H, s), 3.75 (3H, s), 2.85 (2H, q, J=7.6 Hz), 1.33 (3H, t, J=7.6 Hz).

Reference Production Example 23

A mixture of 9.5 g of diethyl carbonate, 2.8 g of 55% sodium hydride, and 200 ml of toluene was stirred at 80° C. for 0.5 hour. To the reaction mixture, 5 g of 2-chloroacetophenone was added, followed by stirring for 2 hours. At room temperature, 100 ml of water was added and the mixture was extracted with ethyl acetate. The organic layer was washed with a saturated saline solution to obtain a crude product of 3-(2-chlorophenyl)-3-oxopropionic acid ethyl ester. At room temperature, 100 ml of ethanol and 2.2 g of methylhydrazine were added to the crude product of the 3-(2-chlorophenyl)-3-oxopropionic acid ethyl ester, followed by stirring with heating under reflux for 4 hours. The reaction mixture was concentrated under reduced pressure and acidified by adding 10% hydrochloric acid. The precipitate thus produced was collected by filtration, washed with water, ethyl acetate, and hexane, and then concentrated under reduced pressure to obtain 4.2 g of 3-(2-chlorophenyl)-1-methyl-1H-pyrazol-5-ol.

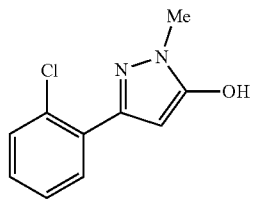 [SMILES: Cn1nc(-c2ccccc2Cl)cc1O]

¹H-NMR (DMSO-D₆) δ: 7.75 (1H, dd, J=7.3, 2.2 Hz), 7.50 (1H, dd, J=7.1, 2.0 Hz), 7.39-7.32 (2H, m), 5.95 (1H, s), 3.62 (3H, s).

The following intermediates were obtained by the same production process.

3-(3-Chlorophenyl)-1-methyl-1H-pyrazol-5-ol

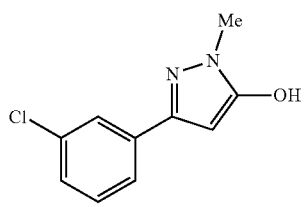 [SMILES: Cn1nc(-c2cccc(Cl)c2)cc1O]

¹H-NMR (DMSO-D₆) δ: 7.72-7.72 (1H, m), 7.66 (1H, dd, J=7.7, 1.0 Hz), 7.38 (1H, t, J=7.7 Hz), 7.30 (1H, d, J=7.7 Hz), 5.87 (1H, s), 3.57 (3H, s).

3-(3-Chlorophenyl)-1-ethyl-1H-pyrazol-5-ol

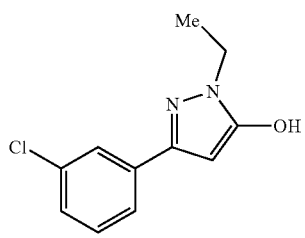 [SMILES: CCn1nc(-c2cccc(Cl)c2)cc1O]

¹H-NMR (DMSO-D₆) δ: 11.11 (1H, s), 7.73-7.72 (1H, m), 7.67-7.65 (1H, m), 7.38 (1H, t, J=7.9 Hz), 7.31-7.28 (1H, m), 5.85 (1H, s), 3.93 (2H, q, J=7.2 Hz), 1.29 (3H, t, J=7.2 Hz).

Reference Production Example 24

To a mixture of 40 g of an aqueous 40% methylamine solution and 240 mL of methanol, 10 g of 2-bromo-1-(4-chlorophenyl)ethanone was added under ice cooling, followed by stirring for 30 minutes. After concentrating the reaction solution, 30 mL of methanol and 6.95 g of potassium cyanate were added, followed by stirring with heating under reflux for 1 hour. To the reaction solution, 10 mL of acetic acid was added, followed by stirring with heating under reflux for 1 hour. The reaction mixture was concentrated under reduced pressure and alkalified with a saturated sodium bicarbonate solution, and then the mixture was extracted with chloroform. The solvent was distilled off under reduced pressure to obtain 1.4 g of 1-methyl-4-(4-chlorophenyl)-1,3-dihydroimidazol-2-one.

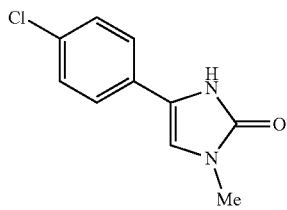 [SMILES: Cn1cc(-c2ccc(Cl)cc2)[nH]c1=O]

$^1$H-NMR (DMSO-D$_6$) δ: 10.71 (1H, s), 7.48 (2H, d, J=8.5 Hz), 7.38 (2H, d, J=8.5 Hz), 7.05 (1H, s), 3.13 (3H, s).

Reference Production Example 25

To a mixture of 0.50 g of 1-(2-(hydroxymethyl)-3-methylphenyl)-4-methyl-1,4-dihydrotetrazol-5-one and 10 mL of dimethoxyethane, 0.10 g of sodium hydride (55%, dispersed in liquid paraffin) was added under stirring. After stirring at room temperature for 10 minutes, 0.46 g of 3-bromo-5-chloro-1,2,4-thiadiazole was added, followed by stirring at room temperature for 2 hours. To the reaction mixture, a saturated sodium bicarbonate solution was added and the mixture was extracted with ethyl acetate. The organic layer was washed with water and a saturated sodium bicarbonate solution, dried over anhydrous sodium sulfate, and then concentrated under reduced pressure to obtain 0.85 g of 1-[2-(3-bromo-1,2,4-thiadiazol-5-yloxymethyl)-3-methylphenyl]-4-methyl-1,4-dihydrotetrazol-5-one.

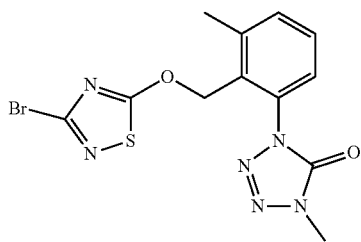 [SMILES: Cc1cccc(-n2nnn(C)c2=O)c1COc1nc(Br)ns1]

$^1$H-NMR (CDCl$_3$) δ: 2.55 (3H, s), 3.75 (3H, s), 5.61 (2H, s), 7.31 (1H, d, J=7.9 Hz), 7.42 (1H, d, J=6.8 Hz), 7.48 (1H, t, J=7.7 Hz).

Reference Production Example 26

A mixture of 1.0 g of 2-bromo-1-(2-methoxyphenyl)ethanone, 1.2 g of sodium formate, and 15 mL of methanol was stirred with heating under reflux for 3 hours. To the reaction mixture allowed to cool, water was added and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 0.5 g of 1-(2-methoxyphenyl)-2-hydroxyethanone.

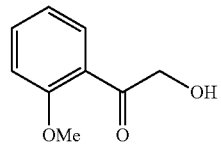 [SMILES: COc1ccccc1C(=O)CO]

$^1$H-NMR (CDCl$_3$) δ: 8.06-8.04 (1H, m), 7.58-7.53 (1H, m), 7.08-7.04 (1H, m), 7.01 (1H, d, J=8.5 Hz), 4.77 (2H, d, J=4.8 Hz), 3.94 (3H, s), 3.77 (1H, t, J=4.8 Hz).

Reference Production Example 27

A mixture of 0.5 g of 1-(2-methoxyphenyl)-2-hydroxyethanone, 0.5 g of potassium cyanate, 1 mL of acetic acid, and 10 mL of isopropanol was stirred with heating under reflux for 3 hours. To the reaction mixture allowed to cool, water was added and the mixture was extracted with ethyl acetate. The organic layer was washed with a saturated saline solution, dried over anhydrous magnesium sulfate, and then concentrated under reduced pressure. The residue thus obtained was washed with hexane to obtain 0.15 g of 4-(2-methoxyphenyl)-4-oxazolin-2-one.

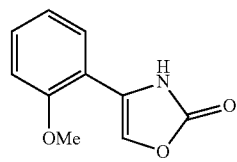 [SMILES: COc1ccccc1-c1coc(=O)[nH]1]

$^1$H-NMR (CDCl$_3$) δ: 9.96 (1H, br s), 7.42-7.40 (1H, m), 7.35-7.31 (1H, m), 7.28 (1H, s), 7.07-7.03 (1H, m), 6.98 (1H, d, J=8.4 Hz), 3.95 (3H, s).

Reference Production Example 28

The same reaction was carried out, except that 2-bromo-1-(2-methoxyphenyl)ethanone of Reference Production Example 26 was replaced by 2-bromo-1-(4-chlorophenyl)ethanone, 1-(4-chlorophenyl)-2-hydroxyethanone was obtained.

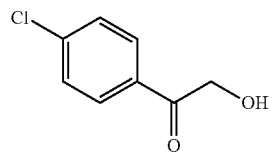 [SMILES: O=C(CO)c1ccc(Cl)cc1]

$^1$H-NMR (CDCl$_3$) δ: 7.90 (2H, d, J=8.4 Hz), 7.50 (2H, d, J=8.4 Hz), 4.80 (2H, s), 3.20 (1H, bs).

Reference Production Example 29

The same reaction was carried out, except that 1-(2-methoxyphenyl)-2-hydroxyethanone of Reference Production Example 27 was replaced by 1-(4-chlorophenyl)-2-hydroxyethanone, 4-(4-chlorophenyl)-4-oxazolin-2-one was obtained.

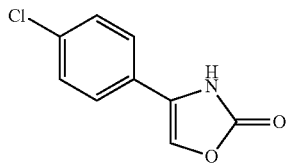 [SMILES: O=c1[nH]c(-c2ccc(Cl)cc2)co1]

¹H-NMR (DMSO-D₆) δ: 11.43 (1H, s), 7.76 (1H, s), 7.59 (2H, d, J=8.9 Hz), 7.52 (2H, d, J=8.9 Hz).

Reference Production Example 30

The same reaction was carried out, except that 2-bromo-1-(2-methoxyphenyl)ethanone of Reference Production Example 26 was replaced by 2-bromo-1-(4-methoxyphenyl)ethanone, 1-(4-methoxyphenyl)-2-hydroxyethanone was obtained.

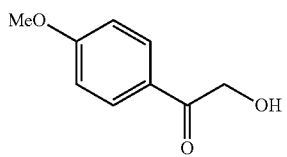 [SMILES: COc1ccc(C(=O)CO)cc1]

¹H-NMR (CDCl₃) δ: 7.91 (2H, d, J=8.8 Hz), 6.98 (2H, d, J=8.8 Hz), 4.83 (2H, d, J=4.5 Hz), 3.89 (3H, s), 3.58 (1H, t, J=4.5 Hz).

Reference Production Example 31

The same reaction was carried out, except that 1-(2-methoxyphenyl)-2-hydroxyethanone of Reference Production Example 27 was replaced by 1-(4-methoxyphenyl)-2-hydroxyethanone, 4-(4-methoxyphenyl)-4-oxazolin-2-one was obtained.

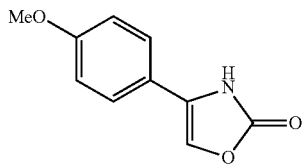 [SMILES: COc1ccc(-c2coc(=O)[nH]2)cc1]

¹H-NMR (CDCl₃) δ: 7.91 (2H, d, J=8.8 Hz), 6.98 (2H, d, J=8.8 Hz), 4.83 (2H, d, J=4.5 Hz), 3.89 (3H, s), 3.58 (1H, t, J=4.5 Hz).

Reference Production Example 32

The same reaction was carried out, except that 2-bromo-1-(2-methoxyphenyl)ethanone of Reference Production Example 26 was replaced by 2-bromo-1-(3-chlorophenyl)ethanone, 1-(3-chlorophenyl)-2-hydroxyethanone was obtained.

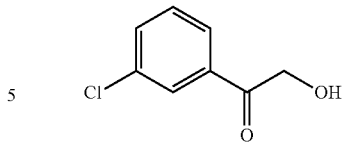

¹H-NMR (CDCl₃) δ: 7.92-7.90 (1H, m), 7.81-7.79 (1H, m), 7.62-7.60 (1H, m), 7.48-7.44 (1H, m), 4.87 (2H, s), 3.42 (1H, s).

Reference Production Example 33

The same reaction was carried out, except that 1-(2-methoxyphenyl)-2-hydroxyethanone of Reference Production Example 27 was replaced by 1-(3-chlorophenyl)-2-hydroxyethanone, 4-(3-chlorophenyl)-4-oxazolin-2-one was obtained.

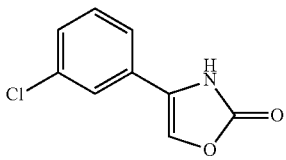

¹H-NMR (CDCl₃) δ: 10.61 (1H, br s), 7.41-7.30 (4H, m), 7.14 (1H, s).

Reference Production Example 34

The same reaction was carried out, except that 1-(2-methoxyphenyl)-2-hydroxyethanone of Reference Production Example 27 was replaced by 1-phenyl-2-hydroxyethanone, 4-phenyl-4-oxazolin-2-one was obtained.

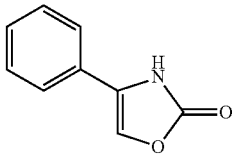 [SMILES: O=c1[nH]c(-c2ccccc2)co1]

¹H-NMR (CDCl₃) δ: 10.96 (1H, br s), 7.46-7.43 (4H, m), 7.38-7.35 (1H, m), 7.14 (1H, s).

Reference Production Example 35

The same reaction was carried out, except that 2-bromo-1-(2-methoxyphenyl)ethanone of Reference Production Example 26 was replaced by 2-bromo-1-(4-cyanophenyl)ethanone, 1-(4-cyanophenyl)-2-hydroxyethanone was obtained.

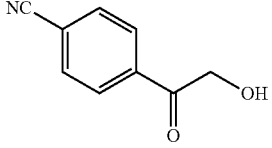 [SMILES: N#Cc1ccc(C(=O)CO)cc1]

¹H-NMR (CDCl₃) δ: 8.03 (2H, d, J=8.8 Hz), 7.83 (2H, d, J=8.8 Hz), 4.91 (2H, s), 3.40 (1H, br s).

Reference Production Example 35

The same reaction was carried out, except that 1-(2-methoxyphenyl)-2-hydroxyethanone of Reference Production Example 27 was replaced by 1-(4-cyanophenyl)-2-hydroxyethanone, 4-(4-cyanophenyl)-4-oxazolin-2-one was obtained.

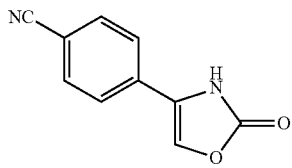 [SMILES: N#Cc1ccc(-c2coc(=O)[nH]2)cc1]

$^1$H-NMR (DMSO-D$_6$) δ: 7.93 (1H, s), 7.92 (2H, d, J=8.6 Hz), 7.74 (2H, d, J=8.6 Hz).

Reference Production Example 36

A mixture of 2.0 g of 1-phenyl-2-hydroxyethanone, 2.1 g of potassium thiocyanate, and 30 mL of hydrochloric acid (1N) was stirred at 90° C. for 5 hours. The reaction mixture allowed to cool was extracted with ethyl acetate. The organic layer was washed with a saturated saline solution, dried over anhydrous magnesium sulfate, and then concentrated under reduced pressure. The residue thus obtained was washed with hexane to obtain 0.4 g of 4-phenyl-4-oxazoline-2-thione.

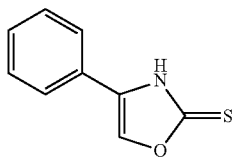 [SMILES: S=c1[nH]c(-c2ccccc2)co1]

$^1$H-NMR (CDCl$_3$) δ: 7.56 (1H, s), 7.50-7.42 (5H, m).

Reference Production Example 37

The same reaction was carried out, except that 1-phenyl-2-hydroxyethanone of Reference Production Example 36 was replaced by 1-(4-chlorophenyl)-2-hydroxyethanone, 4-(4-chlorophenyl)-4-oxazoline-2-thione was obtained.

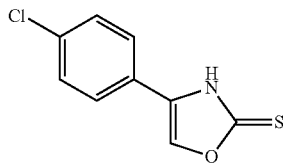 [SMILES: S=c1[nH]c(-c2ccc(Cl)cc2)co1]

$^1$H-NMR (CDCl$_3$) δ: 7.51 (1H, s), 7.45 (2H, d, J=8.9 Hz), 7.37 (2H, d, J=8.9 Hz).

Reference Production Example 38

The same reaction was carried out, except that 1-phenyl-2-hydroxyethanone of Reference Production Example 36 was replaced by 1-(3-chlorophenyl)-2-hydroxyethanone, 4-(3-chlorophenyl)-4-oxazoline-2-thione was obtained.

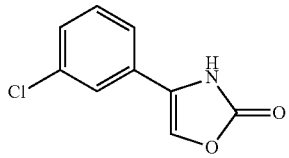 [SMILES: O=c1[nH]c(-c2cccc(Cl)c2)co1]

$^1$H-NMR (DMSO-D$_6$) δ: 8.39 (1H, s), 7.83-7.82 (1H, m), 7.66-7.64 (1H, m), 7.53-7.45 (2H, m).

Reference Production Example 39

A mixture of 1.0 g of 4-chlorothiobenzohydrazide (synthesized in accordance with the process mentioned in Journal of Medicinal Chemistry, 50(17), 4255-4259; 2007), 0.9 g of 1,1'-carbonyldiimidazole, and 10 mL of tetrahydrofuran was stirred at room temperature for 5 hours. The reaction mixture was acidified by adding hydrochloric acid (1N) and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 0.19 g of 5-(4-chlorophenyl)-1,3,4-thiadiazol-2-one.

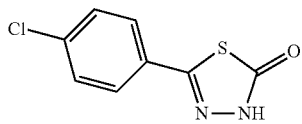 [SMILES: O=c1[nH]nc(-c2ccc(Cl)cc2)s1]

$^1$H-NMR (CDCl$_3$) δ: 8.84 (1H, s), 7.80 (2H, d, J=8.6 Hz), 7.47 (2H, d, J=8.6 Hz).

Reference Production Example 40

A mixture of 4.0 g of 1-(2-hydroxymethyl-3-methylphenyl)-4-methyl-1,4-dihydrotetrazol-5-one, 2.4 g of potassium tert-butoxide, and 50 mL of tetrahydrofuran was stirred at 25° C. for 15 minutes, and 4.4 g of 2,5-dibromo-thiazole was added, followed by stirring at 60° C. for 1 hour. To the reaction mixture allowed to cool, water was added and the mixture was extracted with ethyl acetate. The organic layer was washed with a saturated saline solution, dried over anhydrous magnesium sulfate, and then concentrated under reduced pressure. The residue thus obtained was subjected to silica gel column chromatography to obtain 3.0 g of 1-{2-[4-bromo-1,3-thiazol-2-yloxymethyl]-3-methylphenyl}-4-methyl-1,4-dihydrotetrazol-5-one.

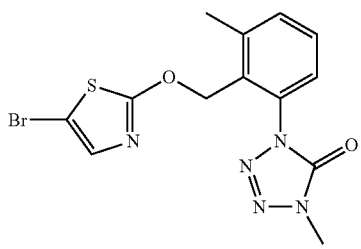 [SMILES: Cc1cccc(-n2nnn(C)c2=O)c1COc1ncc(Br)s1]

1H-NMR (CDCl3) δ: 7.44-7.39 (2H, m), 7.28-7.26 (1H, m), 6.97 (1H, s), 5.44 (2H, s), 3.71 (3H, s), 2.52 (3H, s).

In accordance with the process mentioned above, it is possible to obtain compounds HA1001-0001 to HA1518-1040.

The compounds HA1001-0001 to HA1518-1040 are tetrazolinone compounds represented by the following formulas:
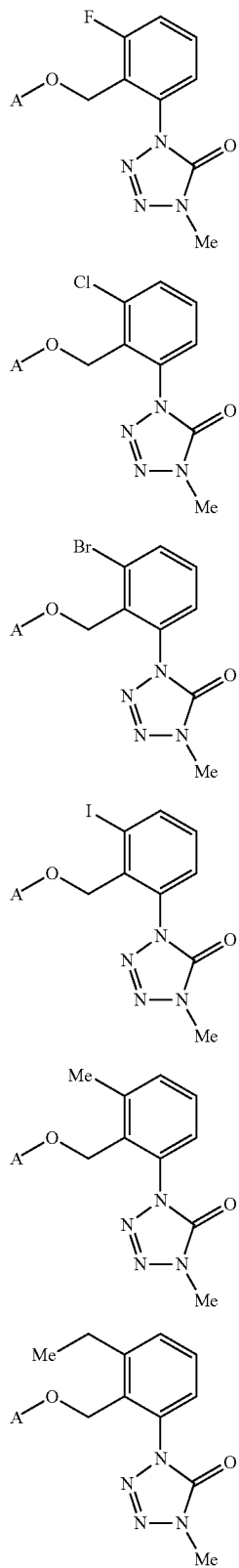
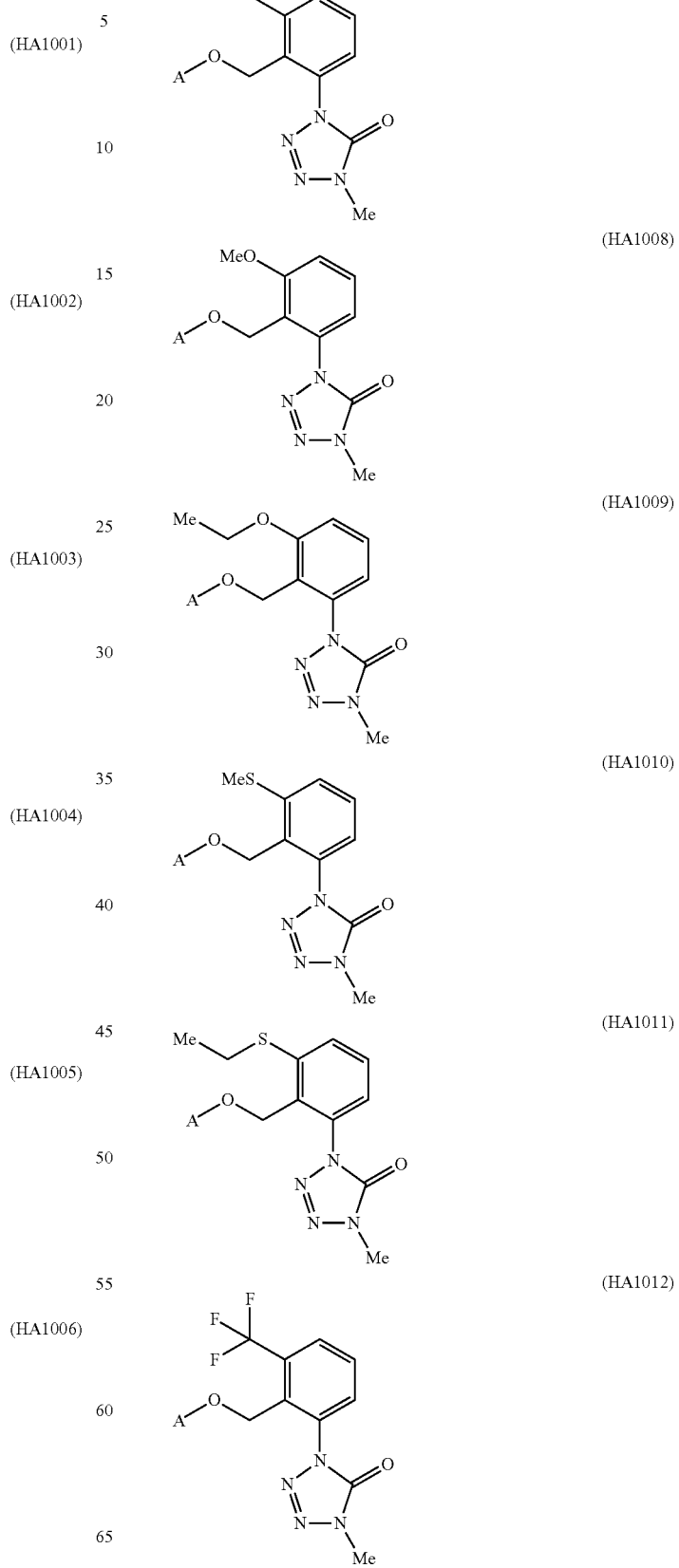

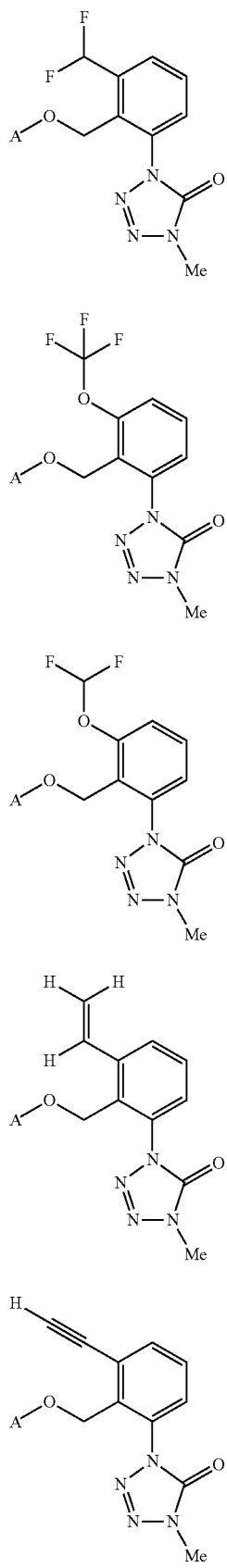
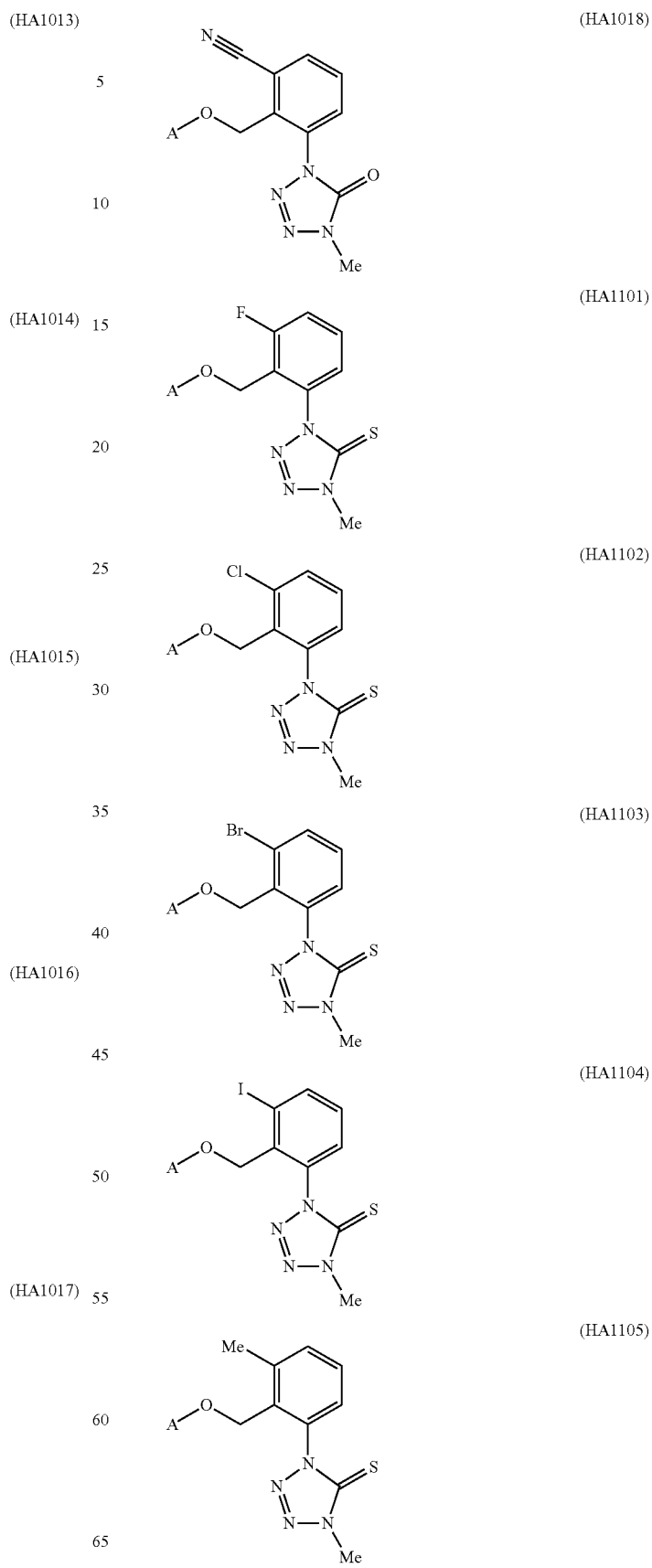

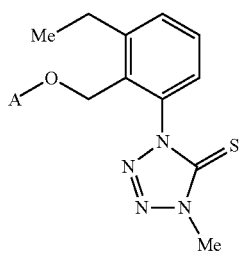 (HA1106)
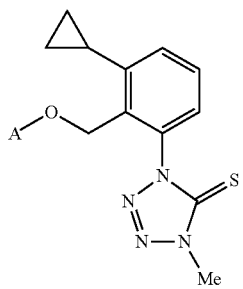 (HA1107)
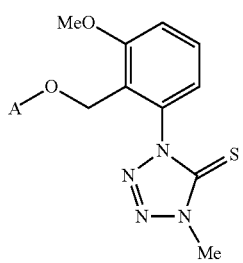 (HA1108)
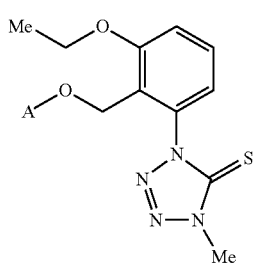 (HA1109)
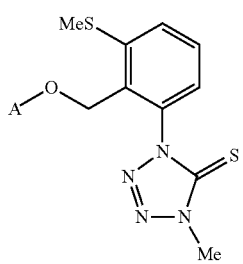 (HA1110)
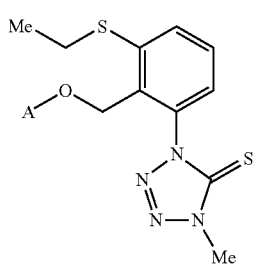 (HA1111)
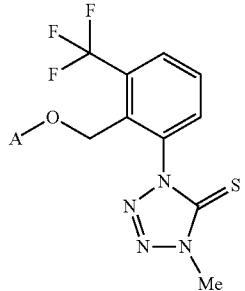 (HA1112)
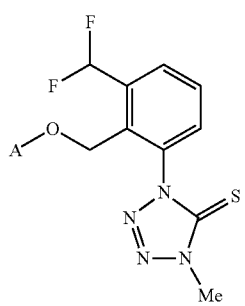 (HA1113)
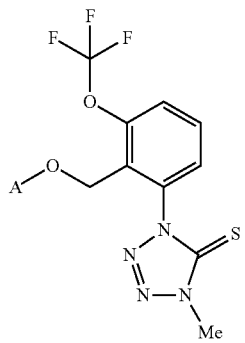 (HA1114)
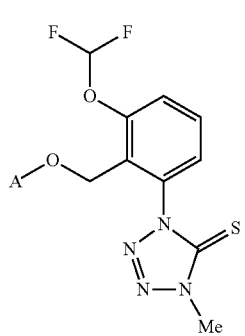 (HA1115)
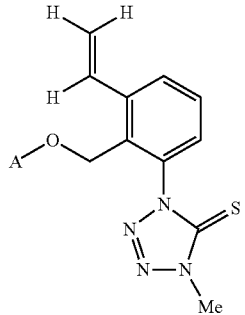 (HA1116)

103
-continued
(HA1117)
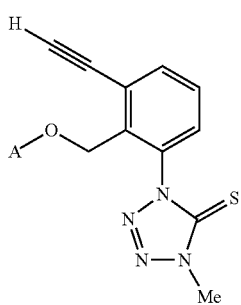
(HA1118)
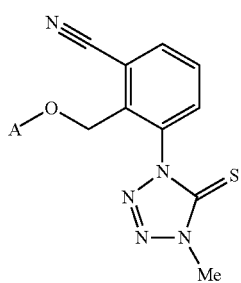
(HA1201)
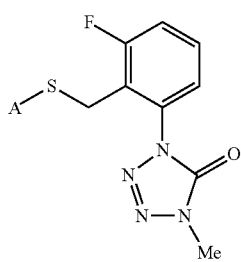
(HA1202)
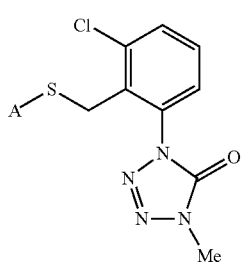
(HA1203)
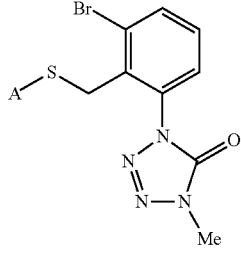
(HA1204)
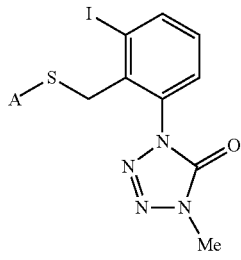
104
-continued
(HA1205)
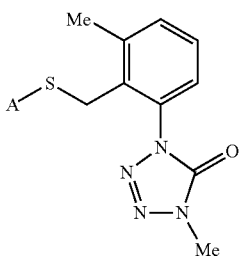
(HA1206)
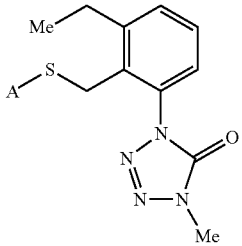
(HA1207)
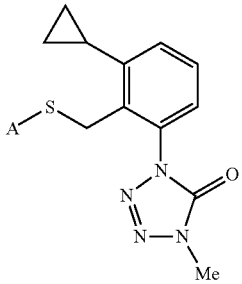
(HA1208)
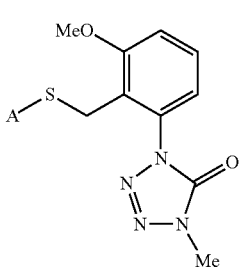
(HA1209)
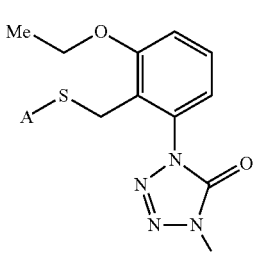
(HA1210)
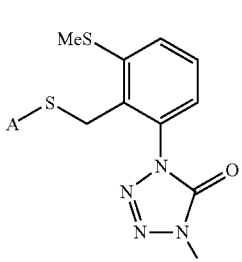

-continued
(HA1211) 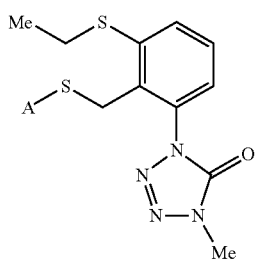
(HA1212) 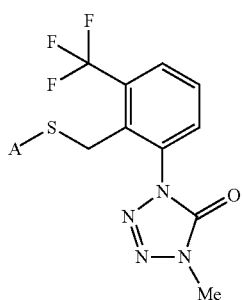
(HA1213) 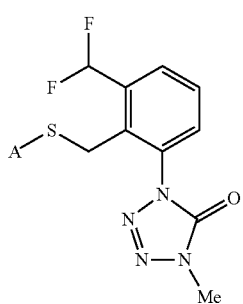
(HA1214) 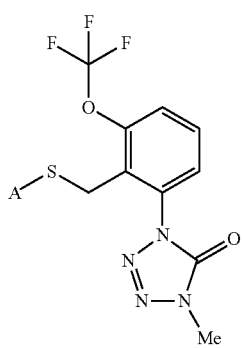
(HA1215) 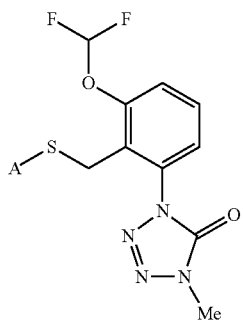
-continued
(HA1216) 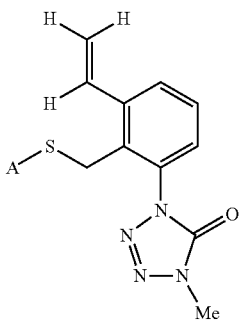
(HA1217) 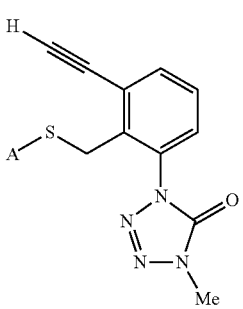
(HA1218) 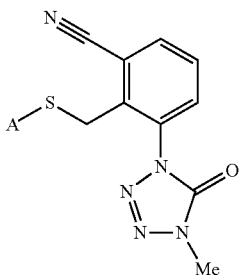
(HA1301) 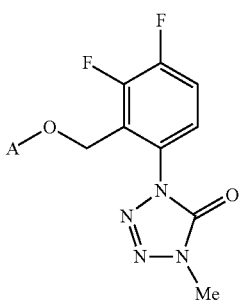
(HA1302) 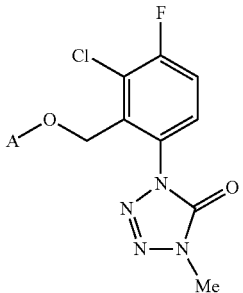

107
-continued
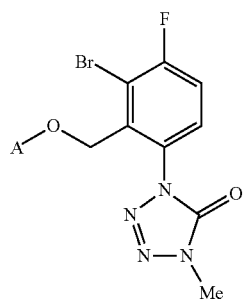
(HA1303)
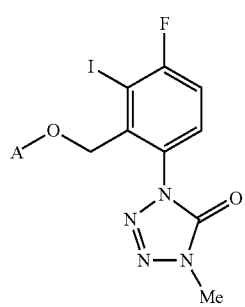
(HA1304)
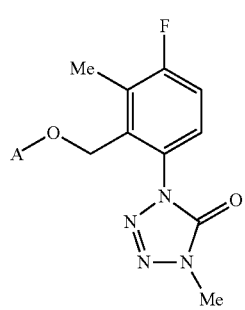
(HA1305)
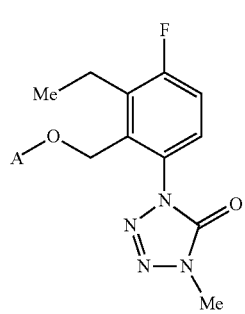
(HA1306)
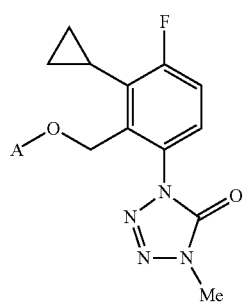
(HA1307)
108
-continued
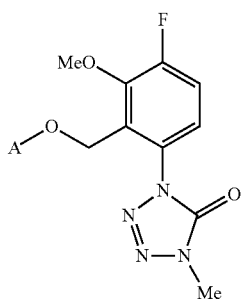
(HA1308)
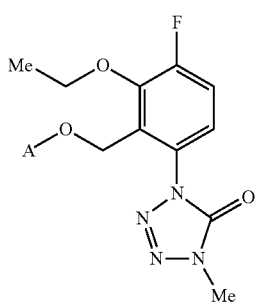
(HA1309)
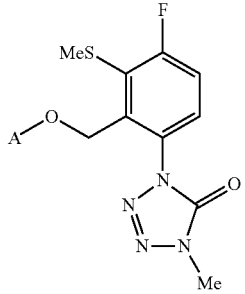
(HA1310)
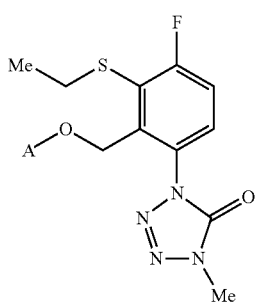
(HA1311)
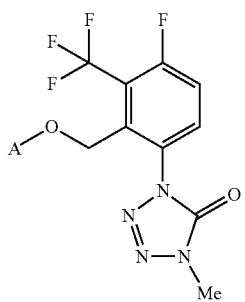
(HA1312)

109
-continued
(HA1313)
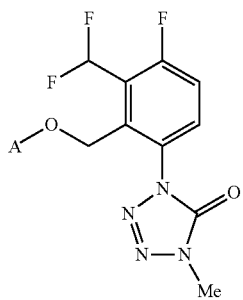
(HA1314)
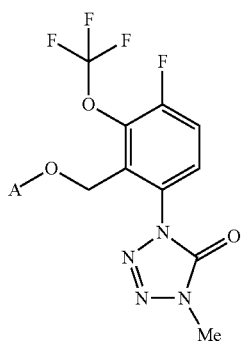
(HA1315)
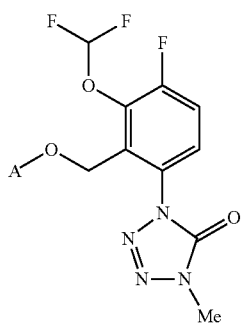
(HA1316)
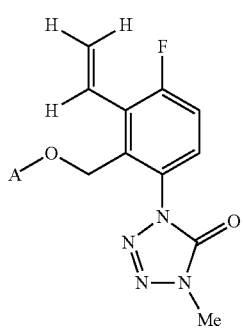
(HA1317)
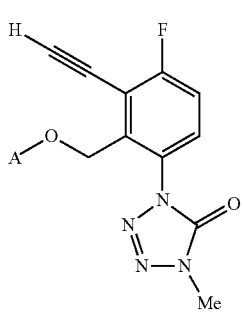
110
-continued
(HA1318)
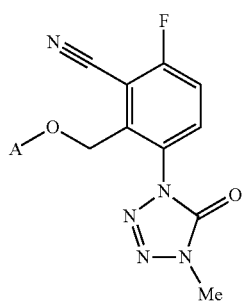
(HA1401)
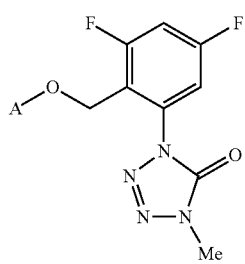
(HA1402)
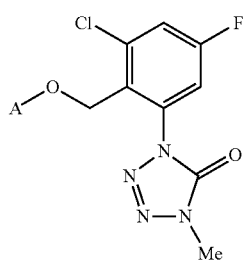
(HA1403)
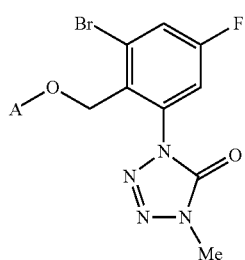
(HA1404)
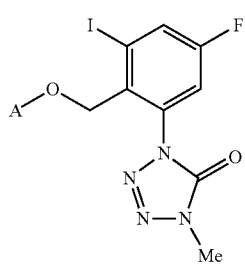
(HA1405)
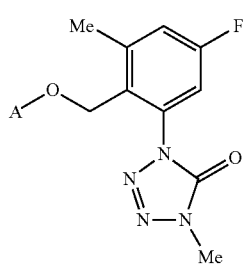

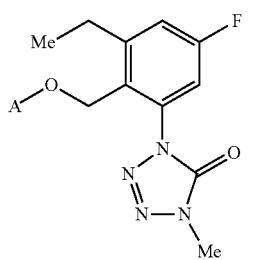
(HA1406)
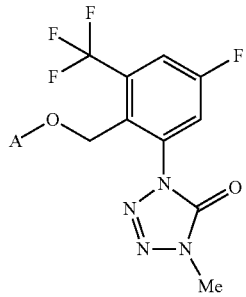
(HA1412)
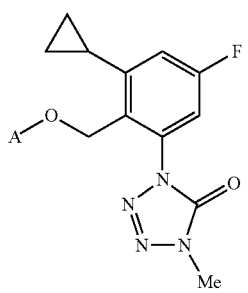
(HA1407)
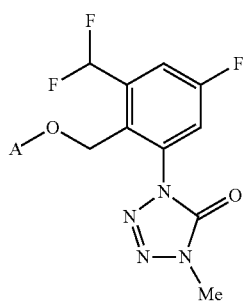
(HA1413)
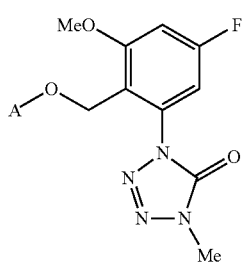
(HA1408)
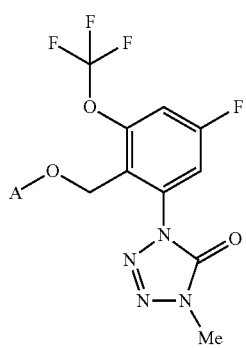
(HA1414)
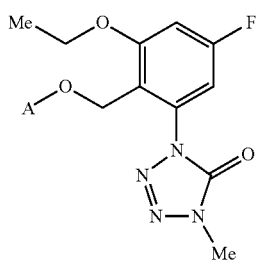
(HA1409)
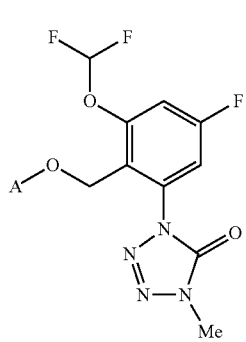
(HA1415)
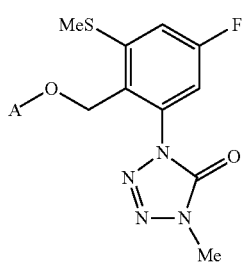
(HA1410)
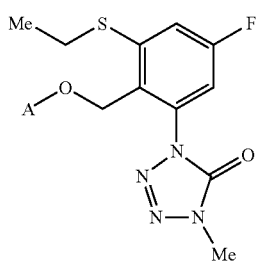
(HA1411)
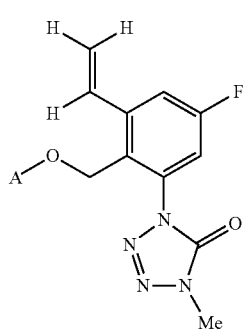
(HA1416)

-continued
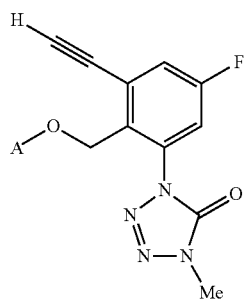 (HA1417)
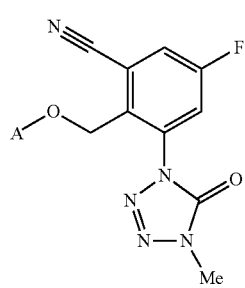 (HA1418)
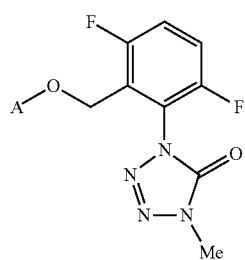 (HA1501)
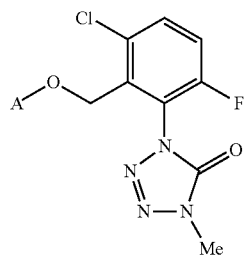 (HA1502)
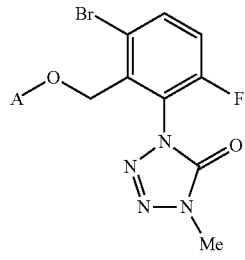 (HA1503)
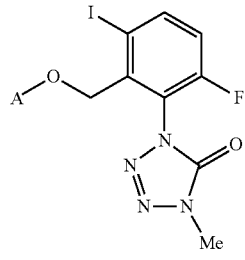 (HA1504)
-continued
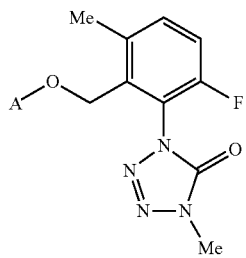 (HA1505)
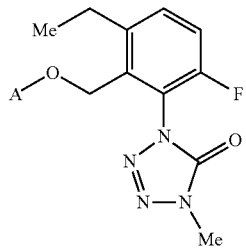 (HA1506)
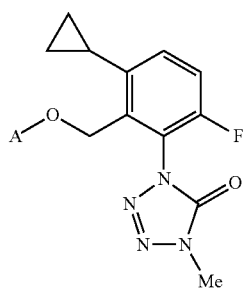 (HA1507)
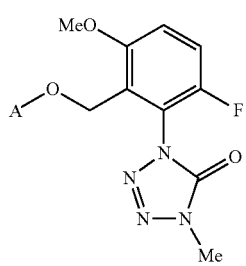 (HA1508)
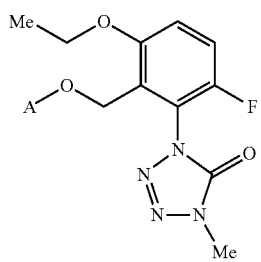 (HA1509)
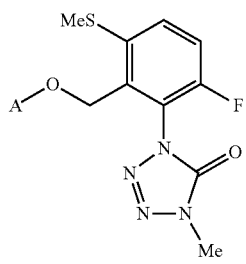 (HA1510)

-continued (HA1511) 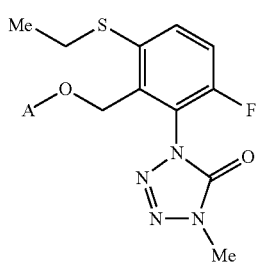

(HA1512) 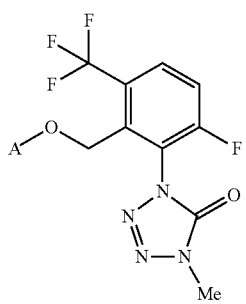

(HA1513) 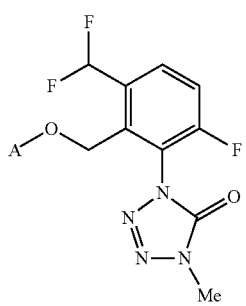

(HA1514) 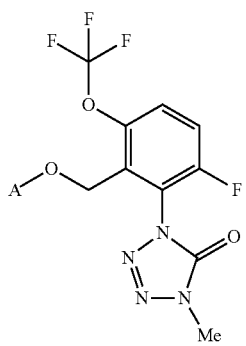

(HA1515) 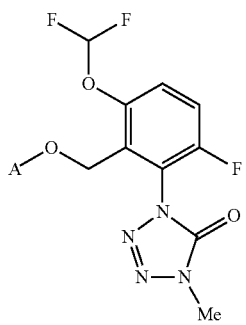

-continued (HA1516) 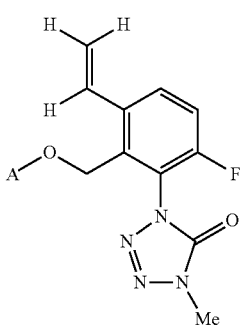

(HA1517) 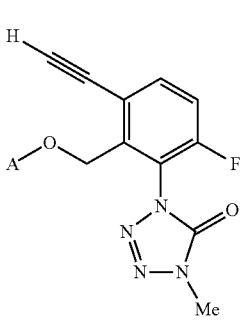

(HA1518) 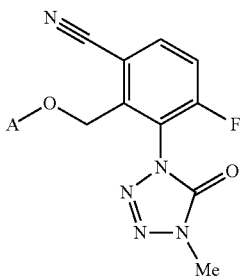

wherein A is a substituent corresponding to each of substituent numbers 1 to 1040. PYR mentioned in the following [substituent number; A] represents pyrazole, TRI represents triazole, TET represents tetrazole, THI represents thiophene, FUR represents furan, THA represents thiazole, OXA represents oxazole, IMI represents imidazole, PRL represents pyrrole, TDA represents thiadiazole, F represents fluoro, Cl represents chloro, Br represents bromo, CN represents cyano, Me represents methyl, Et represents ethyl, CF3 represents trifluoromethyl, OMe represents methoxy, and OEt represents ethoxy.

For example, HA1001-0001 represents a compound represented by formula (HA1001) in which Y is a substituent 0001, and is represented by the following formula.

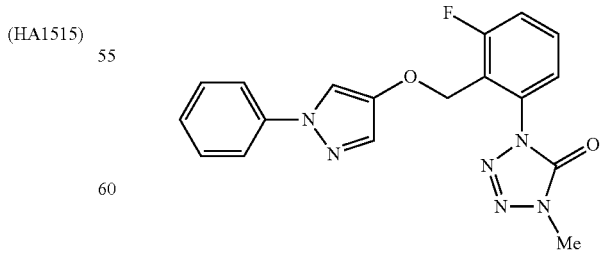

HA1001-0001

[0001;1-phenyl-PYR-4-yl], [0002;1-(2-F-Ph)PYR-4-yl], [0003;1-(3-F-Ph)PYR-4-yl], [0004;1-(4-F-Ph)PYR-4-yl], [0005;1-(2-Cl-Ph)PYR-4-yl], [0006;1-(3-Cl-Ph)PYR-4-yl],

[0007;1-(4-Cl-Ph)PYR-4-yl], [0008;1-(2-Br-Ph)PYR-4-yl], [0009;1-(3-Br-Ph)PYR-4-yl], [0010;1-(4-Br-Ph)PYR-4-yl], [0011;1-(2-Me-Ph)PYR-4-yl], [0012;1-(3-Me-Ph)PYR-4-yl], [0013;1-(4-Me-Ph)PYR-4-yl], [0014;1-(2-Et-Ph)PYR-4-yl], [000015;1-(3-Et-Ph)PYR-4-yl], [0016;1-(4-Et-Ph)PYR-4-yl], [0017;1-(2-CF3-Ph)PYR-4-yl], [0018;1-(3-CF3-Ph)PYR-4-yl], [0019;1-(4-CF3-Ph)PYR-4-yl], [0020;1-(2-OMe-Ph)PYR-4-yl], [0021;1-(3-OMe-Ph)PYR-4-yl], [0022;1-(4-OMe-Ph)PYR-4-yl], [0023;1-(2-OEt-Ph)PYR-4-yl], [0024;1-(3-OEt-Ph)PYR-4-yl], [0025;1-(4-OEt-Ph)PYR-4-yl], [0026;1-(4-F-2-F-Ph)PYR-4-yl], [0027;1-(4-Cl-2-F-Ph)PYR-4-yl], [0028;1-(4-Br-2-F-Ph)PYR-4-yl], [0029;1-(4-Me-2-F-Ph)PYR-4-yl], [0030;1-(4-Et-2-F-Ph)PYR-4-yl], [0031;1-(4-CF3-2-F-Ph)PYR-4-yl], [0032;1-(4-OMe-2-F-Ph)PYR-4-yl], [0033;1-(4-OEt-2-F-Ph)PYR-4-yl], [0034;1-(4-F-2-Cl-Ph)PYR-4-yl], [0035;1-(4-Cl-2-Cl-Ph)PYR-4-yl], [0036;1-(4-Br-2-Cl-Ph)PYR-4-yl], [0037;1-(4-Me-2-Cl-Ph)PYR-4-yl], [0038;1-(4-Et-2-Cl-Ph)PYR-4-yl], [0039;1-(4-CF3-2-Cl-Ph)PYR-4-yl], [0040;1-(4-OMe-2-Cl-Ph)PYR-4-yl], [0041;1-(4-OEt-2-Cl-Ph)PYR-4-yl], [0042;1-(4-F-2-Me-Ph)PYR-4-yl], [0043;1-(4-Cl-2-Me-Ph)PYR-4-yl], [0044;1-(4-Br-2-Me-Ph)PYR-4-yl], [0045;1-(4-Me-2-Me-Ph)PYR-4-yl], [0046;1-(4-Et-2-Me-Ph)PYR-4-yl], [0047;1-(4-CF3-2-Me-Ph)PYR-4-yl], [0048;1-(4-OMe-2-Me-Ph)PYR-4-yl], [0049;1-(4-OEt-2-Me-Ph)PYR-4-yl], [0050;1-(4-F-2-OMe-Ph)PYR-4-yl], [0051;1-(4-Cl-2-OMe-Ph)PYR-4-yl], [0052;1-(4-Br-2-OMe-Ph)PYR-4-yl], [0053;1-(4-Me-2-OMe-Ph)PYR-4-yl], [0054;1-(4-Et-2-OMe-Ph)PYR-4-yl], [0055;1-(4-CF3-2-OMe-Ph)PYR-4-yl], [0056;1-(4-OMe-2-OMe-Ph)PYR-4-yl], [0057;1-(4-OEt-2-OMe-Ph)PYR-4-yl], [0058;1-(4-F-2-OEt-Ph)PYR-4-yl], [0059;1-(4-Cl-2-OEt-Ph)PYR-4-yl], [0060;1-(4-Br-2-OEt-Ph)PYR-4-yl], [0061;1-(4-Me-2-OEt-Ph)PYR-4-yl], [0062;1-(4-Et-2-OEt-Ph)PYR-4-yl], [0063;1-(4-CF3-2-OEt-Ph)PYR-4-yl], [0064;1-(4-OMe-2-OEt-Ph)PYR-4-yl], [0065;1-(4-OEt-2-OEt-Ph)PYR-4-yl], [0066;3-Ph-1-Me-PYR-5-yl], [0067;3-(2-F-Ph)-1-Me-PYR-5-yl], [0068;3-(3-F-Ph)-1-Me-PYR-5-yl], [0069;3-(4-F-Ph)-1-Me-PYR-5-yl], [0070;3-(2-Cl-Ph)-1-Me-PYR-5-yl], [0071;3-(3-Cl-Ph)-1-Me-PYR-5-yl], [0072;3-(4-Cl-Ph)-1-Me-PYR-5-yl], [0073;3-(2-Br-Ph)-1-Me-PYR-5-yl], [0074;3-(3-Br-Ph)-1-Me-PYR-5-yl], [0075;3-(4-Br-Ph)-1-Me-PYR-5-yl], [0076;3-(2-Me-Ph)-1-Me-PYR-5-yl], [0077;3-(3-Me-Ph)-1-Me-PYR-5-yl], [0078;3-(4-Me-Ph)-1-Me-PYR-5-yl], [0079;3-(2-Et-Ph)-1-Me-PYR-5-yl], [0080;3-(3-Et-Ph)-1-Me-PYR-5-yl], [0081;3-(4-Et-Ph)-1-Me-PYR-5-yl], [0082;3-(2-CF3-Ph)-1-Me-PYR-5-yl], [0083;3-(3-CF3-Ph)-1-Me-PYR-5-yl], [0084;3-(4-CF3-Ph)-1-Me-PYR-5-yl], [0085;3-(2-OMe-Ph)-1-Me-PYR-5-yl], [0086;3-(3-OMe-Ph)-1-Me-PYR-5-yl], [0087;3-(4-OMe-Ph)-1-Me-PYR-5-yl], [0088;3-(2-OEt-Ph)-1-Me-PYR-5-yl], [0089;3-(3-OEt-Ph)-1-Me-PYR-5-yl], [0090;3-(4-OEt-Ph)-1-Me-PYR-5-yl], [0091;3-(4-F-2-F-Ph)-1-Me-PYR-5-yl], [0092;3-(4-Cl-2-F-Ph)-1-Me-PYR-5-yl], [0093;3-(4-Br-2-F-Ph)-1-Me-PYR-5-yl], [0094;3-(4-Me-2-F-Ph)-1-Me-PYR-5-yl], [0095;3-(4-Et-2-F-Ph)-1-Me-PYR-5-yl], [0096;3-(4-CF3-2-F-Ph)-1-Me-PYR-5-yl], [0097;3-(4-OMe-2-F-Ph)-1-Me-PYR-5-yl], [0098;3-(4-OEt-2-F-Ph)-1-Me-PYR-5-yl], [0099;3-(4-F-2-Cl-Ph)-1-Me-PYR-5-yl], [0100;3-(4-Cl-2-Cl-Ph)-1-Me-PYR-5-yl], [0101;3-(4-Br-2-Cl-Ph)-1-Me-PYR-5-yl], [0102;3-(4-Me-2-Cl-Ph)-1-Me-PYR-5-yl], [0103;3-(4-Et-2-Cl-Ph)-1-Me-PYR-5-yl], [0104;3-(4-CF3-2-Cl-Ph)-1-Me-PYR-5-yl], [0105;3-(4-OMe-2-Cl-Ph)-1-Me-PYR-5-yl], [0106;3-(4-OEt-2-Cl-Ph)-1-Me-PYR-5-yl], [0107;3-(4-F-2-Me-Ph)-1-Me-PYR-5-yl], [0108;3-(4-Cl-2-Me-Ph)-1-Me-PYR-5-yl], [0109;3-(4-Br-2-Me-Ph)-1-Me-PYR-5-yl], [0110;3-(4-Me-2-Me-Ph)-1-Me-PYR-5-yl], [0111;3-(4-Et-2-Me-Ph)-1-Me-PYR-5-yl], [0112;3-(4-CF3-2-Me-Ph)-1-Me-PYR-5-yl], [0113;3-(4-OMe-2-Me-Ph)-1-Me-PYR-5-yl], [0114;3-(4-OEt-2-Me-Ph)-1-Me-PYR-5-yl], [0115;3-(4-F-2-OMe-Ph)-1-Me-PYR-5-yl], [0116;3-(4-Cl-2-OMe-Ph)-1-Me-PYR-5-yl], [0117;3-(4-Br-2-OMe-Ph)-1-Me-PYR-5-yl], [0118;3-(4-Me-2-OMe-Ph)-1-Me-PYR-5-yl], [0119;3-(4-Et-2-OMe-Ph)-1-Me-PYR-5-yl], [0120;3-(4-CF3-2-OMe-Ph)-1-Me-PYR-5-yl], [0121;3-(4-OMe-2-OMe-Ph)-1-Me-PYR-5-yl], [0122;3-(4-OEt-2-OMe-Ph)-1-Me-PYR-5-yl], [0123;3-(4-F-2-OEt-Ph)-1-Me-PYR-5-yl], [0124;3-(4-Cl-2-OEt-Ph)-1-Me-PYR-5-yl], [0125;3-(4-Br-2-OEt-Ph)-1-Me-PYR-5-yl], [0126;3-(4-Me-2-OEt-Ph)-1-Me-PYR-5-yl], [0127;3-(4-Et-2-OEt-Ph)-1-Me-PYR-5-yl], [0128;3-(4-CF3-2-OEt-Ph)-1-Me-PYR-5-yl], [0129;3-(4-OMe-2-OEt-Ph)-1-Me-PYR-5-yl], [0130;3-(4-OEt-2-OEt-Ph)-1-Me-PYR-5-yl], [0131;5-Ph-1-Me-PYR-3-yl], [0132;5-(2-F-Ph)-1-Me-PYR-3-yl], [0133;5-(3-F-Ph)-1-Me-PYR-3-yl], [0134;5-(4-F-Ph)-1-Me-PYR-3-yl], [0135;5-(2-Cl-Ph)-1-Me-PYR-3-yl], [0136;5-(3-Cl-Ph)-1-Me-PYR-3-yl], [0137;5-(4-Cl-Ph)-1-Me-PYR-3-yl], [0138;5-(2-Br-Ph)-1-Me-PYR-3-yl], [0139;5-(3-Br-Ph)-1-Me-PYR-3-yl], [0140;5-(4-Br-Ph)-1-Me-PYR-3-yl], [0141;5-(2-Me-Ph)-1-Me-PYR-3-yl], [0142;5-(3-Me-Ph)-1-Me-PYR-3-yl], [0143;5-(4-Me-Ph)-1-Me-PYR-3-yl], [0144;5-(2-Et-Ph)-1-Me-PYR-3-yl], [0145;5-(3-Et-Ph)-1-Me-PYR-3-yl], [0146;5-(4-Et-Ph)-1-Me-PYR-3-yl], [0147;5-(2-CF3-Ph)-1-Me-PYR-3-yl], [0148;5-(3-CF3-Ph)-1-Me-PYR-3-yl], [0149;5-(4-CF3-Ph)-1-Me-PYR-3-yl], [0150;5-(2-OMe-Ph)-1-Me-PYR-3-yl], [0151;5-(3-OMe-Ph)-1-Me-PYR-3-yl], [0152;5-(4-OMe-Ph)-1-Me-PYR-3-yl], [0153;5-(2-OEt-Ph)-1-Me-PYR-3-yl], [0154;5-(3-OEt-Ph)-1-Me-PYR-3-yl], [0155;5-(4-OEt-Ph)-1-Me-PYR-3-yl], [0156;5-(4-F-2-F-Ph)-1-Me-PYR-3-yl], [0157;5-(4-Cl-2-F-Ph)-1-Me-PYR-3-yl], [0158;5-(4-Br-2-F-Ph)-1-Me-PYR-3-yl], [0159;5-(4-Me-2-F-Ph)-1-Me-PYR-3-yl], [0160;5-(4-Et-2-F-Ph)-1-Me-PYR-3-yl], [0161;5-(4-CF3-2-F-Ph)-1-Me-PYR-3-yl], [0162;5-(4-OMe-2-F-Ph)-1-Me-PYR-3-yl], [0163;5-(4-OEt-2-F-Ph)-1-Me-PYR-3-yl], [0164;5-(4-F-2-Cl-Ph)-1-Me-PYR-3-yl], [0165;5-(4-Cl-2-Cl-Ph)-1-Me-PYR-3-yl], [0166;5-(4-Br-2-Cl-Ph)-1-Me-PYR-3-yl], [0167;5-(4-Me-2-Cl-Ph)-1-Me-PYR-3-yl], [0168;5-(4-Et-2-Cl-Ph)-1-Me-PYR-3-yl], [0169;5-(4-CF3-2-Cl-Ph)-1-Me-PYR-3-yl], [0170;5-(4-OMe-2-Cl-Ph)-1-Me-PYR-3-yl], [0171;5-(4-OEt-2-Cl-Ph)-1-Me-PYR-3-yl], [0172;5-(4-F-2-Me-Ph)-1-Me-PYR-3-yl], [0173;5-(4-Cl-2-Me-Ph)-1-Me-PYR-3-yl], [0174;5-(4-Br-2-Me-Ph)-1-Me-PYR-3-yl], [0175;5-(4-Me-2-Me-Ph)-1-Me-PYR-3-yl], [0176;5-(4-Et-2-Me-Ph)-1-Me-PYR-3-yl], [0177;5-(4-CF3-2-Me-Ph)-1-Me-PYR-3-yl], [0178;5-(4-OMe-2-Me-Ph)-1-Me-PYR-3-yl], [0179;5-(4-OEt-2-Me-Ph)-1-Me-PYR-3-yl], [0180;5-(4-F-2-OMe-Ph)-1-Me-PYR-3-yl], [0181;5-(4-Cl-2-OMe-Ph)-1-Me-PYR-3-yl], [0182;5-(4-Br-2-OMe-Ph)-1-Me-PYR-3-yl], [0183;5-(4-Me-2-OMe-Ph)-1-Me-PYR-3-yl], [0184;5-(4-Et-2-OMe-Ph)-1-Me-PYR-3-yl], [0185;5-(4-CF3-2-OMe-Ph)-1-Me-PYR-3-yl], [0186;5-(4-OMe-2-OMe-Ph)-1-Me-PYR-3-yl], [0187;5-(4-OEt-2-OMe-Ph)-1-Me-PYR-3-yl], [0188;5-(4-F-2-OEt-Ph)-1-Me-PYR-3-yl], [0189;5-(4-Cl-2-OEt-Ph)-1-Me-PYR-3-yl], [0190;5-(4-Br-2-OEt-Ph)-1-Me-PYR-3-yl], [0191;5-(4-Me-2-OEt-Ph)-1-Me-PYR-3-yl], [0192;5-(4-Et-2-OEt-Ph)-1-Me-PYR-3-yl], [0193;5-(4-CF3-2-OEt-Ph)-1-Me-PYR-3-yl], [0194;5-(4-OMe-2-OEt-Ph)-1-Me-PYR-3-yl], [0195;5-(4-OEt-2-OEt-Ph)-1-Me-PYR-3-yl], [0196;1-phenyl-1,2,4-TRI-3-yl], [0197;1-(2-F-Ph)-1,2,4-TRI-3-yl], [0198;1-(3-F-Ph)-1,2,4-TRI-3-yl], [0199;1-(4-F-Ph)-1,2,4-TRI-3-yl], [0200;1-(2-Cl-Ph)-1,2,4-TRI-3-yl], [0201;1-(3-Cl-Ph)-1,2,4-TRI-3-yl], [0202;1-(4-Cl-Ph)-1,2,4-TRI-3-yl], [0203;1-(2-Br-Ph)-1,2,4-TRI-3-yl], [0204;1-

(3-Br-Ph)-1,2,4-TRI-3-yl], [0205;1-(4-Br-Ph)-1,2,4-TRI-3-yl], [0206;1-(2-Me-Ph)-1,2,4-TRI-3-yl], [0207;1-(3-Me-Ph)-1,2,4-TRI-3-yl], [0208;1-(4-Me-Ph)-1,2,4-TRI-3-yl], [0209;1-(2-Et-Ph)-1,2,4-TRI-3-yl], [0210;1-(3-Et-Ph)-1,2,4-TRI-3-yl], [0211;1-(4-Et-Ph)-1,2,4-TRI-3-yl], [0212;1-(2-CF3-Ph)-1,2,4-TRI-3-yl], [0213;1-(3-CF3-Ph)-1,2,4-TRI-3-yl], [0214;1-(4-CF3-Ph)-1,2,4-TRI-3-yl], [0215;1-(2-OMe-Ph)-1,2,4-TRI-3-yl], [0216;1-(3-OMe-Ph)-1,2,4-TRI-3-yl], [0217;1-(4-OMe-Ph)-1,2,4-TRI-3-yl], [0218;1-(2-OEt-Ph)-1,2,4-TRI-3-yl], [0219;1-(3-OEt-Ph)-1,2,4-TRI-3-yl], [0220;1-(4-OEt-Ph)-1,2,4-TRI-3-yl], [0221;1-(4-F-2-F-Ph)-1,2,4-TRI-3-yl], [0222;1-(4-Cl-2-F-Ph)-1,2,4-TRI-3-yl], [0223;1-(4-Br-2-F-Ph)-1,2,4-TRI-3-yl], [0224;1-(4-Me-2-F-Ph)-1,2,4-TRI-3-yl], [0225;1-(4-Et-2-F-Ph)-1,2,4-TRI-3-yl], [0226;1-(4-CF3-2-F-Ph)-1,2,4-TRI-3-yl], [0227;1-(4-OMe-2-F-Ph)-1,2,4-TRI-3-yl], [0228;1-(4-OEt-2-F-Ph)-1,2,4-TRI-3-yl], [0229;1-(4-F-2-Cl-Ph)-1,2,4-TRI-3-yl], [0230;1-(4-Cl-2-Cl-Ph)-1,2,4-TRI-3-yl], [0231;1-(4-Br-2-Cl-Ph)-1,2,4-TRI-3-yl], [0232;1-(4-Me-2-Cl-Ph)-1,2,4-TRI-3-yl], [0233;1-(4-Et-2-Cl-Ph)-1,2,4-TRI-3-yl], [0234;1-(4-CF3-2-Cl-Ph)-1,2,4-TRI-3-yl], [0235;1-(4-OMe-2-Cl-Ph)-1,2,4-TRI-3-yl], [0236;1-(4-OEt-2-Cl-Ph)-1,2,4-TRI-3-yl], [0237;1-(4-F-2-Me-Ph)-1,2,4-TRI-3-yl], [0238;1-(4-Cl-2-Me-Ph)-1,2,4-TRI-3-yl], [0239;1-(4-Br-2-Me-Ph)-1,2,4-TRI-3-yl], [0240;1-(4-Me-2-Me-Ph)-1,2,4-TRI-3-yl], [0241;1-(4-Et-2-Me-Ph)-1,2,4-TRI-3-yl], [0242;1-(4-CF3-2-Me-Ph)-1,2,4-TRI-3-yl], [0243;1-(4-OMe-2-Me-Ph)-1,2,4-TRI-3-yl], [0244;1-(4-OEt-2-Me-Ph)-1,2,4-TRI-3-yl], [0245;1-(4-F-2-OMe-Ph)-1,2,4-TRI-3-yl], [0246;1-(4-Cl-2-OMe-Ph)-1,2,4-TRI-3-yl], [0247;1-(4-Br-2-OMe-Ph)-1,2,4-TRI-3-yl], [0248;1-(4-Me-2-OMe-Ph)-1,2,4-TRI-3-yl], [0249;1-(4-Et-2-OMe-Ph)-1,2,4-TRI-3-yl], [0250;1-(4-CF3-2-OMe-Ph)-1,2,4-TRI-3-yl], [0251;1-(4-OMe-2-OMe-Ph)-1,2,4-TRI-3-yl], [0252;1-(4-OEt-2-OMe-Ph)-1,2,4-TRI-3-yl], [0253;1-(4-F-2-OEt-Ph)-1,2,4-TRI-3-yl], [0254;1-(4-Cl-2-OEt-Ph)-1,2,4-TRI-3-yl], [0255;1-(4-Br-2-OEt-Ph)-1,2,4-TRI-3-yl], [0256;1-(4-Me-2-OEt-Ph)-1,2,4-TRI-3-yl], [0257;1-(4-Et-2-OEt-Ph)-1,2,4-TRI-3-yl], [0258;1-(4-CF3-2-OEt-Ph)-1,2,4-TRI-3-yl], [0259;1-(4-OMe-2-OEt-Ph)-1,2,4-TRI-3-yl], [0260;1-(4-OEt-2-OEt-Ph)-1,2,4-TRI-3-yl], [0261;2-phenyl-1,2,3-TRI-4-yl], [0262;2-(2-F-Ph)-1,2,3-TRI-4-yl], [0263;2-(3-F-Ph)-1,2,3-TRI-4-yl], [0264;2-(4-F-Ph)-1,2,3-TRI-4-yl], [0265;2-(2-Cl-Ph)-1,2,3-TRI-4-yl], [0266;2-(3-Cl-Ph)-1,2,3-TRI-4-yl], [0267;2-(4-Cl-Ph)-1,2,3-TRI-4-yl], [0268;2-(2-Br-Ph)-1,2,3-TRI-4-yl], [0269;2-(3-Br-Ph)-1,2,3-TRI-4-yl], [0270;2-(4-Br-Ph)-1,2,3-TRI-4-yl], [0271;2-(2-Me-Ph)-1,2,3-TRI-4-yl], [0272;2-(3-Me-Ph)-1,2,3-TRI-4-yl], [0273;2-(4-Me-Ph)-1,2,3-TRI-4-yl], [0274;2-(2-Et-Ph)-1,2,3-TRI-4-yl], [0275;2-(3-Et-Ph)-1,2,3-TRI-4-yl], [0276;2-(4-Et-Ph)-1,2,3-TRI-4-yl], [0277;2-(2-CF3-Ph)-1,2,3-TRI-4-yl], [0278;2-(3-CF3-Ph)-1,2,3-TRI-4-yl], [0279;2-(4-CF3-Ph)-1,2,3-TRI-4-yl], [0280;2-(2-OMe-Ph)-1,2,3-TRI-4-yl], [0281;2-(3-OMe-Ph)-1,2,3-TRI-4-yl], [0282;2-(4-OMe-Ph)-1,2,3-TRI-4-yl], [0283;2-(2-OEt-Ph)-1,2,3-TRI-4-yl], [0284;2-(3-OEt-Ph)-1,2,3-TRI-4-yl], [0285;2-(4-OEt-Ph)-1,2,3-TRI-4-yl], [0286;2-(4-F-2-F-Ph)-1,2,3-TRI-4-yl], [0287;2-(4-Cl-2-F-Ph)-1,2,3-TRI-4-yl], [0288;2-(4-Br-2-F-Ph)-1,2,3-TRI-4-yl], [0289;2-(4-Me-2-F-Ph)-1,2,3-TRI-4-yl], [0290;2-(4-Et-2-F-Ph)-1,2,3-TRI-4-yl], [0291;2-(4-CF3-2-F-Ph)-1,2,3-TRI-4-yl], [0292;2-(4-OMe-2-F-Ph)-1,2,3-TRI-4-yl], [0293;2-(4-OEt-2-F-Ph)-1,2,3-TRI-4-yl], [0294;2-(4-F-2-Cl-Ph)-1,2,3-TRI-4-yl], [0295;2-(4-Cl-2-Cl-Ph)-1,2,3-TRI-4-yl], [0296;2-(4-Br-2-Cl-Ph)-1,2,3-TRI-4-yl], [0297;2-(4-Me-2-Cl-Ph)-1,2,3-TRI-4-yl], [0298;2-(4-Et-2-Cl-Ph)-1,2,3-TRI-4-yl], [0299;2-(4-CF3-2-Cl-Ph)-1,2,3-TRI-4-yl], [0300;2-(4-OMe-2-Cl-Ph)-1,2,3-TRI-4-yl], [0301;2-(4-OEt-2-Cl-Ph)-1,2,3-TRI-4-yl], [0302;2-(4-F-2-Me-Ph)-1,2,3-TRI-4-yl], [0303;2-(4-Cl-2-Me-Ph)-1,2,3-TRI-4-yl], [0304;2-(4-Br-2-Me-Ph)-1,2,3-TRI-4-yl], [0305;2-(4-Me-2-Me-Ph)-1,2,3-TRI-4-yl], [0306;2-(4-Et-2-Me-Ph)-1,2,3-TRI-4-yl], [0307;2-(4-CF3-2-Me-Ph)-1,2,3-TRI-4-yl], [0308;2-(4-OMe-2-Me-Ph)-1,2,3-TRI-4-yl], [0309;2-(4-OEt-2-Me-Ph)-1,2,3-TRI-4-yl], [0310;2-(4-F-2-OMe-Ph)-1,2,3-TRI-4-yl], [0311;2-(4-Cl-2-OMe-Ph)-1,2,3-TRI-4-yl], [0312;2-(4-Br-2-OMe-Ph)-1,2,3-TRI-4-yl], [0313;2-(4-Me-2-OMe-Ph)-1,2,3-TRI-4-yl], [0314;2-(4-Et-2-OMe-Ph)-1,2,3-TRI-4-yl], [0315;2-(4-CF3-2-OMe-Ph)-1,2,3-TRI-4-yl], [0316;2-(4-OMe-2-OMe-Ph)-1,2,3-TRI-4-yl], [0317;2-(4-OEt-2-OMe-Ph)-1,2,3-TRI-4-yl], [0318;2-(4-F-2-OEt-Ph)-1,2,3-TRI-4-yl], [0319;2-(4-Cl-2-OEt-Ph)-1,2,3-TRI-4-yl], [0320;2-(4-Br-2-OEt-Ph)-1,2,3-TRI-4-yl], [0321;2-(4-Me-2-OEt-Ph)-1,2,3-TRI-4-yl], [0322;2-(4-Et-2-OEt-Ph)-1,2,3-TRI-4-yl], [0323;2-(4-CF3-2-OEt-Ph)-1,2,3-TRI-4-yl], [0324;2-(4-OMe-2-OEt-Ph)-1,2,3-TRI-4-yl], [0325;2-(4-OEt-2-OEt-Ph)-1,2,3-TRI-4-yl], [0326;2-phenylTET-5-yl], [0327;2-(2-F-Ph)TET-5-yl], [0328;2-(3-F-Ph)TET-5-yl], [0329;2-(4-F-Ph)TET-5-yl], [0330;2-(2-Cl-Ph)TET-5-yl], [0331;2-(3-Cl-Ph)TET-5-yl], [0332;2-(4-Cl-Ph)TET-5-yl], [0333;2-(2-Br-Ph)TET-5-yl], [0334;2-(3-Br-Ph)TET-5-yl], [0335;2-(4-Br-Ph)TET-5-yl], [0336;2-(2-Me-Ph)TET-5-yl], [0337;2-(3-Me-Ph)TET-5-yl], [0338;2-(4-Me-Ph)TET-5-yl], [0339;2-(2-Et-Ph)TET-5-yl], [0340;2-(3-Et-Ph)TET-5-yl], [0341;2-(4-Et-Ph)TET-5-yl], [0342;2-(2-CF3-Ph)TET-5-yl], [0343;2-(3-CF3-Ph)TET-5-yl], [0344;2-(4-CF3-Ph)TET-5-yl], [0345;2-(2-OMe-Ph)TET-5-yl], [0346;2-(3-OMe-Ph)TET-5-yl], [0347;2-(4-OMe-Ph)TET-5-yl], [0348;2-(2-OEt-Ph)TET-5-yl], [0349;2-(3-OEt-Ph)TET-5-yl], [0350;2-(4-OEt-Ph)TET-5-yl], [0351;2-(4-F-2-F-Ph)TET-5-yl], [0352;2-(4-Cl-2-F-Ph)TET-5-yl], [0353;2-(4-Br-2-F-Ph)TET-5-yl], [0354;2-(4-Me-2-F-Ph)TET-5-yl], [0355;2-(4-Et-2-F-Ph)TET-5-yl], [0356;2-(4-CF3-2-F-Ph)TET-5-yl], [0357;2-(4-OMe-2-F-Ph)TET-5-yl], [0358;2-(4-OEt-2-F-Ph)TET-5-yl], [0359;2-(4-F-2-Cl-Ph)TET-5-yl], [0360;2-(4-Cl-2-Cl-Ph)TET-5-yl], [0361;2-(4-Br-2-Cl-Ph)TET-5-yl], [0362;2-(4-Me-2-Cl-Ph)TET-5-yl], [0363;2-(4-Et-2-Cl-Ph)TET-5-yl], [0364;2-(4-CF3-2-Cl-Ph)TET-5-yl], [0365;2-(4-OMe-2-Cl-Ph)TET-5-yl], [0366;2-(4-OEt-2-Cl-Ph)TET-5-yl], [0367;2-(4-F-2-Me-Ph)TET-5-yl], [0368;2-(4-Cl-2-Me-Ph)TET-5-yl], [0369;2-(4-Br-2-Me-Ph)TET-5-yl], [0370;2-(4-Me-2-Me-Ph)TET-5-yl], [0371;2-(4-Et-2-Me-Ph)TET-5-yl], [0372;2-(4-CF3-2-Me-Ph)TET-5-yl], [0373;2-(4-OMe-2-Me-Ph)TET-5-yl], [0374;2-(4-OEt-2-Me-Ph)TET-5-yl], [0375;2-(4-F-2-OMe-Ph)TET-5-yl], [0376;2-(4-Cl-2-OMe-Ph)TET-5-yl], [0377;2-(4-Br-2-OMe-Ph)TET-5-yl], [0378;2-(4-Me-2-OMe-Ph)TET-5-yl], [0379;2-(4-Et-2-OMe-Ph)TET-5-yl], [0380;2-(4-CF3-2-OMe-Ph)TET-5-yl], [0381;2-(4-OMe-2-OMe-Ph)TET-5-yl], [0382;2-(4-OEt-2-OMe-Ph)TET-5-yl], [0383;2-(4-F-2-OEt-Ph)TET-5-yl], [0384;2-(4-Cl-2-OEt-Ph)TET-5-yl], [0385;2-(4-Br-2-OEt-Ph)TET-5-yl], [0386;2-(4-Me-2-OEt-Ph)TET-5-yl], [0387;2-(4-Et-2-OEt-Ph)TET-5-yl], [0388;2-(4-CF3-2-OEt-Ph)TET-5-yl], [0389;2-(4-OMe-2-OEt-Ph)TET-5-yl], [0390;2-(4-OEt-2-OEt-Ph)TET-5-yl], [0391;3-phenylTHI-5-yl], [0392;3-(2-F-Ph)THI-5-yl], [0393;3-(3-F-Ph)THI-5-yl], [0394;3-(4-F-Ph)THI-5-yl], [0395;3-(2-Cl-Ph)THI-5-yl], [0396;3-(3-Cl-Ph)THI-5-yl], [0397;3-(4-Cl-Ph)THI-5-yl], [0398;3-(2-Br-Ph)THI-5-yl], [0399;3-(3-Br-Ph)THI-5-yl], [0400;3-(4-Br-Ph)THI-5-yl], [0401;3-(2-Me-Ph)THI-5-yl], [0402;3-(3-Me-Ph)THI-5-yl], [0403;3-(4-Me-Ph)THI-5-yl], [0404;3-(2-Et-Ph)THI-5-yl], [0405;3-(3-Et-Ph)THI-5-yl], [0406;3-(4-Et-Ph)THI-5-yl], [0407;3-(2-CF3-Ph)THI-5-yl], [0408;3-(3-CF3-Ph)THI-5-yl], [0409;3-(4-CF3-Ph)THI-5-yl], [0410;3-(2-OMe-Ph)

THI-5-yl], [0411;3-(3-OMe-Ph)THI-5-yl], [0412;3-(4-OMe-Ph)THI-5-yl], [0413;3-(2-OEt-Ph)THI-5-yl], [0414;3-(3-OEt-Ph)THI-5-yl], [0415;3-(4-OEt-Ph)THI-5-yl], [0416;3-(4-F-2-F-Ph)THI-5-yl], [0417;3-(4-Cl-2-F-Ph)THI-5-yl], [0418;3-(4-Br-2-F-Ph)THI-5-yl], [0419;3-(4-Me-2-F-Ph)THI-5-yl], [0420;3-(4-Et-2-F-Ph)THI-5-yl], [0421;3-(4-CF3-2-F-Ph)THI-5-yl], [0422;3-(4-OMe-2-F-Ph)THI-5-yl], [0423;3-(4-OEt-2-F-Ph)THI-5-yl], [0424;3-(4-F-2-Cl-Ph)THI-5-yl], [0425;3-(4-Cl-2-Cl-Ph)THI-5-yl], [0426;3-(4-Br-2-Cl-Ph)THI-5-yl], [0427;3-(4-Me-2-Cl-Ph)THI-5-yl], [0428;3-(4-Et-2-Cl-Ph)THI-5-yl], [0429;3-(4-CF3-2-Cl-Ph)THI-5-yl], [0430;3-(4-OMe-2-Cl-Ph)THI-5-yl], [0431;3-(4-OEt-2-Cl-Ph)THI-5-yl], [0432;3-(4-F-2-Me-Ph)THI-5-yl], [0433;3-(4-Cl-2-Me-Ph)THI-5-yl], [0434;3-(4-Br-2-Me-Ph)THI-5-yl], [0435;3-(4-Me-2-Me-Ph)THI-5-yl], [0436;3-(4-Et-2-Me-Ph)THI-5-yl], [0437;3-(4-CF3-2-Me-Ph)THI-5-yl], [0438;3-(4-OMe-2-Me-Ph)THI-5-yl], [0439;3-(4-OEt-2-Me-Ph)THI-5-yl], [0440;3-(4-F-2-OMe-Ph)THI-5-yl], [0441;3-(4-Cl-2-OMe-Ph)THI-5-yl], [0442;3-(4-Br-2-OMe-Ph)THI-5-yl], [0443;3-(4-Me-2-OMe-Ph)THI-5-yl], [0444;3-(4-Et-2-OMe-Ph)THI-5-yl], [0445;3-(4-CF3-2-OMe-Ph)THI-5-yl], [0446;3-(4-OMe-2-OMe-Ph)THI-5-yl], [0447;3-(4-OEt-2-OMe-Ph)THI-5-yl], [0448;3-(4-F-2-OEt-Ph)THI-5-yl], [0449;3-(4-Cl-2-OEt-Ph)THI-5-yl], [0450;3-(4-Br-2-OEt-Ph)THI-5-yl], [0451;3-(4-Me-2-OEt-Ph)THI-5-yl], [0452;3-(4-Et-2-OEt-Ph)THI-5-yl], [0453;3-(4-CF3-2-OEt-Ph)THI-5-yl], [0454;3-(4-OMe-2-OEt-Ph)THI-5-yl], [0455;3-(4-OEt-2-OEt-Ph)THI-5-yl], [0456;5-phenylTHI-2-yl], [0457;5-(2-F-Ph)THI-2-yl], [0458;5-(3-F-Ph)THI-2-yl], [0459;5-(4-F-Ph)THI-2-yl], [0460;5-(2-Cl-Ph)THI-2-yl], [0461;5-(3-Cl-Ph)THI-2-yl], [0462;5-(4-Cl-Ph)THI-2-yl], [0463;5-(2-Br-Ph)THI-2-yl], [0464;5-(3-Br-Ph)THI-2-yl], [0465;5-(4-Br-Ph)THI-2-yl], [0466;5-(2-Me-Ph)THI-2-yl], [0467;5-(3-Me-Ph)THI-2-yl], [0468;5-(4-Me-Ph)THI-2-yl], [0469;5-(2-Et-Ph)THI-2-yl], [0470;5-(3-Et-Ph)THI-2-yl], [0471;5-(4-Et-Ph)THI-2-yl], [0472;5-(2-CF3-Ph)THI-2-yl], [0473;5-(3-CF3-Ph)THI-2-yl], [0474;5-(4-CF3-Ph)THI-2-yl], [0475;5-(2-OMe-Ph)THI-2-yl], [0476;5-(3-OMe-Ph)THI-2-yl], [0477;5-(4-OMe-Ph)THI-2-yl], [0478;5-(2-OEt-Ph)THI-2-yl], [0479;5-(3-OEt-Ph)THI-2-yl], [0480;5-(4-OEt-Ph)THI-2-yl], [0481;5-(4-F-2-F-Ph)THI-2-yl], [0482;5-(4-Cl-2-F-Ph)THI-2-yl], [0483;5-(4-Br-2-F-Ph)THI-2-yl], [0484;5-(4-Me-2-F-Ph)THI-2-yl], [0485;5-(4-Et-2-F-Ph)THI-2-yl], [0486;5-(4-CF3-2-F-Ph)THI-2-yl], [0487;5-(4-OMe-2-F-Ph)THI-2-yl], [0488;5-(4-OEt-2-F-Ph)THI-2-yl], [0489;5-(4-F-2-Cl-Ph)THI-2-yl], [0490;5-(4-Cl-2-Cl-Ph)THI-2-yl], [0491;5-(4-Br-2-Cl-Ph)THI-2-yl], [0492;5-(4-Me-2-Cl-Ph)THI-2-yl], [0493;5-(4-Et-2-Cl-Ph)THI-2-yl], [0494;5-(4-CF3-2-Cl-Ph)THI-2-yl], [0495;5-(4-OMe-2-Cl-Ph)THI-2-yl], [0496;5-(4-OEt-2-Cl-Ph)THI-2-yl], [0497;5-(4-F-2-Me-Ph)THI-2-yl], [0498;5-(4-Cl-2-Me-Ph)THI-2-yl], [0499;5-(4-Br-2-Me-Ph)THI-2-yl], [0500;5-(4-Me-2-Me-Ph)THI-2-yl],
[0501;5-(4-Et-2-Me-Ph)THI-2-yl], [0502;5-(4-CF3-2-Me-Ph)THI-2-yl], [0503;5-(4-OMe-2-Me-Ph)THI-2-yl], [0504;5-(4-OEt-2-Me-Ph)THI-2-yl], [0505;5-(4-F-2-OMe-Ph)THI-2-yl], [0506;5-(4-Cl-2-OMe-Ph)THI-2-yl], [0507;5-(4-Br-2-OMe-Ph)THI-2-yl], [0508;5-(4-Me-2-OMe-Ph)THI-2-yl], [0509;5-(4-Et-2-OMe-Ph)THI-2-yl], [0510;5-(4-CF3-2-OMe-Ph)THI-2-yl], [0511;5-(4-OMe-2-OMe-Ph)THI-2-yl], [0512;5-(4-OEt-2-OMe-Ph)THI-2-yl], [0513;5-(4-F-2-OEt-Ph)THI-2-yl], [0514;5-(4-Cl-2-OEt-Ph)THI-2-yl], [0515;5-(4-Br-2-OEt-Ph)THI-2-yl], [0516;5-(4-Me-2-OEt-Ph)THI-2-yl], [0517;5-(4-Et-2-OEt-Ph)THI-2-yl], [0518;5-(4-CF3-2-OEt-Ph)THI-2-yl], [0519;5-(4-OMe-2-OEt-Ph)THI-2-yl], [0520;5-(4-OEt-2-OEt-Ph)THI-2-yl], [0521;5-phenylTHI-3-yl], [0522;5-(2-F-Ph)THI-3-yl], [0523;5-(3-F-Ph)THI-3-yl], [0524;5-(4-F-Ph)THI-3-yl], [0525;5-(2-Cl-Ph)THI-3-yl], [0526;5-(3-Cl-Ph)THI-3-yl], [0527;5-(4-Cl-Ph)THI-3-yl], [0528;5-(2-Br-Ph)THI-3-yl], [0529;5-(3-Br-Ph)THI-3-yl], [0530;5-(4-Br-Ph)THI-3-yl], [0531;5-(2-Me-Ph)THI-3-yl], [0532;5-(3-Me-Ph)THI-3-yl], [0533;5-(4-Me-Ph)THI-3-yl], [0534;5-(2-Et-Ph)THI-3-yl], [0535;5-(3-Et-Ph)THI-3-yl], [0536;5-(4-Et-Ph)THI-3-yl], [0537;5-(2-CF3-Ph)THI-3-yl], [0538;5-(3-CF3-Ph)THI-3-yl], [0539;5-(4-CF3-Ph)THI-3-yl], [0540;5-(2-OMe-Ph)THI-3-yl], [0541;5-(3-OMe-Ph)THI-3-yl], [0542;5-(4-OMe-Ph)THI-3-yl], [0543;5-(2-OEt-Ph)THI-3-yl], [0544;5-(3-OEt-Ph)THI-3-yl], [0545;5-(4-OEt-Ph)THI-3-yl], [0546;5-(4-F-2-F-Ph)THI-3-yl], [0547;5-(4-Cl-2-F-Ph)THI-3-yl], [0548;5-(4-Br-2-F-Ph)THI-3-yl], [0549;5-(4-Me-2-F-Ph)THI-3-yl], [0550;5-(4-Et-2-F-Ph)THI-3-yl], [0551;5-(4-CF3-2-F-Ph)THI-3-yl], [0552;5-(4-OMe-2-F-Ph)THI-3-yl], [0553;5-(4-OEt-2-F-Ph)THI-3-yl], [0554;5-(4-F-2-Cl-Ph)THI-3-yl], [0555;5-(4-Cl-2-Cl-Ph)THI-3-yl], [0556;5-(4-Br-2-Cl-Ph)THI-3-yl], [0557;5-(4-Me-2-Cl-Ph)THI-3-yl], [0558;5-(4-Et-2-Cl-Ph)THI-3-yl], [0559;5-(4-CF3-2-Cl-Ph)THI-3-yl], [0560;5-(4-OMe-2-Cl-Ph)THI-3-yl], [0561;5-(4-OEt-2-Cl-Ph)THI-3-yl], [0562;5-(4-F-2-Me-Ph)THI-3-yl], [0563;5-(4-Cl-2-Me-Ph)THI-3-yl], [0564;5-(4-Br-2-Me-Ph)THI-3-yl], [0565;5-(4-Me-2-Me-Ph)THI-3-yl], [0566;5-(4-Et-2-Me-Ph)THI-3-yl], [0567;5-(4-CF3-2-Me-Ph)THI-3-yl], [0568;5-(4-OMe-2-Me-Ph)THI-3-yl], [0569;5-(4-OEt-2-Me-Ph)THI-3-yl], [0570;5-(4-F-2-OMe-Ph)THI-3-yl], [0571;5-(4-Cl-2-OMe-Ph)THI-3-yl], [0572;5-(4-Br-2-OMe-Ph)THI-3-yl], [0573;5-(4-Me-2-OMe-Ph)THI-3-yl], [0574;5-(4-Et-2-OMe-Ph)THI-3-yl], [0575;5-(4-CF3-2-OMe-Ph)THI-3-yl], [0576;5-(4-OMe-2-OMe-Ph)THI-3-yl], [0577;5-(4-OEt-2-OMe-Ph)THI-3-yl], [0578;5-(4-F-2-OEt-Ph)THI-3-yl], [0579;5-(4-Cl-2-OEt-Ph)THI-3-yl], [0580;5-(4-Br-2-OEt-Ph)THI-3-yl], [0581;5-(4-Me-2-OEt-Ph)THI-3-yl], [0582;5-(4-Et-2-OEt-Ph)THI-3-yl], [0583;5-(4-CF3-2-OEt-Ph)THI-3-yl], [0584;5-(4-OMe-2-OEt-Ph)THI-3-yl], [0585;5-(4-OEt-2-OEt-Ph)THI-3-yl], [0586;3-phenylFUR-5-yl], [0587;3-(2-F-Ph)FUR-5-yl], [0588;3-(3-F-Ph)FUR-5-yl], [0589;3-(4-F-Ph)FUR-5-yl], [0590;3-(2-Cl-Ph)FUR-5-yl], [0591;3-(3-Cl-Ph)FUR-5-yl], [0592;3-(4-Cl-Ph)FUR-5-yl], [0593;3-(2-Br-Ph)FUR-5-yl], [0594;3-(3-Br-Ph)FUR-5-yl], [0595;3-(4-Br-Ph)FUR-5-yl], [0596;3-(2-Me-Ph)FUR-5-yl], [0597;3-(3-Me-Ph)FUR-5-yl], [0598;3-(4-Me-Ph)FUR-5-yl], [0599;3-(2-Et-Ph)FUR-5-yl], [0600;3-(3-Et-Ph)FUR-5-yl], [0601;3-(4-Et-Ph)FUR-5-yl], [0602;3-(2-CF3-Ph)FUR-5-yl], [0603;3-(3-CF3-Ph)FUR-5-yl], [0604;3-(4-CF3-Ph)FUR-5-yl], [0605;3-(2-OMe-Ph)FUR-5-yl], [0606;3-(3-OMe-Ph)FUR-5-yl], [0607;3-(4-OMe-Ph)FUR-5-yl], [0608;3-(2-OEt-Ph)FUR-5-yl], [0609;3-(3-OEt-Ph)FUR-5-yl], [0610;3-(4-OEt-Ph)FUR-5-yl], [0611;3-(4-F-2-F-Ph)FUR-5-yl], [0612;3-(4-Cl-2-F-Ph)FUR-5-yl], [0613;3-(4-Br-2-F-Ph)FUR-5-yl], [0614;3-(4-Me-2-F-Ph)FUR-5-yl], [0615;3-(4-Et-2-F-Ph)FUR-5-yl], [0616;3-(4-CF3-2-F-Ph)FUR-5-yl], [0617;3-(4-OMe-2-F-Ph)FUR-5-yl], [0618;3-(4-OEt-2-F-Ph)FUR-5-yl], [0619;3-(4-F-2-Cl-Ph)FUR-5-yl], [0620;3-(4-Cl-2-Cl-Ph)FUR-5-yl], [0621;3-(4-Br-2-Cl-Ph)FUR-5-yl], [0622;3-(4-Me-2-Cl-Ph)FUR-5-yl], [0623;3-(4-Et-2-Cl-Ph)FUR-5-yl], [0624;3-(4-CF3-2-Cl-Ph)FUR-5-yl], [0625;3-(4-OMe-2-Cl-Ph)FUR-5-yl], [0626;3-(4-OEt-2-Cl-Ph)FUR-5-yl], [0627;3-(4-F-2-Me-Ph)FUR-5-yl], [0628;3-(4-Cl-2-Me-Ph)FUR-5-yl], [0629;3-(4-Br-2-Me-Ph)FUR-5-yl], [0630;3-(4-Me-2-Me-Ph)FUR-5-yl], [0631;3-(4-Et-2-Me-Ph)FUR-5-yl], [0632;3-(4-CF3-2-Me-Ph)FUR-5-yl], [0633;3-(4-OMe-2-Me-Ph)FUR-5-yl], [0634;3-(4-OEt-2-Me-Ph)FUR-5-yl], [0635;3-(4-F-2-OMe-Ph)FUR-5-yl], [0636;3-(4-Cl-2-OMe-Ph)FUR-5-yl], [0637;3-(4-Br-2-OMe-Ph)FUR-5-yl], [0638;3-(4-Me-2-OMe-Ph)

FUR-5-yl], [0639;3-(4-Et-2-OMe-Ph)FUR-5-yl], [0640;3-(4-CF3-2-OMe-Ph)FUR-5-yl], [0641;3-(4-OMe-2-OMe-Ph)FUR-5-yl], [0642;3-(4-OEt-2-OMe-Ph)FUR-5-yl], [0643;3-(4-F-2-OEt-Ph)FUR-5-yl], [0644;3-(4-Cl-2-OEt-Ph)FUR-5-yl], [0645;3-(4-Br-2-OEt-Ph)FUR-5-yl], [0646;3-(4-Me-2-OEt-Ph)FUR-5-yl], [0647;3-(4-Et-2-OEt-Ph)FUR-5-yl], [0648;3-(4-CF3-2-OEt-Ph)FUR-5-yl], [0649;3-(4-OMe-2-OEt-Ph)FUR-5-yl], [0650;3-(4-OEt-2-OEt-Ph)FUR-5-yl], [0651;5-phenylFUR-2-yl], [0652;5-(2-F-Ph)FUR-2-yl], [0653;5-(3-F-Ph)FUR-2-yl], [0654;5-(4-F-Ph)FUR-2-yl], [0655;5-(2-Cl-Ph)FUR-2-yl], [0656;5-(3-Cl-Ph)FUR-2-yl], [0657;5-(4-Cl-Ph)FUR-2-yl], [0658;5-(2-Br-Ph)FUR-2-yl], [0659;5-(3-Br-Ph)FUR-2-yl], [0660;5-(4-Br-Ph)FUR-2-yl], [0661;5-(2-Me-Ph)FUR-2-yl], [0662;5-(3-Me-Ph)FUR-2-yl], [0663;5-(4-Me-Ph)FUR-2-yl], [0664;5-(2-Et-Ph)FUR-2-yl], [0665;5-(3-Et-Ph)FUR-2-yl], [0666;5-(4-Et-Ph)FUR-2-yl], [0667;5-(2-CF3-Ph)FUR-2-yl], [0668;5-(3-CF3-Ph)FUR-2-yl], [0669;5-(4-CF3-Ph)FUR-2-yl], [0670;5-(2-OMe-Ph)FUR-2-yl], [0671;5-(3-OMe-Ph)FUR-2-yl], [0672;5-(4-OMe-Ph)FUR-2-yl], [0673;5-(2-OEt-Ph)FUR-2-yl], [0674;5-(3-OEt-Ph)FUR-2-yl], [0675;5-(4-OEt-Ph)FUR-2-yl], [0676;5-(4-F-2-F-Ph)FUR-2-yl], [0677;5-(4-Cl-2-F-Ph)FUR-2-yl], [0678;5-(4-Br-2-F-Ph)FUR-2-yl], [0679;5-(4-Me-2-F-Ph)FUR-2-yl], [0680;5-(4-Et-2-F-Ph)FUR-2-yl], [0681;5-(4-CF3-2-F-Ph)FUR-2-yl], [0682;5-(4-OMe-2-F-Ph)FUR-2-yl], [0683;5-(4-OEt-2-F-Ph)FUR-2-yl], [0684;5-(4-F-2-Cl-Ph)FUR-2-yl], [0685;5-(4-Cl-2-Cl-Ph)FUR-2-yl], [0686;5-(4-Br-2-Cl-Ph)FUR-2-yl], [0687;5-(4-Me-2-Cl-Ph)FUR-2-yl], [0688;5-(4-Et-2-Cl-Ph)FUR-2-yl], [0689;5-(4-CF3-2-Cl-Ph)FUR-2-yl], [0690;5-(4-OMe-2-Cl-Ph)FUR-2-yl], [0691;5-(4-OEt-2-Cl-Ph)FUR-2-yl], [0692;5-(4-F-2-Me-Ph)FUR-2-yl], [0693;5-(4-Cl-2-Me-Ph)FUR-2-yl], [0694;5-(4-Br-2-Me-Ph)FUR-2-yl], [0695;5-(4-Me-2-Me-Ph)FUR-2-yl], [0696;5-(4-Et-2-Me-Ph)FUR-2-yl], [0697;5-(4-CF3-2-Me-Ph)FUR-2-yl], [0698;5-(4-OMe-2-Me-Ph)FUR-2-yl], [0699;5-(4-OEt-2-Me-Ph)FUR-2-yl], [0700;5-(4-F-2-OMe-Ph)FUR-2-yl], [0701;5-(4-Cl-2-OMe-Ph)FUR-2-yl], [0702;5-(4-Br-2-OMe-Ph)FUR-2-yl], [0703;5-(4-Me-2-OMe-Ph)FUR-2-yl], [0704;5-(4-Et-2-OMe-Ph)FUR-2-yl], [0705;5-(4-CF3-2-OMe-Ph)FUR-2-yl], [0706;5-(4-OMe-2-OMe-Ph)FUR-2-yl], [0707;5-(4-OEt-2-OMe-Ph)FUR-2-yl], [0708;5-(4-F-2-OEt-Ph)FUR-2-yl], [0709;5-(4-Cl-2-OEt-Ph)FUR-2-yl], [0710;5-(4-Br-2-OEt-Ph)FUR-2-yl], [0711;5-(4-Me-2-OEt-Ph)FUR-2-yl], [0712;5-(4-Et-2-OEt-Ph)FUR-2-yl], [0713;5-(4-CF3-2-OEt-Ph)FUR-2-yl], [0714;5-(4-OMe-2-OEt-Ph)FUR-2-yl], [0715;5-(4-OEt-2-OEt-Ph)FUR-2-yl], [0716;5-phenylFUR-3-yl], [0717;5-(2-F-Ph)FUR-3-yl], [0718;5-(3-F-Ph)FUR-3-yl], [0719;5-(4-F-Ph)FUR-3-yl], [0720;5-(2-Cl-Ph)FUR-3-yl], [0721;5-(3-Cl-Ph)FUR-3-yl], [0722;5-(4-Cl-Ph)FUR-3-yl], [0723;5-(2-Br-Ph)FUR-3-yl], [0724;5-(3-Br-Ph)FUR-3-yl], [0725;5-(4-Br-Ph)FUR-3-yl], [0726;5-(2-Me-Ph)FUR-3-yl], [0727;5-(3-Me-Ph)FUR-3-yl], [0728;5-(4-Me-Ph)FUR-3-yl], [0729;5-(2-Et-Ph)FUR-3-yl], [0730;5-(3-Et-Ph)FUR-3-yl], [0731;5-(4-Et-Ph)FUR-3-yl], [0732;5-(2-CF3-Ph)FUR-3-yl], [0733;5-(3-CF3-Ph)FUR-3-yl], [0734;5-(4-CF3-Ph)FUR-3-yl], [0735;5-(2-OMe-Ph)FUR-3-yl], [0736;5-(3-OMe-Ph)FUR-3-yl], [0737;5-(4-OMe-Ph)FUR-3-yl], [0738;5-(2-OEt-Ph)FUR-3-yl], [0739;5-(3-OEt-Ph)FUR-3-yl], [0740;5-(4-OEt-Ph)FUR-3-yl], [0741;5-(4-F-2-F-Ph)FUR-3-yl], [0742;5-(4-Cl-2-F-Ph)FUR-3-yl], [0743;5-(4-Br-2-F-Ph)FUR-3-yl], [0744;5-(4-Me-2-F-Ph)FUR-3-yl], [0745;5-(4-Et-2-F-Ph)FUR-3-yl], [0746;5-(4-CF3-2-F-Ph)FUR-3-yl], [0747;5-(4-OMe-2-F-Ph)FUR-3-yl], [0748;5-(4-OEt-2-F-Ph)FUR-3-yl], [0749;5-(4-F-2-Cl-Ph)FUR-3-yl], [0750;5-(4-Cl-2-Cl-Ph)FUR-3-yl], [0751;5-(4-Br-2-Cl-Ph)FUR-3-yl], [0752;5-(4-Me-2-Cl-Ph)FUR-3-yl], [0753;5-(4-Et-2-Cl-Ph)FUR-3-yl], [0754;5-(4-CF3-2-Cl-Ph)FUR-3-yl], [0755;5-(4-OMe-2-Cl-Ph)FUR-3-yl], [0756;5-(4-OEt-2-Cl-Ph)FUR-3-yl], [0757;5-(4-F-2-Me-Ph)FUR-3-yl], [0758;5-(4-Cl-2-Me-Ph) FUR-3-yl], [0759;5-(4-Br-2-Me-Ph)FUR-3-yl], [0760;5-(4-Me-2-Me-Ph)FUR-3-yl], [0761;5-(4-Et-2-Me-Ph)FUR-3-yl], [0762;5-(4-CF3-2-Me-Ph)FUR-3-yl], [0763;5-(4-OMe-2-Me-Ph)FUR-3-yl], [0764;5-(4-OEt-2-Me-Ph)FUR-3-yl], [0765;5-(4-F-2-OMe-Ph)FUR-3-yl], [0766;5-(4-Cl-2-OMe-Ph)FUR-3-yl], [0767;5-(4-Br-2-OMe-Ph)FUR-3-yl], [0768;5-(4-Me-2-OMe-Ph)FUR-3-yl], [0769;5-(4-Et-2-OMe-Ph)FUR-3-yl], [0770;5-(4-CF3-2-OMe-Ph)FUR-3-yl], [0771;5-(4-OMe-2-OMe-Ph)FUR-3-yl], [0772;5-(4-OEt-2-OMe-Ph)FUR-3-yl], [0773;5-(4-F-2-OEt-Ph)FUR-3-yl], [0774;5-(4-Cl-2-OEt-Ph)FUR-3-yl], [0775;5-(4-Br-2-OEt-Ph)FUR-3-yl], [0776;5-(4-Me-2-OEt-Ph)FUR-3-yl], [0777;5-(4-Et-2-OEt-Ph)FUR-3-yl], [0778;5-(4-CF3-2-OEt-Ph)FUR-3-yl], [0779;5-(4-OMe-2-OEt-Ph)FUR-3-yl], [0780;5-(4-OEt-2-OEt-Ph)FUR-3-yl], [0781;2-phenylTHA-4-yl], [0782;2-(2-F-Ph)THA-4-yl], [0783;2-(3-F-Ph)THA-4-yl], [0784;2-(4-F-Ph)THA-4-yl], [0785;2-(2-Cl-Ph)THA-4-yl], [0786;2-(3-Cl-Ph)THA-4-yl], [0787;2-(4-Cl-Ph)THA-4-yl], [0788;2-(2-Br-Ph)THA-4-yl], [0789;2-(3-Br-Ph)THA-4-yl], [0790;2-(4-Br-Ph)THA-4-yl], [0791;2-(2-Me-Ph)THA-4-yl], [0792;2-(3-Me-Ph)THA-4-yl], [0793;2-(4-Me-Ph)THA-4-yl], [0794;2-(2-Et-Ph)THA-4-yl], [0795;2-(3-Et-Ph)THA-4-yl], [0796;2-(4-Et-Ph)THA-4-yl], [0797;2-(2-CF3-Ph)THA-4-yl], [0798;2-(3-CF3-Ph)THA-4-yl], [0799;2-(4-CF3-Ph)THA-4-yl], [0800;2-(2-OMe-Ph)THA-4-yl], [0801;2-(3-OMe-Ph)THA-4-yl], [0802;2-(4-OMe-Ph)THA-4-yl], [0803;2-(2-OEt-Ph)THA-4-yl], [0804;2-(3-OEt-Ph)THA-4-yl], [0805;2-(4-OEt-Ph)THA-4-yl], [0806;2-(4-F-2-F-Ph)THA-4-yl], [0807;2-(4-Cl-2-F-Ph)THA-4-yl], [0808;2-(4-Br-2-F-Ph)THA-4-yl], [0809;2-(4-Me-2-F-Ph)THA-4-yl], [0810;2-(4-Et-2-F-Ph)THA-4-yl], [0811;2-(4-CF3-2-F-Ph)THA-4-yl], [0812;2-(4-OMe-2-F-Ph)THA-4-yl], [0813;2-(4-OEt-2-F-Ph)THA-4-yl], [0814;2-(4-F-2-Cl-Ph)THA-4-yl], [0815;2-(4-Cl-2-Cl-Ph)THA-4-yl], [0816;2-(4-Br-2-Cl-Ph)THA-4-yl], [0817;2-(4-Me-2-Cl-Ph)THA-4-yl], [0818;2-(4-Et-2-Cl-Ph)THA-4-yl], [0819;2-(4-CF3-2-Cl-Ph)THA-4-yl], [0820;2-(4-OMe-2-Cl-Ph)THA-4-yl], [0821;2-(4-OEt-2-Cl-Ph)THA-4-yl], [0822;2-(4-F-2-Me-Ph)THA-4-yl], [0823;2-(4-Cl-2-Me-Ph)THA-4-yl], [0824;2-(4-Br-2-Me-Ph)THA-4-yl], [0825;2-(4-Me-2-Me-Ph)THA-4-yl], [0826;2-(4-Et-2-Me-Ph)THA-4-yl], [0827;2-(4-CF3-2-Me-Ph)THA-4-yl], [0828;2-(4-OMe-2-Me-Ph)THA-4-yl], [0829;2-(4-OEt-2-Me-Ph)THA-4-yl], [0830;2-(4-F-2-OMe-Ph)THA-4-yl], [0831;2-(4-Cl-2-OMe-Ph)THA-4-yl], [0832;2-(4-Br-2-OMe-Ph)THA-4-yl], [0833;2-(4-Me-2-OMe-Ph)THA-4-yl], [0834;2-(4-Et-2-OMe-Ph)THA-4-yl], [0835;2-(4-CF3-2-OMe-Ph)THA-4-yl], [0836;2-(4-OMe-2-OMe-Ph)THA-4-yl], [0837;2-(4-OEt-2-OMe-Ph)THA-4-yl], [0838;2-(4-F-2-OEt-Ph)THA-4-yl], [0839;2-(4-Cl-2-OEt-Ph)THA-4-yl], [0840;2-(4-Br-2-OEt-Ph)THA-4-yl], [0841;2-(4-Me-2-OEt-Ph)THA-4-yl], [0842;2-(4-Et-2-OEt-Ph)THA-4-yl], [0843;2-(4-CF3-2-OEt-Ph)THA-4-yl], [0844;2-(4-OMe-2-OEt-Ph)THA-4-yl], [0845;2-(4-OEt-2-OEt-Ph)THA-4-yl], [0846;2-phenylOXA-4-yl], [0847;2-(2-F-Ph)OXA-4-yl], [0848;2-(3-F-Ph)OXA-4-yl], [0849;2-(4-F-Ph)OXA-4-yl], [0850;2-(2-Cl-Ph)OXA-4-yl], [0851;2-(3-Cl-Ph)OXA-4-yl], [0852;2-(4-Cl-Ph)OXA-4-yl], [0853;2-(2-Br-Ph)OXA-4-yl], [0854;2-(3-Br-Ph)OXA-4-yl], [0855;2-(4-Br-Ph)OXA-4-yl], [0856;2-(2-Me-Ph)OXA-4-yl], [0857;2-(3-Me-Ph)OXA-4-yl], [0858;2-(4-Me-Ph)OXA-4-yl], [0859;2-(2-Et-Ph)OXA-4-yl], [0860;2-(3-Et-Ph)OXA-4-yl], [0861;2-(4-Et-Ph)OXA-4-yl], [0862;2-(2-CF3-Ph)OXA-4-yl], [0863;2-(3-CF3-Ph)OXA-4-yl], [0864;2-(4-

CF3-Ph)OXA-4-yl], [0865;2-(2-OMe-Ph)OXA-4-yl], [0866;2-(3-OMe-Ph)OXA-4-yl], [0867;2-(4-OMe-Ph)OXA-4-yl], [0868;2-(2-OEt-Ph)OXA-4-yl], [0869;2-(3-OEt-Ph)OXA-4-yl], [0870;2-(4-OEt-Ph)OXA-4-yl], [0871;2-(4-F-2-F-Ph)OXA-4-yl], [0872;2-(4-Cl-2-F-Ph)OXA-4-yl], [0873;2-(4-Br-2-F-Ph)OXA-4-yl], [0874;2-(4-Me-2-F-Ph)OXA-4-yl], [0875;2-(4-Et-2-F-Ph)OXA-4-yl], [0876;2-(4-CF3-2-F-Ph)OXA-4-yl], [0877;2-(4-OMe-2-F-Ph)OXA-4-yl], [0878;2-(4-OEt-2-F-Ph)OXA-4-yl], [0879;2-(4-F-2-Cl-Ph)OXA-4-yl], [0880;2-(4-Cl-2-Cl-Ph)OXA-4-yl], [0881;2-(4-Br-2-Cl-Ph)OXA-4-yl], [0882;2-(4-Me-2-Cl-Ph)OXA-4-yl], [0883;2-(4-Et-2-Cl-Ph)OXA-4-yl], [0884;2-(4-CF3-2-Cl-Ph)OXA-4-yl], [0885;2-(4-OMe-2-Cl-Ph)OXA-4-yl], [0886;2-(4-OEt-2-Cl-Ph)OXA-4-yl], [0887;2-(4-F-2-Me-Ph)OXA-4-yl], [0888;2-(4-Cl-2-Me-Ph)OXA-4-yl], [0889;2-(4-Br-2-Me-Ph)OXA-4-yl], [0890;2-(4-Me-2-Me-Ph)OXA-4-yl], [0891;2-(4-Et-2-Me-Ph)OXA-4-yl], [0892;2-(4-CF3-2-Me-Ph)OXA-4-yl], [0893;2-(4-OMe-2-Me-Ph)OXA-4-yl], [0894;2-(4-OEt-2-Me-Ph)OXA-4-yl], [0895;2-(4-F-2-OMe-Ph)OXA-4-yl], [0896;2-(4-Cl-2-OMe-Ph)OXA-4-yl], [0897;2-(4-Br-2-OMe-Ph)OXA-4-yl], [0898;2-(4-Me-2-OMe-Ph)OXA-4-yl], [0899;2-(4-Et-2-OMe-Ph)OXA-4-yl], [0900;2-(4-CF3-2-OMe-Ph)OXA-4-yl], [0901;2-(4-OMe-2-OMe-Ph)OXA-4-yl], [0902;2-(4-OEt-2-OMe-Ph)OXA-4-yl], [0901;2-(4-F-2-OEt-Ph)OXA-4-yl], [0904;2-(4-Cl-2-OEt-Ph)OXA-4-yl], [0905;2-(4-Br-2-OEt-Ph)OXA-4-yl], [0906;2-(4-Me-2-OEt-Ph)OXA-4-yl], [0907;2-(4-Et-2-OEt-Ph)OXA-4-yl], [0908;2-(4-CF3-2-OEt-Ph)OXA-4-yl], [0909;2-(4-OMe-2-OEt-Ph)OXA-4-yl], [0910;2-(4-OEt-2-OEt-Ph)OXA-4-yl], [0911;4-Ph-1-Me-IMI-2-yl], [0912;4-(2-F-Ph)-1-Me-IMI-2-yl], [0913;4-(3-F-Ph)-1-Me-IMI-2-yl], [0914;4-(4-F-Ph)-1-Me-IMI-2-yl], [0915;4-(2-Cl-Ph)-1-Me-IMI-2-yl], [0916;4-(3-Cl-Ph)-1-Me-IMI-2-yl], [0917;4-(4-Cl-Ph)-1-Me-IMI-2-yl], [0918;4-(2-Br-Ph)-1-Me-IMI-2-yl], [0919;4-(3-Br-Ph)-1-Me-IMI-2-yl], [0920;4-(4-Br-Ph)-1-Me-IMI-2-yl], [0921;4-(2-Me-Ph)-1-Me-IMI-2-yl], [0922;4-(3-Me-Ph)-1-Me-IMI-2-yl], [0923;4-(4-Me-Ph)-1-Me-IMI-2-yl], [0924;4-(2-Et-Ph)-1-Me-IMI-2-yl], [0925;4-(3-Et-Ph)-1-Me-IMI-2-yl], [0926;4-(4-Et-Ph)-1-Me-IMI-2-yl], [0927;4-(2-CF3-Ph)-1-Me-IMI-2-yl], [0928;4-(3-CF3-Ph)-1-Me-IMI-2-yl], [0929;4-(4-CF3-Ph)-1-Me-IMI-2-yl], [0930;4-(2-OMe-Ph)-1-Me-IMI-2-yl], [0931;4-(3-OMe-Ph)-1-Me-IMI-2-yl], [0932;4-(4-OMe-Ph)-1-Me-IMI-2-yl], [0933;4-(2-OEt-Ph)-1-Me-IMI-2-yl], [0934;4-(3-OEt-Ph)-1-Me-IMI-2-yl], [0935;4-(4-OEt-Ph)-1-Me-IMI-2-yl], [0936;4-(4-F-2-F-Ph)-1-Me-IMI-2-yl], [0937;4-(4-Cl-2-F-Ph)-1-Me-IMI-2-yl], [0938;4-(4-Br-2-F-Ph)-1-Me-IMI-2-yl], [0939;4-(4-Me-2-F-Ph)-1-Me-IMI-2-yl], [0940;4-(4-Et-2-F-Ph)-1-Me-IMI-2-yl], [0941;4-(4-CF3-2-F-Ph)-1-Me-IMI-2-yl], [0942;4-(4-OMe-2-F-Ph)-1-Me-IMI-2-yl], [0943;4-(4-OEt-2-F-Ph)-1-Me-IMI-2-yl], [0944;4-(4-F-2-Cl-Ph)-1-Me-IMI-2-yl], [0945;4-(4-Cl-2-Cl-Ph)-1-Me-IMI-2-yl], [0946;4-(4-Br-2-Cl-Ph)-1-Me-IMI-2-yl], [0947;4-(4-Me-2-Cl-Ph)-1-Me-IMI-2-yl], [0948;4-(4-Et-2-Cl-Ph)-1-Me-IMI-2-yl], [0949;4-(4-CF3-2-Cl-Ph)-1-Me-IMI-2-yl], [0950;4-(4-OMe-2-Cl-Ph)-1-Me-IMI-2-yl], [0951;4-(4-OEt-2-Cl-Ph)-1-Me-IMI-2-yl], [0952;4-(4-F-2-Me-Ph)-1-Me-IMI-2-yl], [0953;4-(4-Cl-2-Me-Ph)-1-Me-IMI-2-yl], [0954;4-(4-Br-2-Me-Ph)-1-Me-IMI-2-yl], [0955;4-(4-Me-2-Me-Ph)-1-Me-IMI-2-yl], [0956;4-(4-Et-2-Me-Ph)-1-Me-IMI-2-yl], [0957;4-(4-CF3-2-Me-Ph)-1-Me-IMI-2-yl], [0958;4-(4-OMe-2-Me-Ph)-1-Me-IMI-2-yl], [0959;4-(4-OEt-2-Me-Ph)-1-Me-IMI-2-yl], [0960;4-(4-F-2-OMe-Ph)-1-Me-IMI-2-yl], [0961;4-(4-Cl-2-OMe-Ph)-1-Me-IMI-2-yl], [0962;4-(4-Br-2-OMe-Ph)-1-Me-IMI-2-yl], [0963;4-(4-Me-2-OMe-Ph)-1-Me-IMI-2-yl], [0964;4-(4-Et-2-OMe-Ph)-1-Me-IMI-2-yl], [0965;4-(4-CF3-2-OMe-Ph)-1-Me-IMI-2-yl], [0966;4-(4-OMe-2-OMe-Ph)-1-Me-IMI-2-yl], [0967;4-(4-OEt-2-OMe-Ph)-1-Me-IMI-2-yl], [0968;4-(4-F-2-OEt-Ph)-1-Me-IMI-2-yl], [0969;4-(4-Cl-2-OEt-Ph)-1-Me-IMI-2-yl], [0970;4-(4-Br-2-OEt-Ph)-1-Me-IMI-2-yl], [0971;4-(4-Me-2-OEt-Ph)-1-Me-IMI-2-yl], [0972;4-(4-Et-2-OEt-Ph)-1-Me-IMI-2-yl], [0973;4-(4-CF3-2-OEt-Ph)-1-Me-IMI-2-yl], [0974;4-(4-OMe-2-OEt-Ph)-1-Me-IMI-2-yl], [0975;4-(4-OEt-2-OEt-Ph)-1-Me-IMI-2-yl], [0976;2-Ph-1-Me-IMI-4-yl], [0977;2-(2-F-Ph)-1-Me-IMI-4-yl], [0978;2-(3-F-Ph)-1-Me-IMI-4-yl], [0979;2-(4-F-Ph)-1-Me-IMI-4-yl], [0980;2-(2-Cl-Ph)-1-Me-IMI-4-yl], [0981;2-(3-Cl-Ph)-1-Me-IMI-4-yl], [0982;2-(4-Cl-Ph)-1-Me-IMI-4-yl], [0983;2-(2-Br-Ph)-1-Me-IMI-4-yl], [0984;2-(3-Br-Ph)-1-Me-IMI-4-yl], [0985;2-(4-Br-Ph)-1-Me-IMI-4-yl], [0986;2-(2-Me-Ph)-1-Me-IMI-4-yl], [0987;2-(3-Me-Ph)-1-Me-IMI-4-yl], [0988;2-(4-Me-Ph)-1-Me-IMI-4-yl], [0989;2-(2-Et-Ph)-1-Me-IMI-4-yl], [0990;2-(3-Et-Ph)-1-Me-IMI-4-yl], [0991;2-(4-Et-Ph)-1-Me-IMI-4-yl], [0992;2-(2-CF3-Ph)-1-Me-IMI-4-yl], [0993;2-(3-CF3-Ph)-1-Me-IMI-4-yl], [0994;2-(4-CF3-Ph)-1-Me-IMI-4-yl], [0995;2-(2-OMe-Ph)-1-Me-IMI-4-yl], [0996;2-(3-OMe-Ph)-1-Me-IMI-4-yl], [0997;2-(4-OMe-Ph)-1-Me-IMI-4-yl], [0998;2-(2-OEt-Ph)-1-Me-IMI-4-yl], [0999;2-(3-OEt-Ph)-1-Me-IMI-4-yl], [1000;2-(4-OEt-Ph)-1-Me-IMI-4-yl], [1001;2-(4-F-2-F-Ph)-1-Me-IMI-4-yl], [1002;2-(4-Cl-2-F-Ph)-1-Me-IMI-4-yl], [1003;2-(4-Br-2-F-Ph)-1-Me-IMI-4-yl], [1004;2-(4-Me-2-F-Ph)-1-Me-IMI-4-yl], [1005;2-(4-Et-2-F-Ph)-1-Me-IMI-4-yl], [1006;2-(4-CF3-2-F-Ph)-1-Me-IMI-4-yl], [1007;2-(4-OMe-2-F-Ph)-1-Me-IMI-4-yl], [1008;2-(4-OEt-2-F-Ph)-1-Me-IMI-4-yl], [1009;2-(4-F-2-Cl-Ph)-1-Me-IMI-4-yl], [1010;2-(4-Cl-2-Cl-Ph)-1-Me-IMI-4-yl], [1011;2-(4-Br-2-Cl-Ph)-1-Me-IMI-4-yl], [1012;2-(4-Me-2-Cl-Ph)-1-Me-IMI-4-yl], [1013;2-(4-Et-2-Cl-Ph)-1-Me-IMI-4-yl], [1014;2-(4-CF3-2-Cl-Ph)-1-Me-IMI-4-yl], [1015;2-(4-OMe-2-Cl-Ph)-1-Me-IMI-4-yl], [1016;2-(4-OEt-2-Cl-Ph)-1-Me-IMI-4-yl], [1017;2-(4-F-2-Me-Ph)-1-Me-IMI-4-yl], [1018;2-(4-Cl-2-Me-Ph)-1-Me-IMI-4-yl], [1019;2-(4-Br-2-Me-Ph)-1-Me-IMI-4-yl], [1020;2-(4-Me-2-Me-Ph)-1-Me-IMI-4-yl], [1021;2-(4-Et-2-Me-Ph)-1-Me-IMI-4-yl], [1022;2-(4-CF3-2-Me-Ph)-1-Me-IMI-4-yl], [1023;2-(4-OMe-2-Me-Ph)-1-Me-IMI-4-yl], [1024;2-(4-OEt-2-Me-Ph)-1-Me-IMI-4-yl], [1025;2-(4-F-2-OMe-Ph)-1-Me-IMI-4-yl], [1026;2-(4-Cl-2-OMe-Ph)-1-Me-IMI-4-yl], [1027;2-(4-Br-2-OMe-Ph)-1-Me-IMI-4-yl], [1028;2-(4-Me-2-OMe-Ph)-1-Me-IMI-4-yl], [1029;2-(4-Et-2-OMe-Ph)-1-Me-IMI-4-yl], [1030;2-(4-CF3-2-OMe-Ph)-1-Me-IMI-4-yl], [1031;2-(4-OMe-2-OMe-Ph)-1-Me-IMI-4-yl], [1032;2-(4-OEt-2-OMe-Ph)-1-Me-IMI-4-yl], [1033;2-(4-F-2-OEt-Ph)-1-Me-IMI-4-yl], [1034;2-(4-Cl-2-OEt-Ph)-1-Me-IMI-4-yl], [1035;2-(4-Br-2-OEt-Ph)-1-Me-IMI-4-yl], [1036;2-(4-Me-2-OEt-Ph)-1-Me-IMI-4-yl], [1037;2-(4-Et-2-OEt-Ph)-1-Me-IMI-4-yl], [1038;2-(4-CF3-2-OEt-Ph)-1-Me-IMI-4-yl], [1039;2-(4-OMe-2-OEt-Ph)-1-Me-IMI-4-yl], [1040;2-(4-OEt-2-OEt-Ph)-1-Me-IMI-4-yl] [1041;3-phenylPRL-5-yl], [1042;3-(2-F-Ph)PRL-5-yl], [1043;3-(3-F-Ph)PRL-5-yl], [1044;3-(4-F-Ph)PRL-5-yl], [1045;3-(2-Cl-Ph)PRL-5-yl], [1046;3-(3-Cl-Ph)PRL-5-yl], [1047;3-(4-Cl-Ph)PRL-5-yl], [1048;3-(2-Br-Ph)PRL-5-yl], [1049;3-(3-Br-Ph)PRL-5-yl], [1050;3-(4-Br-Ph)PRL-5-yl], [1051;3-(2-Me-Ph)PRL-5-yl], [1052;3-(3-Me-Ph)PRL-5-yl], [1053;3-(4-Me-Ph)PRL-5-yl], [1054;3-(2-Et-Ph)PRL-5-yl], [1055;3-(3-Et-Ph)PRL-5-yl], [1056;3-(4-Et-Ph)PRL-5-yl], [1057;3-(2-CF3-Ph)PRL-5-yl], [1058;3-(3-CF3-Ph)PRL-5-yl], [1059;3-(4-CF3-Ph)PRL-5-yl], [1060;3-(2-OMe-Ph)PRL-5-yl], [1061;3-(3-OMe-Ph)PRL-5-yl], [1062;3-(4-OMe-Ph)PRL-5-yl], [1063;3-(2-OEt-Ph)PRL-5-yl], [1064;3-(3-OEt- Ph)PRL-5-yl], [1065;3-(4-OEt-Ph)PRL-5-yl], [1066;3-(4-F-2-F-Ph)PRL-5-yl], [1067;3-(4-Cl-2-F-Ph)PRL-5-yl], [1068;3-(4-Br-2-F-Ph)PRL-5-yl], [1069;3-(4-Me-2-F-Ph)PRL-5-yl], [1070;3-(4-Et-2-F-Ph)PRL-5-yl], [1071;3-(4-CF3-2-F-Ph)PRL-5-yl], [1072;3-(4-OMe-2-F-Ph)PRL-5-yl], [1073;3-(4-OEt-2-F-Ph)PRL-5-yl], [1074;3-(4-F-2-Cl-Ph)PRL-5-yl], [1075;3-(4-Cl-2-Cl-Ph)PRL-5-yl], [1076;3-(4-Br-2-Cl-Ph)PRL-5-yl], [1077;3-(4-Me-2-Cl-Ph)PRL-5-yl], [1078;3-(4-Et-2-Cl-Ph)PRL-5-yl], [1079;3-(4-CF3-2-Cl-Ph)PRL-5-yl], [1080;3-(4-OMe-2-Cl-Ph)PRL-5-yl], [1081;3-(4-OEt-2-Cl-Ph)PRL-5-yl], [1082;3-(4-F-2-Me-Ph)PRL-5-yl], [1083;3-(4-Cl-2-Me-Ph)PRL-5-yl], [1084;3-(4-Br-2-Me-Ph)PRL-5-yl], [1085;3-(4-Me-2-Me-Ph)PRL-5-yl], [1086;3-(4-Et-2-Me-Ph)PRL-5-yl], [1087;3-(4-CF3-2-Me-Ph)PRL-5-yl], [1088;3-(4-OMe-2-Me-Ph)PRL-5-yl], [1089;3-(4-OEt-2-Me-Ph)PRL-5-yl], [1090;3-(4-F-2-OMe-Ph)PRL-5-yl], [1091;3-(4-Cl-2-OMe-Ph)PRL-5-yl], [1092;3-(4-Br-2-OMe-Ph)PRL-5-yl], [1093;3-(4-Me-2-OMe-Ph)PRL-5-yl], [1094;3-(4-Et-2-OMe-Ph)PRL-5-yl], [1095;3-(4-CF3-2-OMe-Ph)PRL-5-yl], [1096;3-(4-OMe-2-OMe-Ph)PRL-5-yl], [1097;3-(4-OEt-2-OMe-Ph)PRL-5-yl], [1098;3-(4-F-2-OEt-Ph)PRL-5-yl], [1099;3-(4-Cl-2-OEt-Ph)PRL-5-yl], [1100;3-(4-Br-2-OEt-Ph)PRL-5-yl],
[1101;3-(4-Me-2-OEt-Ph)PRL-5-yl], [1102;3-(4-Et-2-OEt-Ph)PRL-5-yl], [1103;3-(4-CF3-2-OEt-Ph)PRL-5-yl], [1104;3-(4-OMe-2-OEt-Ph)PRL-5-yl], [1105;3-(4-OEt-2-OEt-Ph)PRL-5-yl], [1106;5-phenylPRL-2-yl], [1107;5-(2-F-Ph)PRL-2-yl], [1108;5-(3-F-Ph)PRL-2-yl], [1109;5-(4-F-Ph)PRL-2-yl], [1110;5-(2-Cl-Ph)PRL-2-yl], [1111;5-(3-Cl-Ph)PRL-2-yl], [1112;5-(4-Cl-Ph)PRL-2-yl], [1113;5-(2-Br-Ph)PRL-2-yl], [1114;5-(3-Br-Ph)PRL-2-yl], [1115;5-(4-Br-Ph)PRL-2-yl], [1116;5-(2-Me-Ph)PRL-2-yl], [1117;5-(3-Me-Ph)PRL-2-yl], [1118;5-(4-Me-Ph)PRL-2-yl], [1119;5-(2-Et-Ph)PRL-2-yl], [1120;5-(3-Et-Ph)PRL-2-yl], [1121;5-(4-Et-Ph)PRL-2-yl], [1122;5-(2-CF3-Ph)PRL-2-yl], [1123;5-(3-CF3-Ph)PRL-2-yl], [1124;5-(4-CF3-Ph)PRL-2-yl], [1125;5-(2-OMe-Ph)PRL-2-yl], [1126;5-(3-OMe-Ph)PRL-2-yl], [1127;5-(4-OMe-Ph)PRL-2-yl], [1128;5-(2-OEt-Ph)PRL-2-yl], [1129;5-(3-OEt-Ph)PRL-2-yl], [1130;5-(4-OEt-Ph)PRL-2-yl], [1131;5-(4-F-2-F-Ph)PRL-2-yl], [1132;5-(4-Cl-2-F-Ph)PRL-2-yl], [1133;5-(4-Br-2-F-Ph)PRL-2-yl], [1134;5-(4-Me-2-F-Ph)PRL-2-yl], [1135;5-(4-Et-2-F-Ph)PRL-2-yl], [1136;5-(4-CF3-2-F-Ph)PRL-2-yl], [1137;5-(4-OMe-2-F-Ph)PRL-2-yl], [1138;5-(4-OEt-2-F-Ph)PRL-2-yl], [1139;5-(4-F-2-Cl-Ph)PRL-2-yl], [1140;5-(4-Cl-2-Cl-Ph)PRL-2-yl], [1141;5-(4-Br-2-Cl-Ph)PRL-2-yl], [1142;5-(4-Me-2-Cl-Ph)PRL-2-yl], [1143;5-(4-Et-2-Cl-Ph)PRL-2-yl], [1144;5-(4-CF3-2-Cl-Ph)PRL-2-yl], [1145;5-(4-OMe-2-Cl-Ph)PRL-2-yl], [1146;5-(4-OEt-2-Cl-Ph)PRL-2-yl], [1147;5-(4-F-2-Me-Ph)PRL-2-yl], [1148;5-(4-Cl-2-Me-Ph)PRL-2-yl], [1149;5-(4-Br-2-Me-Ph)PRL-2-yl], [1150;5-(4-Me-2-Me-Ph)PRL-2-yl], [1151;5-(4-Et-2-Me-Ph)PRL-2-yl], [1152;5-(4-CF3-2-Me-Ph)PRL-2-yl], [1153;5-(4-OMe-2-Me-Ph)PRL-2-yl], [1154;5-(4-OEt-2-Me-Ph)PRL-2-yl], [1155;5-(4-F-2-OMe-Ph)PRL-2-yl], [1156;5-(4-Cl-2-OMe-Ph)PRL-2-yl], [1157;5-(4-Br-2-OMe-Ph)PRL-2-yl], [1158;5-(4-Me-2-OMe-Ph)PRL-2-yl], [1159;5-(4-Et-2-OMe-Ph)PRL-2-yl], [1160;5-(4-CF3-2-OMe-Ph)PRL-2-yl], [1161;5-(4-OMe-2-OMe-Ph)PRL-2-yl], [1162;5-(4-OEt-2-OMe-Ph)PRL-2-yl], [1163;5-(4-F-2-OEt-Ph)PRL-2-yl], [1164;5-(4-Cl-2-OEt-Ph)PRL-2-yl], [1165;5-(4-Br-2-OEt-Ph)PRL-2-yl], [1166;5-(4-Me-2-OEt-Ph)PRL-2-yl], [1167;5-(4-Et-2-OEt-Ph)PRL-2-yl], [1168;5-(4-CF3-2-OEt-Ph)PRL-2-yl], [1169;5-(4-OMe-2-OEt-Ph)PRL-2-yl], [1170;5-(4-OEt-2-OEt-Ph)PRL-2-yl], [1171;5-phenylPRL-3-yl], [1172;5-(2-F-Ph)PRL-3-yl], [1173;5-(3-F-Ph)PRL-3-yl], [1174;5-(4-F-Ph)PRL-3-yl], [1175;5-(2-Cl-Ph)PRL-3-yl], [1176;5-(3-Cl-Ph)PRL-3-yl], [1177;5-(4-Cl-Ph)PRL-3-yl], [1178;5-(2-Br-Ph)PRL-3-yl], [1179;5-(3-Br-Ph)PRL-3-yl], [1180;5-(4-Br-Ph)PRL-3-yl], [1181;5-(2-Me-Ph)PRL-3-yl], [1182;5-(3-Me-Ph)PRL-3-yl], [1183;5-(4-Me-Ph)PRL-3-yl], [1184;5-(2-Et-Ph)PRL-3-yl], [1185;5-(3-Et-Ph)PRL-3-yl], [1186;5-(4-Et-Ph)PRL-3-yl], [1187;5-(2-CF3-Ph)PRL-3-yl], [1188;5-(3-CF3-Ph)PRL-3-yl], [1189;5-(4-CF3-Ph)PRL-3-yl], [1190;5-(2-OMe-Ph)PRL-3-yl], [1191;5-(3-OMe-Ph)PRL-3-yl], [1192;5-(4-OMe-Ph)PRL-3-yl], [1193;5-(2-OEt-Ph)PRL-3-yl], [1194;5-(3-OEt-Ph)PRL-3-yl], [1195;5-(4-OEt-Ph)PRL-3-yl], [1196;5-(4-F-2-F-Ph)PRL-3-yl], [1197;5-(4-Cl-2-F-Ph)PRL-3-yl], [1198;5-(4-Br-2-F-Ph)PRL-3-yl], [1199;5-(4-Me-2-F-Ph)PRL-3-yl], [1200;5-(4-Et-2-F-Ph)PRL-3-yl], [1201;5-(4-CF3-2-F-Ph)PRL-3-yl], [1202;5-(4-OMe-2-F-Ph)PRL-3-yl], [1203;5-(4-OEt-2-F-Ph)PRL-3-yl], [1204;5-(4-F-2-Cl-Ph)PRL-3-yl], [1205;5-(4-Cl-2-Cl-Ph)PRL-3-yl], [1206;5-(4-Br-2-Cl-Ph)PRL-3-yl], [1207;5-(4-Me-2-Cl-Ph)PRL-3-yl], [1208;5-(4-Et-2-Cl-Ph)PRL-3-yl], [1209;5-(4-CF3-2-Cl-Ph)PRL-3-yl], [1210;5-(4-OMe-2-Cl-Ph)PRL-3-yl], [1211;5-(4-OEt-2-Cl-Ph)PRL-3-yl], [1212;5-(4-F-2-Me-Ph)PRL-3-yl], [1213;5-(4-Cl-2-Me-Ph)PRL-3-yl], [1214;5-(4-Br-2-Me-Ph)PRL-3-yl], [1215;5-(4-Me-2-Me-Ph)PRL-3-yl], [1216;5-(4-Et-2-Me-Ph)PRL-3-yl], [1217;5-(4-CF3-2-Me-Ph)PRL-3-yl], [1218;5-(4-OMe-2-Me-Ph)PRL-3-yl], [1219;5-(4-OEt-2-Me-Ph)PRL-3-yl], [1220;5-(4-F-2-OMe-Ph)PRL-3-yl], [1221;5-(4-Cl-2-OMe-Ph)PRL-3-yl], [1222;5-(4-Br-2-OMe-Ph)PRL-3-yl], [1223;5-(4-Me-2-OMe-Ph)PRL-3-yl], [1224;5-(4-Et-2-OMe-Ph)PRL-3-yl], [1225;5-(4-CF3-2-OMe-Ph)PRL-3-yl], [1226;5-(4-OMe-2-OMe-Ph)PRL-3-yl], [1227;5-(4-OEt-2-OMe-Ph)PRL-3-yl], [1228;5-(4-F-2-OEt-Ph)PRL-3-yl], [1229;5-(4-Cl-2-OEt-Ph)PRL-3-yl], [1230;5-(4-Br-2-OEt-Ph)PRL-3-yl], [1231;5-(4-Me-2-OEt-Ph)PRL-3-yl], [1232;5-(4-Et-2-OEt-Ph)PRL-3-yl], [1233;5-(4-CF3-2-OEt-Ph)PRL-3-yl], [1234;5-(4-OMe-2-OEt-Ph)PRL-3-yl], [1235;5-(4-OEt-2-OEt-Ph)PRL-3-yl], [1236;2-phenylTDA-5-yl], [1237;2-(2-F-Ph)TDA-5-yl], [1238;2-(3-F-Ph)TDA-5-yl], [1239;2-(4-F-Ph)TDA-5-yl], [1240;2-(2-Cl-Ph)TDA-5-yl], [1241;2-(3-Cl-Ph)TDA-5-yl], [1242;2-(4-Cl-Ph)TDA-5-yl], [1243;2-(2-Br-Ph)TDA-5-yl], [1244;2-(3-Br-Ph)TDA-5-yl], [1245;2-(4-Br-Ph)TDA-5-yl], [1246;2-(2-Me-Ph)TDA-5-yl], [1247;2-(3-Me-Ph)TDA-5-yl], [1248;2-(4-Me-Ph)TDA-5-yl], [1249;2-(2-Et-Ph)TDA-5-yl], [1250;2-(3-Et-Ph)TDA-5-yl], [1251;2-(4-Et-Ph)TDA-5-yl], [1252;2-(2-CF3-Ph)TDA-5-yl], [1253;2-(3-CF3-Ph)TDA-5-yl], [1254;2-(4-CF3-Ph)TDA-5-yl], [1255;2-(2-OMe-Ph)TDA-5-yl], [1256;2-(3-OMe-Ph)TDA-5-yl], [1257;2-(4-OMe-Ph)TDA-5-yl], [1258;2-(2-OEt-Ph)TDA-5-yl], [1259;2-(3-OEt-Ph)TDA-5-yl], [1260;2-(4-OEt-Ph)TDA-5-yl], [1261;2-(4-F-2-F-Ph)TDA-5-yl], [1262;2-(4-Cl-2-F-Ph)TDA-5-yl], [1263;2-(4-Br-2-F-Ph)TDA-5-yl], [1264;2-(4-Me-2-F-Ph)TDA-5-yl], [1265;2-(4-Et-2-F-Ph)TDA-5-yl], [1266;2-(4-CF3-2-F-Ph)TDA-5-yl], [1267;2-(4-OMe-2-F-Ph)TDA-5-yl], [1268;2-(4-OEt-2-F-Ph)TDA-5-yl], [1269;2-(4-F-2-Cl-Ph)TDA-5-yl], [1270;2-(4-Cl-2-Cl-Ph)TDA-5-yl], [1271;2-(4-Br-2-Cl-Ph)TDA-5-yl], [1272;2-(4-Me-2-Cl-Ph)TDA-5-yl], [1273;2-(4-Et-2-Cl-Ph)TDA-5-yl], [1274;2-(4-CF3-2-Cl-Ph)TDA-5-yl], [1275;2-(4-OMe-2-Cl-Ph)TDA-5-yl], [1276;2-(4-OEt-2-Cl-Ph)TDA-5-yl], [1277;2-(4-F-2-Me-Ph)TDA-5-yl], [1278;2-(4-Cl-2-Me-Ph)TDA-5-yl], [1279;2-(4-Br-2-Me-Ph)TDA-5-yl], [1280;2-(4-Me-2-Me-Ph)TDA-5-yl], [1281;2-(4-Et-2-Me-Ph)TDA-5-yl], [1282;2-(4-CF3-2-Me-Ph)TDA-5-yl], [1283;2-(4-OMe-2-Me-Ph)TDA-5-yl], [1284;2-(4-OEt-2-Me-Ph)TDA-5-yl], [1285;2-(4-F-2-OMe-Ph)TDA-5-yl], [1286;2-(4-Cl-2-OMe-Ph)TDA-5-yl], [1287;2-(4-Br-2-OMe-Ph)TDA-5-yl], [1288;2-(4-Me-2-OMe-Ph)TDA-5-yl], [1289;2-(4-Et-2-OMe-Ph)TDA-5-yl],

[1290;2-(4-CF3-2-OMe-Ph)TDA-5-yl], [1291;2-(4-OMe-2-OMe-Ph)TDA-5-yl], [1292;2-(4-OEt-2-OMe-Ph)TDA-5-yl], [1293;2-(4-F-2-OEt-Ph)TDA-5-yl], [1294;2-(4-Cl-2-OEt-Ph)TDA-5-yl], [1295;2-(4-Br-2-OEt-Ph)TDA-5-yl], [1296;2-(4-Me-2-OEt-Ph)TDA-5-yl], [1297;2-(4-Et-2-OEt-Ph)TDA-5-yl], [1298;2-(4-CF3-2-OEt-Ph)TDA-5-yl], [1299;2-(4-OMe-2-OEt-Ph)TDA-5-yl], [1300;2-(4-OEt-2-OEt-Ph)TDA-5-yl]

Formulation Examples will be shown below.

Formulation Example 1

Fifty parts (50 parts) of any one of the present compounds 1 to 30, 3 parts of calcium ligninsulfonate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds 1 to 30 and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds 1 to 9, 88 parts of kaolin clay, and 10 parts of talc are thoroughly ground and mixed to obtain each formulation.

Formulation Example 4

Five parts (5 parts) of any one of the present compounds 1 to 9, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds 1 to 9, 1 part of synthetic hydrated silicon oxide, 2 parts of calcium ligninsulfonate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds 1 to 9, 35 parts of white carbon containing 50 parts of a polyoxyethylene alkyl ether sulfate ammonium salt, and 55 parts of water were finely ground by a wet grinding method to obtain each formulation.

The following Test Examples will show that the present compounds are useful for controlling plant diseases.

The control effect was evaluated by visually observing the area of lesion spots on each of test plants at the time of investigation, and comparing the area of lesion spots on a plant treated with the present compound with that on an untreated plant.

Test Example 1

Each of plastic pots was filled with sandy loam and barley (cultivar: NISHINOHOSHI) was sowed and grown in a greenhouse for 7 days. Then, each water dilution prepared by adjusting so as to contain a predetermined concentration (500 ppm) of any one compound of the present compounds 1, 2, 3, 4, 5, 6, 7, 8, 9, 10, 14, 19, 21, 22, 23, 24, 25, 28, 29, and 30 was sprayed over stems and leaves of the barley so that it sufficiently adhered to the surface of the leaves of the barley. After spraying, the plant was air-dried. After 2 days, an aqueous suspension containing spores of barley net blotch fungus (Pyrenophora teres) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound 1, 2, 3, 4, 5, 6, 7, 8, 9, 10, 14, 19, 21, 22, 23, 24, 25, 28, 29, or 30 was 30% or less of that on an untreated plant.

Test Example 2

Each of plastic pots was filled with sandy loam and barley (cultivar: NISHINOHOSHI) was sowed and grown in a greenhouse for 7 days. Then, each mixture having a predetermined concentration (200 ppm), which contains the present compound 26 or 27, was adjusted with water, and then each water dilution thus obtained was sprayed over stems and leaves of the barley so that it sufficiently adhered to the surface of the leaves of the barley. After spraying, the plant was air-dried. After 2 days, an aqueous suspension containing spores of barley net blotch fungus (Pyrenophora teres) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound 26 or 27 was 30% or less of that on an untreated plant.

Test Example 3

Each of plastic pots was filled with sandy loam and barley (cultivar: NISHINOHOSHI) was sowed and grown in a greenhouse for 7 days. Then, a mixture containing the present compound 3, 5, 6, 7, 8, 9, 12, 16, 17, 18, 19, 20, 21, 22, 23, 24, 25, 26, 27, or 30 in a predetermined concentration (200 ppm) was prepared by adjusting with water and then sprayed over stems and leaves of the barley so that it sufficiently adhered to the surface of the leaves of the barley. After spraying, the plant was air-dried. After 2 days, an aqueous suspension containing spores of barley leaf blotch fungus (Rhynchosporium secalis) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound 3, 5, 6, 7, 8, 9, 12, 16, 17, 18, 19, 20, 21, 22, 23, 24, 25, 26, 27, or 30 was 30% or less of that on an untreated plant.

Test Example 4

Each of plastic pots was filled with sandy loam and wheat (cultivar: APOGEE) was sowed and grown in a greenhouse for 10 days. Then, each water dilution prepared by adjusting so as to contain a predetermined concentration (500 ppm) of any one compound of the present compounds 1, 2, 3, 5, 6, 7, 8, 10, 11, 19, 21, 22, 25, 26, 28, and 29 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with the present compound 1, 2, 3, 5, 6, 7, 8, 10, 11, 19, 21, 22, 25, 26, 28, or 29 was 30% or less of that on an untreated plant.

Test Example 5

Each of plastic pots was filled with sandy loam and wheat (cultivar: APOGEE) was sowed and grown in a greenhouse for 10 days. Thereafter, an aqueous suspension containing spores of wheat leaf blotch fungus (*Septoria tritici*) was sprayed over the wheat to inoculate the spores. The wheat was left to stand at 18° C. under high humidity condition for 3 days and then air-dried. Each water dilution containing a surfactant prepared by adjusting so as to contain a predetermined concentration (200 ppm) of any one compound of the present compounds 5, 8, 16, 17, 18, 25, and 29 was sprayed over stems and leaves of the wheat so that it sufficiently adhered to the surface of the leaves of the wheat. After spraying, the plant was air-dried. The plant was left to stand under illumination for 14 to 18 days, and then the area of lesion spots was investigated. As a result, the area of lesion spots on the plant treated with the present compound 5, 8, 16, 17, 18, 25, or 29 was 30% or less of that on an untreated plant.

Test Example 6

Each of plastic pots was filled with sandy loam and wheat (cultivar: SHIROGANE) was sowed and grown in a greenhouse for 9 days. Then, each water dilution prepared by adjusting so as to contain a predetermined concentration (500 ppm) of any one compound of the present compounds 2, 8, and 30 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with the present compound 2, 8, or 30 was 30% or less of that on an untreated plant.

Test Example 7

Each of plastic pots was filled with sandy loam and wheat (cultivar: SHIROGANE) was sowed and grown in a greenhouse for 9 days. Then, each water dilution prepared by adjusting so as to contain a predetermined concentration (200 ppm) of any one compound of the present compounds 22, 23, 25, and 29 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated.

As a result, it has been found that the area of lesion spots on the plant treated with the present compound 22, 23, 25, or 29 was 30% or less of that on an untreated plant.

Test Example 8

Each of plastic pots was filled with sandy loam and cucumber (cultivar: SAGAMI HANJIRO) was sowed and grown in a greenhouse for 12 days. Then, each water dilution prepared by adjusting so as to contain a predetermined concentration (500 ppm) of any one compound of the present compounds 1, 2, 5, 8, 19, 25, and 29 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with the present compound 1, 2, 5, 8, 19, 25, or 29 was 30% or less of that on an untreated plant.

Test Example 9

Each of plastic pots was filled with sandy loam and cucumber (cultivar: SAGAMI HANJIRO) was sowed and grown in a greenhouse for 12 days. Then, each water dilution prepared by adjusting so as to contain a predetermined concentration (200 ppm) of any one compound of the present compounds 16 and 17 was sprayed over stems and leaves of the cucumber so that it sufficiently adhered to the surface of the leaves of the cucumber. After spraying, the plant was air-dried and then inoculated by sprinkling with spores of cucumber powdery mildew fungus (Sphaerotheca *fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion spots was investigated. As a result, the area of lesion spots on the plant treated with the present compound 16 or 17 was 30% or less of that on an untreated plant.

Test Example 10

Each of plastic pots was filled with sandy loam and cucumber (cultivar: SAGAMI HANJIRO) was sowed and grown in a greenhouse for 19 days. Then, each water dilution prepared by adjusting so as to contain a predetermined concentration (200 ppm) of any one compound of the present compounds 7, 16, 17, 20, 21, 22, 24, 25, 26, 27, and 30 was sprayed over stems and leaves of the cucumber so that it sufficiently adhered to the surface of the leaves of the cucumber. After spraying, the plant was air-dried and then inoculated by sprinkling with spores of cucumber target leaf spot fungus (*Corynespora cassiicola*). After the inoculation, the plant was cultivated in a greenhouse at 24° C. in the daytime and 20° C. at night for 7 days, and then the area of lesion spots was investigated. As a result, the area of lesion spots on the plant treated with the present compound 7, 16, 17, 20, 21, 22, 24, 25, 26, 27, or 30 was 30% or less of that on an untreated plant.

Test Example 11

Each of plastic pots was filled with sandy loam and rice (cultivar: NIHONBARE) was sowed and grown in a greenhouse for 20 days. Then, each water dilution prepared by adjusting so as to contain a predetermined concentration (500 ppm) of the present compound 8 was sprayed over stems and leaves so that it sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) left to stand for 6 days at 24° C. in the daytime and 20° C. at night under high humidity condition, while being in contact with each other, and then the area of lesion spots was investigated. As a result, the lesion areas on the plant treated with the present compound 8 were 30% or less with respect to the lesion area on the non-treated plant.

Test Example 12

Each of plastic pots was filled with sandy loam and rice (cultivar: NIHONBARE) was sowed and grown in a greenhouse for 20 days. Then, each water dilution prepared by adjusting so as to contain a predetermined concentration (200 ppm) of any one compound of the present compounds 12, 16, 17, 18, 19, 21, 23, 24, 25, 29, and 30 was sprayed over stems and leaves so that it sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) left to stand for 6 days at 24° C. in the daytime and 20° C. at night under high humidity condition, while being in contact with each other, and then the area of lesion spots was investigated.

As a result, the lesion areas on the plant treated with the present compound 12, 16, 17, 18, 19, 21, 23, 24, 25, 29, or 30 were 30% or less with respect to the lesion area on the non-treated plant.

Test Example 13

Each of plastic pots was filled with sandy loam and soybean (cultivar: KUROSENGOKU) was sowed and grown in a greenhouse for 13 days. Then, each water dilution prepared by adjusting so as to contain a predetermined concentration (200 ppm) of any one compound of the present compounds 8 and 29 was sprayed over stems and leaves of the soybean so that it sufficiently adhered to the surface of the leaves of the soybean. After spraying, the plant was air-dried. After 2 days, an aqueous suspension containing spores of soybean rust fungus (*Phakopsora pachyrhizi*) was sprayed to inoculate the spores. After completion of the inoculation, the plant was left to stand for 3 days in a greenhouse at 23° C. in the daytime and 20° C. at night under high humidity condition and cultivated in a greenhouse for 14 days, and then the area of lesion spots was investigated. As a result, it has been found that the area of lesion spots on the plant treated with the present compound 8 or 29 was 30% or less of that on an untreated plant.

Test Example 14

Each of plastic pots was filled with sandy loam and kidney bean (cultivar: NAGAUZURA SAIYTOU) was sowed and grown in a greenhouse for 8 days. Then, each water dilution prepared by adjusting so as to contain a predetermined concentration (500 ppm) of any one compound of the present compounds 1, 2, 5, 7, and 8 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with the present compound 1, 2, 5, 7, or 8 was 30% or less of that on an untreated plant.

Test Example 15

Each of plastic pots was filled with sandy loam and kidney bean (cultivar: NAGAUZURA SAIYTOU) was sowed and grown in a greenhouse for 8 days. Then, each water dilution prepared by adjusting so as to contain a predetermined concentration (200 ppm) of any one compound of the present compounds 3, 5, 7, 8, 20, 23, 25, 26, and 29 was sprayed over stems and leaves of the kidney bean so that it sufficiently adhered to the surface of the leaves of the kidney bean. After spraying, the plant was air-dried and a PDA (potato dextrose agar) medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with the present compound 3, 5, 7, 8, 20, 23, 25, 26, or 29 was 30% or less of that on an untreated plant.

Test Example 16

Each of plastic pots was filled with sandy loam and tomato (cultivar: PATIO) was sowed and grown in a greenhouse for 20 days. Then, each water dilution prepared by adjusting so as to contain a predetermined concentration (500 ppm) of the present compound 8 was sprayed over stems and leaves of the tomato seedling so that it sufficiently adhered to the surface of the leaves of the tomato seedling. After air-drying so as to dry the dilution on the leaves, an aqueous suspension containing spores of tomato late blight fungus (*Phytophthora infestans*) was sprayed to inoculate the spores. After completion of the inoculation, the seedling was at first left to stand at 23° C. under high humidity condition for one day and then cultivated in an air-conditioned room at 20° C. for 4 days. Thereafter, the area of lesion spots was investigated. As a result, it has been found that the area of lesion spots on the plant treated with the present compound 8 was 30% or less of that on an untreated plant.

Test Example 17

Each of plastic pots was filled with sandy loam and wheat (cultivar: SHIROGANE) was sowed and grown in a greenhouse for 9 days. Then, each water dilution prepared by adjusting so as to contain a predetermined concentration (200 ppm) of any one compound of the present compounds 22, 23, 25, and 29 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated.

As a result, it has been found that the area of lesion spots on the plant treated with the present compound 22, 23, 25, or 29 was 30% or less of that on an untreated plant.

Test Example 18

Each of plastic pots was filled with sandy loam and wheat (cultivar: SHIROGANE) was sowed and grown in a greenhouse for 9 days. Then, each water dilution prepared by adjusting so as to contain a predetermined concentration (200 ppm) of any one compound of the present compounds 12, 17, 18, 22, 23, 25, and 29 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated.

As a result, it has been found that the area of lesion spots on the plant treated with the present compound 12, 17, 18, 22, 23, 25, or 30 was 30% or less of that on an untreated plant.

Test Example 19

Each of plastic pots was filled with sandy loam and wheat (cultivar: APOGEE) was sowed and grown in a greenhouse for 10 days. Thereafter, an aqueous suspension containing spores of wheat leaf blotch fungus (*Septoria tritici*) was sprayed over the wheat to inoculate the spores. The wheat was left to stand at 18° C. under high humidity condition for 3 days and then air-dried. Each water dilution prepared by adjusting so as to contain a predetermined concentration (200 ppm) of any one compound of the present compounds 5, 8, 16, 17, 18, 25, and 29 was sprayed over stems and leaves of the wheat so that it sufficiently adhered to the surface of the leaves of the wheat. After spraying, the plant was air-dried. The plant was left to stand under illumination for 14 to 18 days, and then the area of lesion spots was investigated. As a result, the area of lesion spots on the plant treated with the present compound 5, 8, 16, 17, 18, 25, or 29 was 30% or less of that on an untreated plant.

Test Example 20

In accordance with Formulation Example 2, a formulation was obtained from each of the present compounds 4, 10, and 28, and then diluted with deionized water so as to contain 500 ppm of an active ingredient to obtain a test chemical solution.

Cabbage (cultivar: GREEN BALL) was sowed and grown in a polyethylene cup until the third to fourth true leaf was developed. The test chemical solution was sprayed over the cabbage at a rate of 20 mL per cup. After drying the chemical solution, the cabbage cut from the base was disposed in a polyethylene cup (5.5 cm in diameter) with a filter paper laid on the bottom. Five (5) heads of third-instar larvae of diamondback moth (*Plutella xylostella*) were released and then a lid was put on the cup. After storage at 25° C. for 5 days, the number of the surviving insects was counted and mortality was calculated by the following equation.

Mortality (%)=(number of dead insects/number of tested insects)×100

As a result, the present compounds 4, 10, and 28 showed 80% or more of mortality in the area treated with the test chemical solution.

Test Example 21

Each of the present compounds 15 and 29 was formulated into a preparation in accordance with Formulation Example 2, which was diluted with deionized water so as to contain 500 ppm of an active ingredient to obtain a test chemical solution.

The test chemical solution (0.7 mL) was added to 100 mL of deionized water to thereby adjust the concentration of the active ingredient to 3.5 ppm. Twenty (20) heads of last instar larvae of common house mosquito (*Culex pipiens pallens*) were released in the solution. After 1 day, the number of the dead insects was counted.

Mortality was determined by the following equation.

Mortality (%)=(number of dead insects/number of tested insects)×100

As a result, the present compounds 15 and 29 showed 95% of mortality.

Test Example 22

A test chemical solution used in the present test example was prepared by diluting each of the present compounds 5, 15, and 29 with deionized water to thereby adjust the concentration of an active ingredient to 500 ppm.

Thirty (30) heads of cotton aphid (*Aphis gossypii*) (including adults and larvae) were released on the leaves of cucumber grown in a polyethylene cup until the first true leaf was developed. Next day, 20 mL of the test chemical solution was sprayed. After 6 days, the number of the surviving insects was counted and the control value was calculated by the following equation.

Control value (%)={1−($Cb \times Tai$)/($Cai \times Tb$)}×100 wherein symbols in the equation represent the followings:
Cb: Number of insects before spraying chemical solution in untreated area;
Cai: Number of surviving insects in untreated area;
Tb: Number of insects before spraying chemical solution in treated area; and
Tai: Number of surviving insects in treated area.

As a result, the present compounds 5, 15, and 29 showed 90% or more of the control value.

The present compound has control activity against pests and is useful as an active ingredient of a pest control agent.

The invention claimed is:
1. A tetrazolinone compound represented by formula (1):

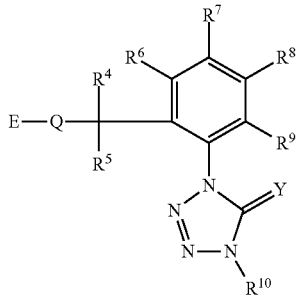

(1)

wherein
E represents a 5-membered aromatic heterocyclic group selected from Group $P^2$;
$R^4$ and $R^5$ each independently represents a hydrogen atom;
$R^6$ represents an alkyl group having 1-12 carbon atoms, a halogen atom, a haloalkyl group having 1-12 carbon atoms, a cycloalkyl group having 3-12 carbon atoms, a halocycloalkyl group having 3-12 carbon atoms, an alkoxy group having 1-12 carbon atoms, a haloalkoxy group having 1-12 carbon atoms, an alkylthio group having 1-12 carbon atoms, a haloalkylthio group having 1-12 carbon atoms, an alkenyl group having 2-12 carbon atoms, a haloalkenyl group having 2-12 carbon atoms;
$R^7$, $R^8$, and $R^9$ each independently represents a hydrogen atom;
$R^{10}$ represents an alkyl group having 1-3 carbon atoms;
Y represents an oxygen atom; and
Q represents an oxygen atom, or a sulfur atom:
Group $P^2$ consisting of the following structural formulas:

E1
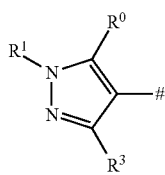

E8
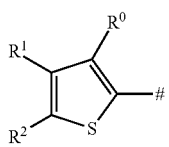

E11
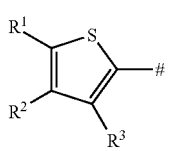

E14
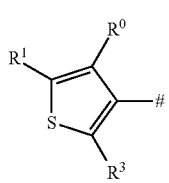

E19
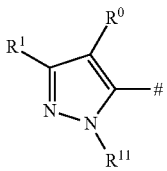

E20
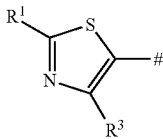

E21
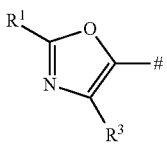

E23
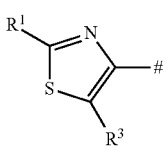

E24
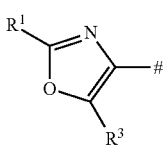

E28
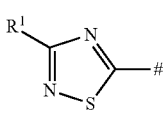

E31
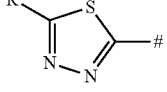

E34
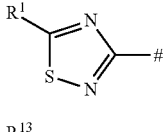

E37
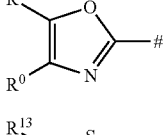

E38
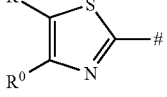

E39
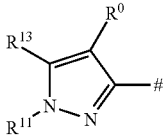

in which the symbol # represents a binding site for Q;
$R^0$, $R^2$, and $R^3$ each independently represents a hydrogen atom, a halogen atom, an alkyl group having 1-6 carbon atoms, a haloalkyl group having 1-6 carbon atoms, an alkenyl group having 2-6 carbon atoms, a haloalkenyl group having 2-6 carbon atoms, an alkynyl group having 2-6 carbon atoms, a haloalkynyl group having 2-6 carbon atoms, an alkoxycarbonyl group having 2-6 carbon atoms, a carboxy group, or a cyano group;

$R^1$ represents an aryl group having 6-16 carbon atoms which optionally has one or more atoms or groups selected from Group $P^1$, an aralkyl group having 7-18 carbon atoms which optionally has one or more atoms or groups selected from Group $P^1$, a cycloalkyl group having 3-12 carbon atoms which optionally has one or more atoms or groups selected from Group $P^1$, an adamantyl group optionally having one or more atoms or groups selected from Group $P^1$, or a hydrogen atom, wherein, when the aryl group having 6-16 carbon atoms, the aralkyl group having 7-18 carbon atoms, the cycloalkyl group having 3-12 carbon atoms, and the adamantyl group have two or more atoms or groups selected from Group $P^1$, the atoms or groups may be the same or different to each other;

$R^{11}$ represents a hydrogen atom, an alkyl group having 1-6 carbon atoms, a haloalkyl group having 1-6 carbon atoms, an alkenyl group having 2-6 carbon atoms, a haloalkenyl group having 2-6 carbon atoms, an alkynyl group having 2-6 carbon atoms, or a haloalkynyl group having 2-6 carbon atoms;

$R^{13}$ represents an aryl group having 6-16 carbon atoms which optionally has one or more atoms or groups selected from Group $P^1$, an aralkyl group having 7-18 carbon atoms which optionally has one or more atoms or groups selected from Group $P^1$, a cycloalkyl group having 3-12 carbon atoms which optionally has one or more atoms or groups selected from Group $P^1$, or an adamantyl group optionally having one or more atoms or groups selected from Group $P^1$, wherein, when two or more atoms or groups selected from Group $P^1$ are present, the atoms or groups may be the same or different to each other:

Group $P^1$ consisting of a halogen atom, an alkyl group having 1-12 carbon atoms, a haloalkyl group having 1-12 carbon atoms, an alkoxy group having 1-12 carbon atoms, a haloalkoxy group having 1-12 carbon atoms, an alkylthio group having 1-12 carbon atoms, a haloalkylthio group having 1-12 carbon atoms, a carboxy group, a formyl group, a nitro group, a cyano group, a hydroxy group, a sulfanyl group, a pentafluorosulfanyl group, an alkenyl group having 2-12 carbon atoms, a haloalkenyl group having 2-12 carbon atoms, an alkynyl group having 2-12 carbon atoms, a haloalkynyl group having 2-12 carbon atoms, a cycloalkyl group having 3-12 carbon atoms, a halocycloalkyl group having 3-12 carbon atoms, a cycloalkyloxy group having 3-12 carbon atoms, a halocycloalkyloxy group having 3-12 carbon atoms, a cycloalkylthio group having 3-12 carbon atoms, an alkenyloxy group having 2-12 carbon atoms, an alkynyloxy group having 2-12 carbon atoms, a haloalkenyloxy group having 2-12 carbon atoms, a haloalkynyloxy group having 2-12 carbon atoms, an alkynylthio group having 2-12 carbon atoms, an alkenylthio group having 2-12 carbon atoms, a haloalkenylthio group having 2-12 carbon atoms, a haloalkynylthio group having 2-12 carbon atoms, an alkylcarbonyl group having 2-12 carbon atoms, a haloalkylcarbonyl group having 2-12 carbon atoms, an alkylcarbonyloxy group having 2-12 carbon atoms, an alkylcarbonylthio group having 2-12 carbon atoms, an alkoxycarbonyl group having 2-12 carbon atoms, an aryl group having 6-16 carbon atoms, a haloaryl group having 6-16 carbon atoms, an aryloxy group having 6-16 carbon atoms, a haloaryloxy group having 6-16 carbon atoms, an arylthio group having 6-16 carbon atoms, a haloarylthio group having 6-16 carbon atoms, an aralkyl group having 7-18 carbon atoms, a haloaralkyl group having 7-18 carbon atoms, an arylalkoxy group having 7-18 carbon atoms, a haloarylalkoxy group having 7-18 carbon atoms, a trialkylsilyl group having 3-12 carbon atoms, a trialkylsilylethynyl group having 5-14 carbon atoms, an alkylsulfonyl group having 1-12 carbon atoms, a haloalkylsulfonyl group having 1-12 carbon atoms, an arylsulfonyl group having 6-16 carbon atoms, a haloarylsulfonyl group having 6-16 carbon atoms, an alkylsulfinyl group having 1-12 carbon atoms, a haloalkylsulfinyl group having 1-12 carbon atoms, an arylsulfinyl group having 6-16 carbon atoms, a haloarylsulfinyl group having 6-16 carbon atoms, a polyoxyalkyloxy group having 2-11 carbon atoms, an oxacycloalkyloxy group having 2-5 carbon atoms, an aminocarbonyl group which optionally has an alkyl group having 1-12 carbon atoms and/or an aryl group having 6-12 carbon atoms, an aminosulfonyl group which optionally has an alkyl group having 1-12 carbon atoms and/or an aryl group having 6-12 carbon atoms, and an amino group which optionally has an alkyl group having 1-12 carbon atoms.

2. The tetrazolinone compound according to claim 1, wherein E is E1, E8, E11, E14, E19, E20, E21, E23, E24, E28, E31, or E34.

3. The tetrazolinone compound according to claim 1, wherein E is E19;
$R^{11}$ is a hydrogen atom, an alkyl group having 1-3 carbon atoms, or a haloalkyl group having 1-3 carbon atoms;
$R^0$ is a hydrogen atom, a halogen atom, an alkyl group having 1-3 carbon atoms, or a haloalkyl group having 1-3 carbon atoms;
$R^1$ is an aryl group having 6-16 carbon atoms which optionally has one or more atoms or groups selected from Group $P^3$, or a hydrogen atom;
$R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, a haloalkoxy group having 1-3 carbon atoms, an alkylthio group having 1-3 carbon atoms, or an alkenyl group having 2-3 carbon atoms;
$R^7$, $R^8$, and $R^9$ each independently represents a hydrogen atom;
$R^{10}$ is a methyl group; and
Y and Q are oxygen atoms:
Group $P^3$ consisting of a halogen atom, an alkyl group having 1-3 carbon atoms, a haloalkyl group having 1-3 carbon atoms, an alkoxy group having 1-3 carbon atoms, a haloalkoxy group having 1-3 carbon atoms, an alkylthio group having 1-3 carbon atoms, a haloalkylthio group having 1-3 carbon atoms, a cycloalkyl group having 3-6 carbon atoms, an alkenyl group having 2-3 carbon atoms, an alkynyl group having 2-3 carbon atoms, and a cyano group.

4. The tetrazolinone compound according to claim 1, wherein E is E8 or E11;
$R^0$, $R^2$, $R^3$, $R^7$, $R^8$, and $R^9$ are hydrogen atoms;
$R^1$ is an aryl group having 6 carbon atoms which optionally has one or more atoms or groups selected from Group $P^3$, or a hydrogen atom;

$R^6$ is an alkyl group having 1-3 carbon atoms, a halogen atom, a haloalkyl group having 1-3 carbon atoms, a cycloalkyl group having 3-4 carbon atoms, an alkoxy group having 1-3 carbon atoms, a haloalkoxy group having 1-3 carbon atoms, an alkylthio group having 1-3 carbon atoms, a cyano group, an alkenyl group having 2-3 carbon atoms, or an alkynyl group having 2-3 carbon atoms;

$R^{10}$ is a methyl group; and

Y and Q are oxygen atoms.

5. A pest control agent comprising the tetrazolinone compound according to claim 1.

6. A method for controlling pests, which comprises applying an effective amount of the tetrazolinone compound according to claim 1 to plants or soil.

* * * * *